US010926226B2

(12) United States Patent
Bruno et al.

(10) Patent No.: US 10,926,226 B2
(45) Date of Patent: Feb. 23, 2021

(54) FUNCTIONALIZED MEMBRANES AND METHODS OF PRODUCTION THEREOF

(71) Applicants: Georgia Tech Research Corporation, Atlanta, GA (US); ExxonMobil Research and Engineering Company, Annandale, NJ (US)

(72) Inventors: Nicholas Bruno, Atlanta, GA (US); Ronita Mathias, Atlanta, GA (US); Yao Ma, Atlanta, GA (US); Kirstie Thompson, Atlanta, GA (US); Breanne Hamlett, Atlanta, GA (US); Ryan P. Lively, Atlanta, GA (US); Huaxing Zhou, Furlong, PA (US); M. G. Finn, Atlanta, GA (US); Dhaval Bhandari, Bridgewater, NJ (US); Craig McKay, Atlanta, GA (US); Melinda Jue, Livermore, CA (US)

(73) Assignees: ExxonMobil Research & Engineering Company Company, Annandale, NJ (US); Georgia Tech Research Corporation, Atlanta, GA (US)

( * ) Notice: Subject to any disclaimer, the term of this patent is extended or adjusted under 35 U.S.C. 154(b) by 47 days.

(21) Appl. No.: 16/295,918

(22) Filed: Mar. 7, 2019

(65) Prior Publication Data
US 2019/0275469 A1    Sep. 12, 2019

Related U.S. Application Data

(60) Provisional application No. 62/753,470, filed on Oct. 31, 2018, provisional application No. 62/640,253, filed on Mar. 8, 2018.

(51) Int. Cl.
*B01D 67/00*    (2006.01)
*B01D 71/82*    (2006.01)
(Continued)

(52) U.S. Cl.
CPC ......... *B01D 67/0006* (2013.01); *B01D 69/08* (2013.01); *B01D 71/82* (2013.01);
(Continued)

(58) Field of Classification Search
CPC ................ B01D 67/0006; B01D 69/08; B01D 2323/30; B01J 31/04; C08J 3/246
See application file for complete search history.

(56) References Cited

U.S. PATENT DOCUMENTS 5,096,585 A * 3/1992 Nguyen ............. B01D 67/0009
                                                        210/500.23
7,410,525 B1   8/2008 Liu
(Continued)

FOREIGN PATENT DOCUMENTS

CN    103566777    2/2014
EP    1965197       3/2008
(Continued)

OTHER PUBLICATIONS

Du, Naiying et al—Decarboxylation-Induced Cross-Linking of Polymers of Intrinsic Microporosity for Membrane Gas Separation—Macromolecules, 2012 (Year: 2012).*
(Continued)

*Primary Examiner* — Bradley R Spies
(74) *Attorney, Agent, or Firm* — Troutman Pepper Hamilton Sanders LLP; John A. Morrissett; Scott A. Bergeson

(57) ABSTRACT

The present invention is directed to methods of fabricating novel cross-linked membranes and to cross-linked membranes produced by the disclosed methods. Specifically, methods of fabricating cross-linked membranes according to the present invention may comprise direct crosslinking,
(Continued)

crosslinking by addition of a small molecule, interfacial crosslinking of free-standing film, and interfacial crosslinking on a solid support.

20 Claims, 22 Drawing Sheets
(20 of 22 Drawing Sheet(s) Filed in Color)

(51) Int. Cl.
| | | |
|---|---|---|
| *B01J 31/04* | (2006.01) | |
| *C08J 3/24* | (2006.01) | |
| *B01D 69/08* | (2006.01) | |
| *C07D 221/20* | (2006.01) | |
| *C07D 311/96* | (2006.01) | |
| *C07D 471/10* | (2006.01) | |
| *C07D 487/10* | (2006.01) | |
| *C08G 65/26* | (2006.01) | |

(52) U.S. Cl.
CPC .......... *C07D 221/20* (2013.01); *C07D 311/96* (2013.01); *C07D 471/10* (2013.01); *C07D 487/10* (2013.01); *C08G 65/266* (2013.01); *C08J 3/246* (2013.01); *B01D 2323/30* (2013.01); *B01J 31/04* (2013.01); *C08G 2650/50* (2013.01); *C08J 2371/00* (2013.01)

(56) References Cited

U.S. PATENT DOCUMENTS

| | | | |
|---|---|---|---|
| 7,449,146 B2 | 11/2008 | Rakow et al. | |
| 7,485,173 B1 | 2/2009 | Liu et al. | |
| 7,690,514 B2 | 4/2010 | McKeown et al. | |
| 7,758,751 B1 | 7/2010 | Liu et al. | |
| 7,943,543 B1 | 5/2011 | Liu et al. | |
| 8,378,694 B2 | 2/2013 | Moses et al. | |
| 8,459,200 B2 | 6/2013 | Battiato et al. | |
| 8,575,414 B2 | 11/2013 | Liu et al. | |
| 8,623,928 B2 | 1/2014 | Du et al. | |
| 8,686,104 B2 | 4/2014 | Du et al. | |
| 8,821,621 B2 | 9/2014 | Dwyer et al. | |
| 8,835,180 B2 | 9/2014 | Gryska et al. | |
| 8,858,692 B2 | 10/2014 | Dwyer et al. | |
| 8,969,628 B2 | 3/2015 | Priske et al. | |
| 9,018,270 B2 | 4/2015 | McKeown et al. | |
| 9,212,261 B2 | 12/2015 | McKeown et al. | |
| 9,244,008 B2 | 1/2016 | Kang et al. | |
| 9,279,792 B2 | 3/2016 | Palazzotto et al. | |
| 9,291,484 B2 | 3/2016 | Rakow | |
| 9,296,668 B2 | 3/2016 | Wendland | |
| 2005/0282005 A1 | 12/2005 | Kurano et al. | |
| 2006/0003215 A1 | 1/2006 | Noh | |
| 2007/0155953 A1 | 7/2007 | Li et al. | |
| 2007/0209505 A1 | 9/2007 | Liu et al. | |
| 2008/0070320 A1 | 3/2008 | Palazzoto et al. | |
| 2008/0203281 A1 | 8/2008 | Sanders et al. | |
| 2009/0069613 A1 | 3/2009 | Rice et al. | |
| 2009/0069617 A1 | 3/2009 | Shecterle et al. | |
| 2009/0069618 A1 | 3/2009 | Rice | |
| 2010/0019658 A1 | 1/2010 | Lin et al. | |
| 2010/0058926 A1 | 3/2010 | Yates et al. | |
| 2010/0130634 A1 | 5/2010 | Fritsch | |
| 2010/0130796 A1 | 5/2010 | Combes et al. | |
| 2010/0280216 A1 | 11/2010 | Antonietti et al. | |
| 2010/0331437 A1 | 12/2010 | Liu et al. | |
| 2011/0036775 A1* | 2/2011 | Tarquin ................ | B01D 61/022 210/654 |
| 2013/0085191 A1 | 4/2013 | Laskoski | |
| 2013/0146538 A1 | 6/2013 | Liu et al. | |
| 2013/0186177 A1 | 7/2013 | Palazzotto et al. | |
| 2013/0217799 A1 | 8/2013 | Visser et al. | |
| 2013/0239805 A1 | 9/2013 | Husain | |
| 2013/0247756 A1 | 9/2013 | Li et al. | |
| 2014/0251897 A1 | 9/2014 | Livingston et al. | |
| 2014/0255636 A1 | 9/2014 | Odeh et al. | |
| 2015/0194681 A1 | 7/2015 | Liu et al. | |
| 2015/0239806 A1 | 8/2015 | Wendland | |
| 2016/0035986 A1 | 2/2016 | Chung et al. | |
| 2016/0082429 A1 | 3/2016 | Wendland | |
| 2016/0367948 A1 | 12/2016 | Song et al. | |
| 2017/0338414 A1 | 11/2017 | Mujica-Fernaud et al. | |

FOREIGN PATENT DOCUMENTS

| | | |
|---|---|---|
| EP | 2397218 | 12/2011 |
| WO | WO2005113121 | 12/2005 |
| WO | WO2009001065 | 12/2008 |
| WO | WO2009045733 | 4/2009 |
| WO | WO2009103070 | 8/2009 |
| WO | WO2010002404 | 1/2010 |
| WO | WO2010124359 | 11/2010 |
| WO | WO2011026541 | 3/2011 |
| WO | WO2011057384 | 5/2011 |
| WO | WO2011130818 | 10/2011 |
| WO | WO2012035327 | 3/2012 |
| WO | WO2012035328 | 3/2012 |
| WO | WO2012050686 | 4/2012 |
| WO | WO2012044419 | 5/2012 |
| WO | WO2012082537 | 6/2012 |
| WO | WO2012141883 | 10/2012 |
| WO | WO2012174099 | 12/2012 |
| WO | WO2013057492 | 4/2013 |
| WO | WO2013090188 | 6/2013 |
| WO | WO2014052021 | 4/2014 |
| WO | WO2014078914 | 5/2014 |
| WO | WO2014186094 | 11/2014 |
| WO | WO2014207559 | 12/2014 |
| WO | WO2015001422 | 1/2015 |
| WO | WO2015015299 | 2/2015 |
| WO | WO2015047750 | 4/2015 |
| WO | WO2015088844 | 6/2015 |
| WO | WO2015095026 | 6/2015 |
| WO | WO2015095034 | 6/2015 |
| WO | WO2015095038 | 6/2015 |
| WO | WO2015129925 | 9/2015 |
| WO | WO2015130550 | 9/2015 |
| WO | WO2016009273 | 1/2016 |
| WO | WO2016148869 | 9/2016 |
| WO | WO2016161367 | 10/2016 |
| WO | WO2016187670 | 12/2016 |
| WO | WO2016195977 | 12/2016 |
| WO | WO2016206008 | 12/2016 |
| WO | WO2017060863 | 4/2017 |
| WO | WO2017085601 | 5/2017 |
| WO | WO2017091357 | 6/2017 |
| WO | WO2017146466 | 8/2017 |

OTHER PUBLICATIONS

Search Report and Written Opinion from PCT application No. PCT/US19/21238 dated Jul. 1, 2019.
Hart & Colina, "Ionomers of Intrinsic Microporosity: In Silico Development of Ionic-Functionalized Gas-Separation Membranes," Langmuir 2014, vol. 30, pp. 12039-12048.
Sprick, et al., (N-Heterocyclic carbene)Pd(triethylamine) Cl2 as Precatalyst for the Synthesis of Poly(triarylamine)s, O. Polym. Chem. 2013, vol. 51 pp. 4904-4911.
Rabindranath, et al., "Purple red and Luminescent Polyiminoarylenes Containing the 1,4-diketo-3,6-diphenylpyrrolo [3,4-c]pyrrole (DPP) Chromophore," Polymer 2009 vol. 50 pp. 1637-1644.
Search Report and Written Opinion from PCT application No. PCT/US19/21236 dated Jun. 26, 2019.

\* cited by examiner

FIGURE 1
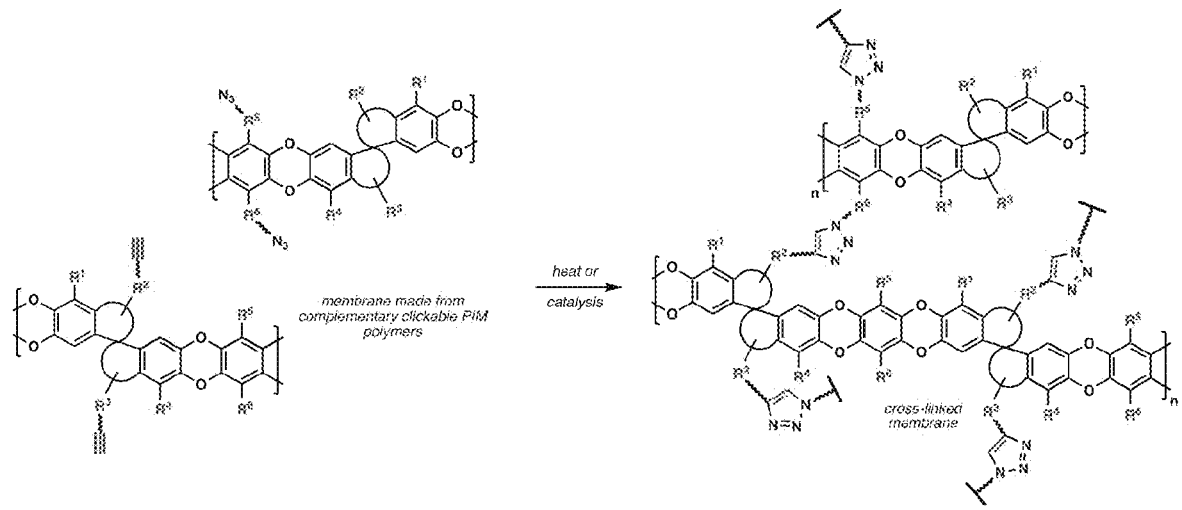
FIG 1A
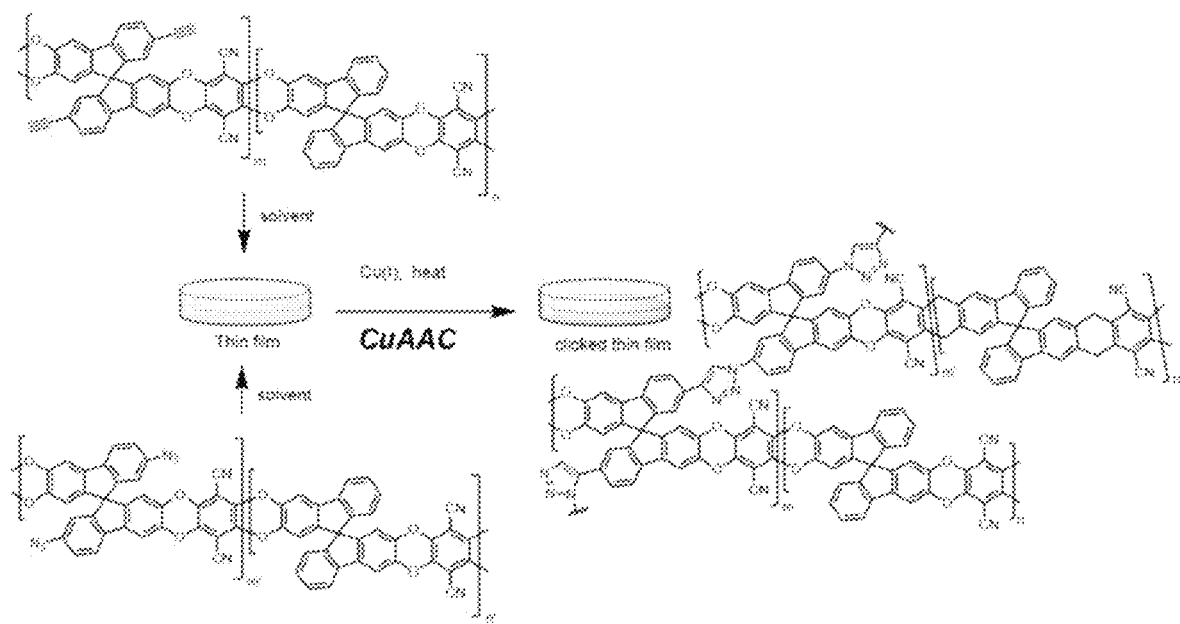
FIG 1B

FIG 2B            FIG 2C

FIGURE 3
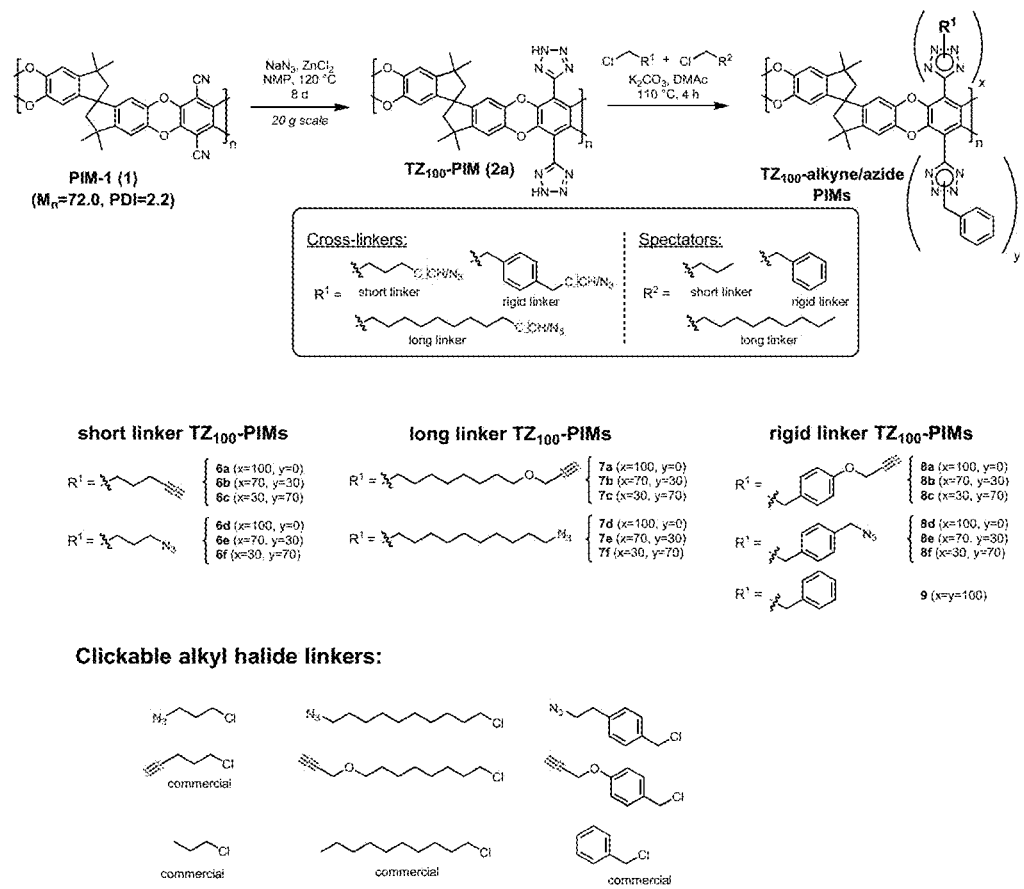
FIG 3A
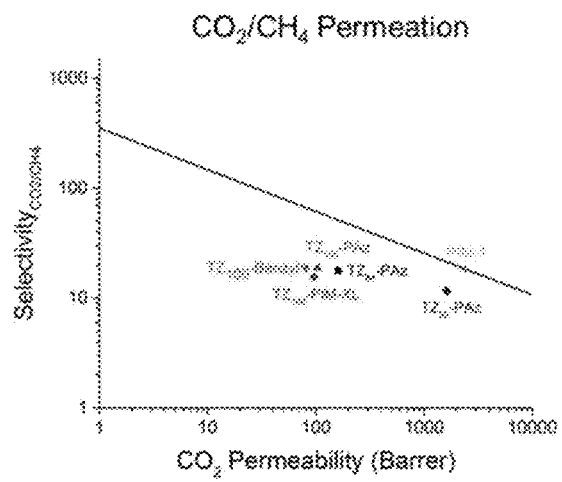
FIG 3B
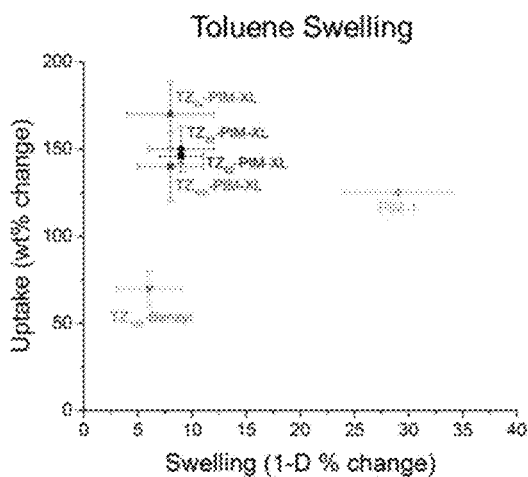
FIG 3C

FIGURE 4
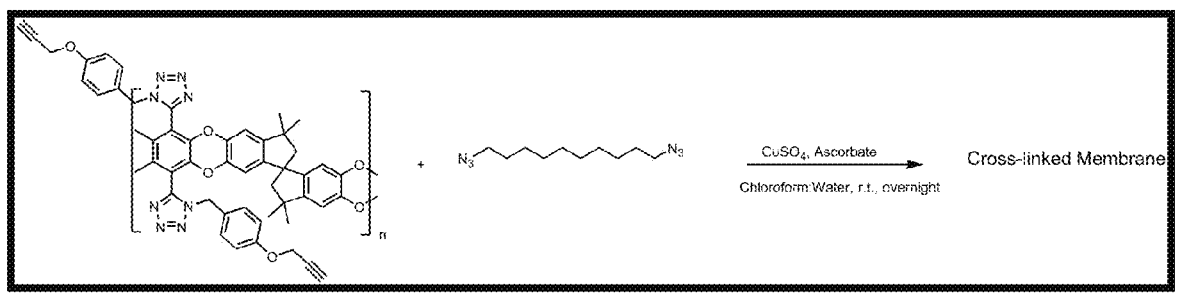
FIG 4A
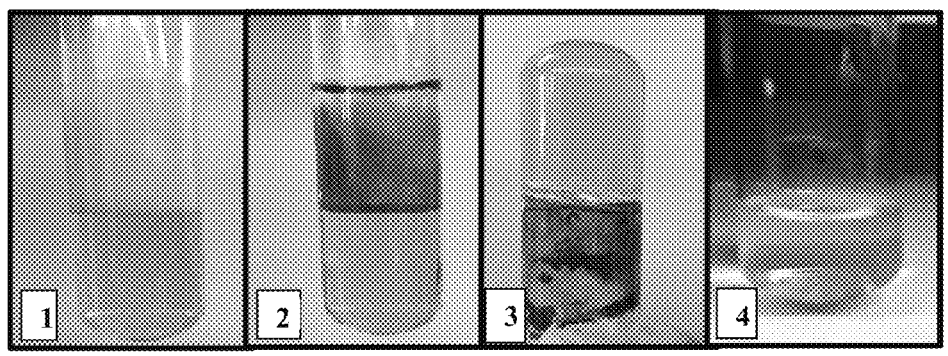
FIG 4B

FIGURE 7
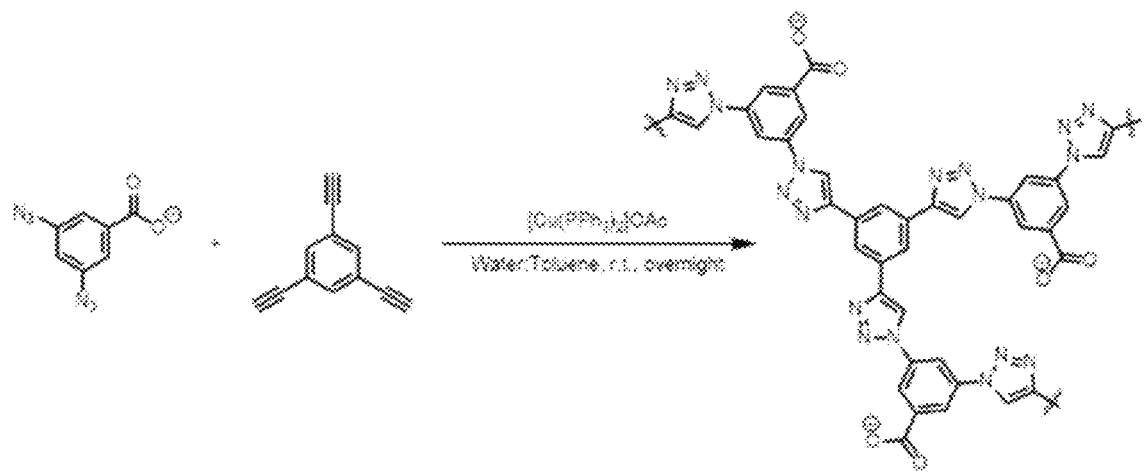
FIG 7A
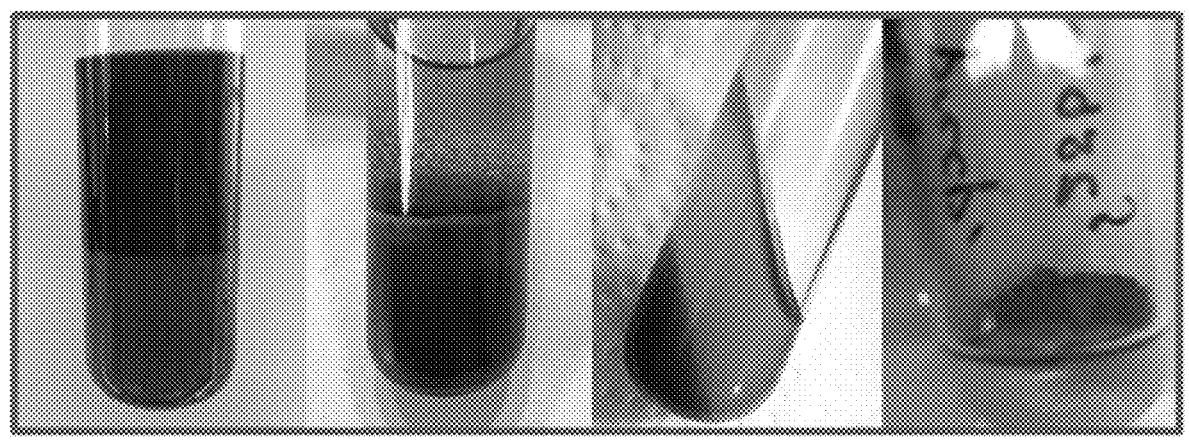
FIG 7B

FIGURE 8
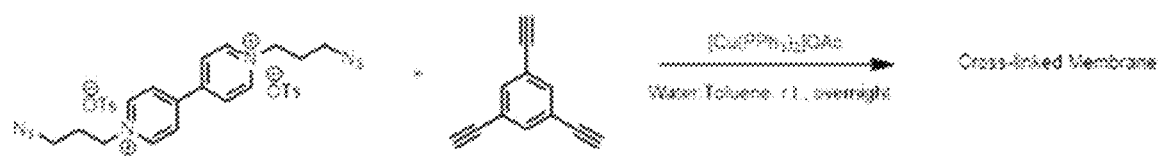
FIG 8A
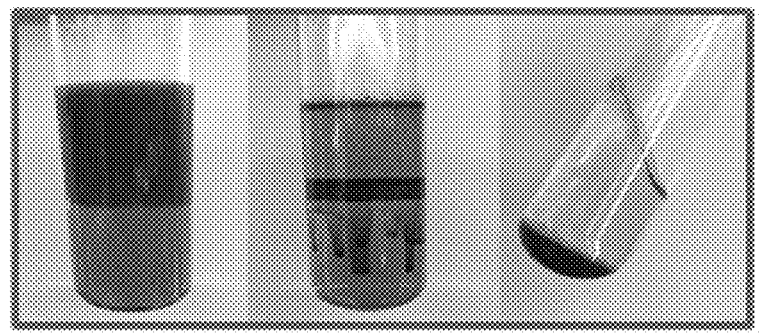
FIG 8B

FIGURE 9
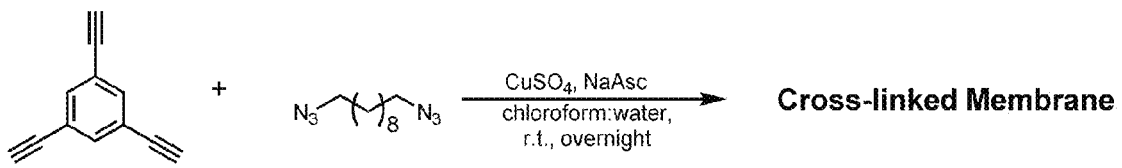
FIG 9A
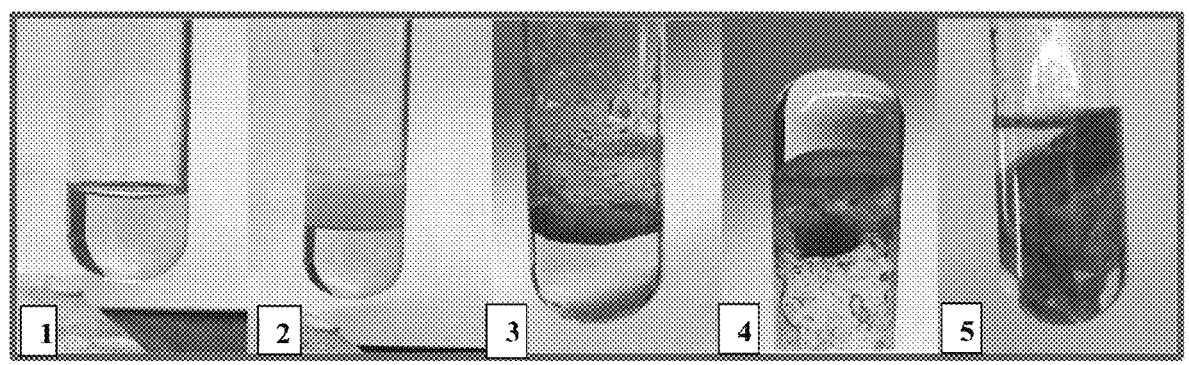
FIG 9B

FIGURE 10
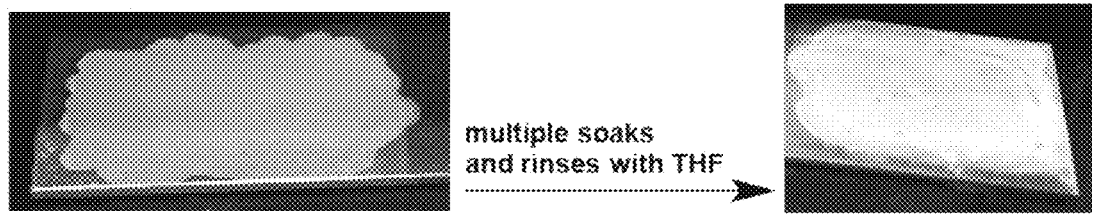
FIG 10A
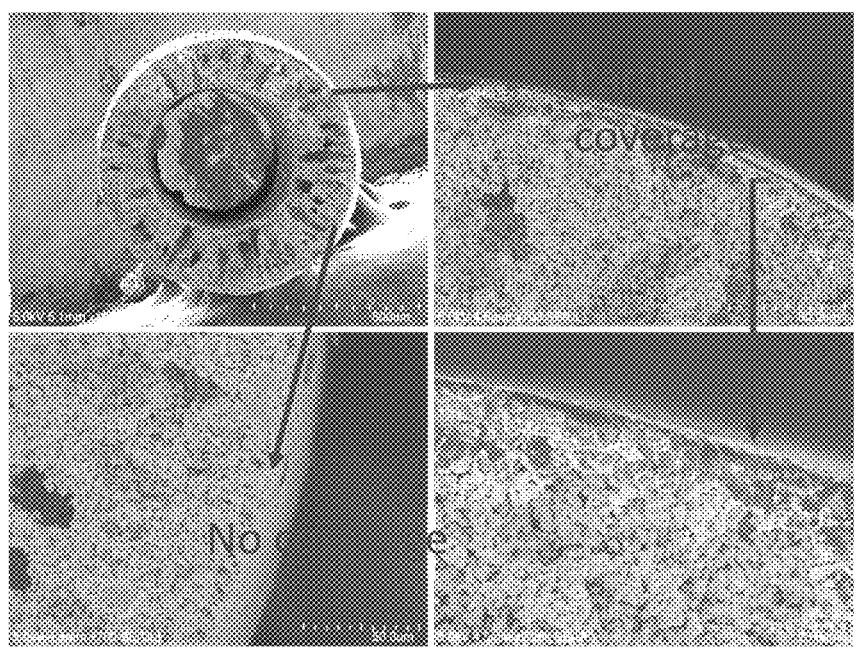
FIG 10B

FIGURE 20
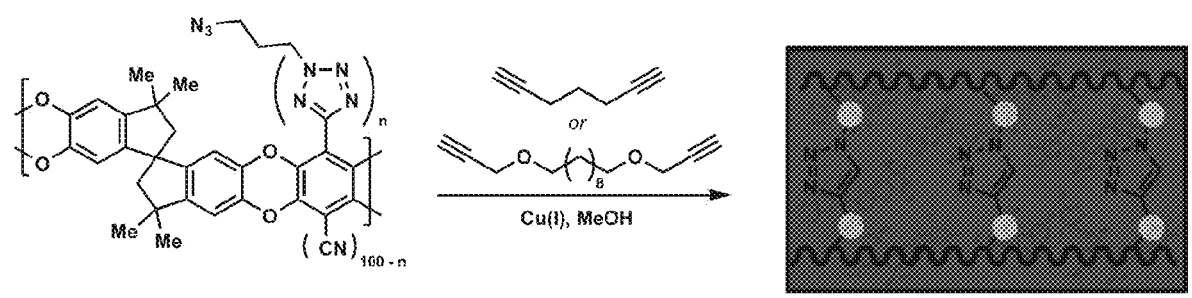
FIG 20A
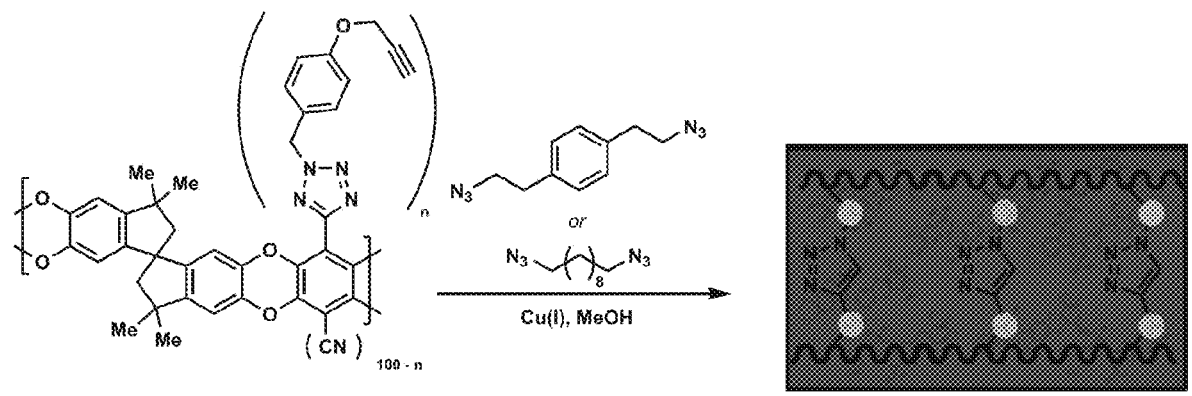
FIG 20B

FIGURE 24
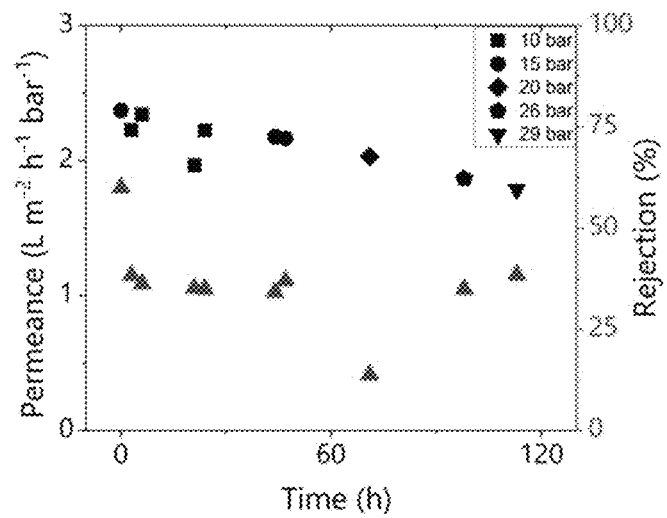
FIG 24A
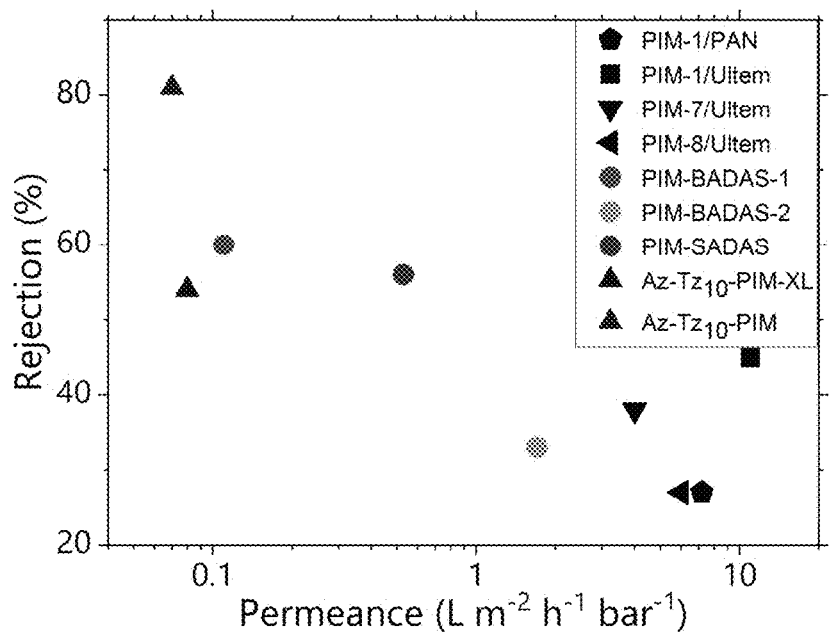
FIG 24B

FIGURE 25
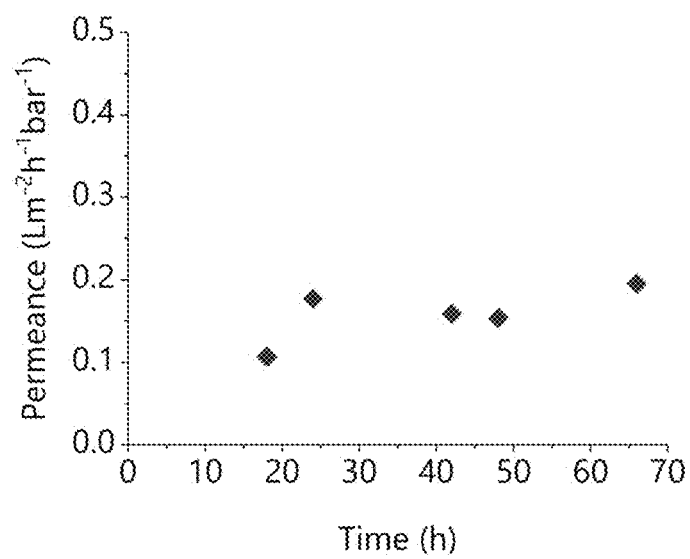
FIG 25A
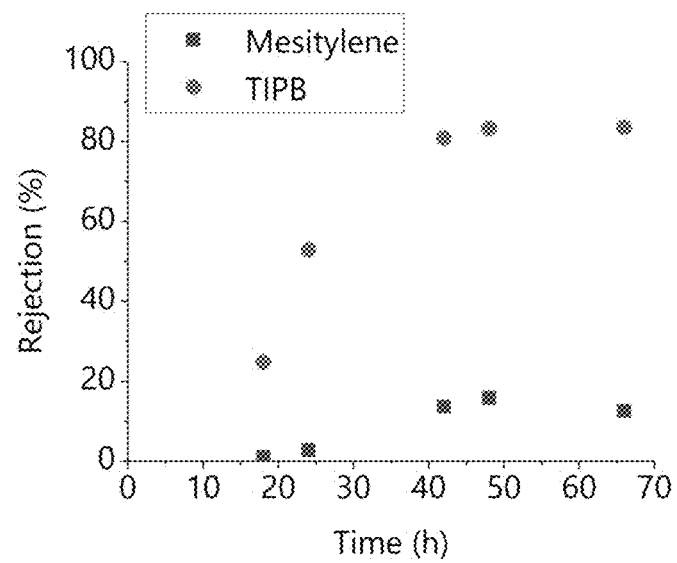
FIG 25B

FUNCTIONALIZED MEMBRANES AND METHODS OF PRODUCTION THEREOF

RELATED APPLICATIONS

This application claims the benefit of priority to U.S. Provisional Patent Application No. 62/753,470, filed 31 Oct. 2018, and titled "FUNCTIONALIZED MEMBRANES AND METHODS OF PRODUCTION THEREOF," and also claims the benefit of priority to U.S. Provisional Patent Application No. 62/640,253, filed 8 Mar. 2018, and titled "SPIROCENTRIC COMPOUNDS AND POLYMERS THEREOF," both of which are incorporated herein by reference in their entireties.

FIELD OF INVENTION

The present invention relates to methods of fabricating novel cross-linked membranes and to novel functionalized cross-linked membranes.

BACKGROUND OF THE INVENTION

Microporous hyper rigid polymeric membranes have emerged as an energy efficient molecular separation platform relative to traditional energy intensive processes. These membranes combine porosity and rigidity, allowing for high permeability and good selectivity. A known polymer of intrinsic microporosity is PIM-1, which has been studied for gas separation and organic solvent nanofiltration (OSN). PIM-1 is solution-processable, which has enabled the development of a variety of membrane morphologies including dense flat sheet, thin composite materials, and hollow fibers. Two hallmarks of PIM materials are a "site of contortion" (e.g., a spiro center) and a rigid polymer backbone. These two features provide high free volume within the glassy polymer, which enables high transport rates.

While PIM-1 has a relatively high membrane permeability for many gases in gas separation due to the "molecular ladder" structure of its polymer chains, it has only a low-to-moderate gas selectivity with a tendency to age rapidly. The applicability of PIM-1 is also limited for the separation of organic solvents in nanofiltration or reverse osmosis mode due to its tendency to swell and plasticize under common liquid hydrocarbons such as Mesitylene, Xylene, Toluene and Heptane as reported by Jue et. al. (Jue, et al., "Effect of Nonsolvent Treatments on the Microstructure of PIM-1," *Macromolecules* (2015), 48.16, 5780-5790.) PIMs also undergo swelling and plasticization in organic solvents as a result of sorbate-sorbent interactions, which result in a decrease in OSN performance. As the size difference of the organic molecules to be separated approaches MW difference of <500 g/mol or size difference of <1 nm, PIMs tend to experience a large drop in their separation capability. Extending the use of modified PIMs to the separation of smaller hydrocarbons is beneficial for a variety of applications such as crude oil refining, which currently uses large amounts of thermal energy. This will require more rigid membranes with restricted thermal motion of the polymer chains and maintenance of micropores (<2 nm) in the presence of organic media.

A variety of methods for covalent derivatization or modification of PIM-1 structures have been described, including tetrazole and methyl tetrazole formation, thioamide formation, amideoxime formation, partial nitrile hydrolysis, nitrile reduction, direct amide formation, and ortho aryl sulfonation. The introduction of polar groups to the backbone induces stronger inter-chain interactions to mitigate the sorbate-sorbent interactions and effectively lower the extent of swelling in non-polar solvents. However, the resulting polymers often display poor solubility in solvents that would be used for making membranes, and thus are not practical for further development. To bypass the poor solubility of modified PIM polymers, functionalization directly on the PIM-1 thin film membrane has been reported. (Mason, et al., "Enhancement of $CO_2$ Affinity in a Polymer of Intrinsic Microporosity by Amine Modification," *Macromolecules*, (2014), 47, 1021-1029.) Pyrolysis of the PIM-1 material to make carbon molecular sieve (CMS) membrane has also been proposed to improve the stability of the membrane under hydrocarbons by Jue et. al. (Jue, et al., "Defect-free PIM-1 hollow fiber membranes," *Journal of Membrane Science* (2017), 530, 33-41.) However, manufacturing of CMS membranes requires multiple processing steps, precise control of pyrolysis conditions, and has low product yield. However, to realize the full potential of PIM structures to produce high performing gas and organic liquid separations it is desired to make polymers that are solution processable to obtain the desired membrane morphology, after which cross-linking is used to generate a solvent stable hyper-rigid cross-linked PIM network membrane. Cross-linking the PIM will improve the selectivity between organic solvents by restricting the solvent-induced mobility of the chains. While intermolecular interactions have been used to cross-link PIM-1 (see Du et al, "Azide-based Cross-Linking of Polymers of Intrinsic Microporosity (PIMs) for Condensable Gas Separation," *Macromol. Rapid Comm.* (2011), 32, 631-636), examples of covalent cross-linking of PIM-1 rely on aggressive conditions of heat to induce non-specific decarboxylative cross-linking, oxidative cross-linking, and azide decomposition to nitrene for C—H insertion cross-linking. Another way to crosslink PIM type molecules is by UV degradation of certain functional groups. (See, e.g., U.S. Pat. No. 9,238,202B2). Such method leads to random cross-linking, which may disrupt polymer chains and needs long UV exposure. These approaches are nonspecific and generate very low levels of cross-linking.

In most reports, polymer of intrinsic microporosity (PIM) membranes were fabricated via solution casting (Carta, et al., "Gas Permeability of Hexaphenylbenzene Based Polyers of Intrinsic Microporisity," *Macromolecules* (2014), 47, 8320; Du, et al., "Decarboxylation-Induced Cross-Linking of Polymers of Intrinsic Microporosity (PIMs) for Membrane Gas Separation," *Macromolecules* (2012), 45, 5134) or spin coating (Gorgojo, et al., "Ultrathin Polymer Films with Intrinsic Microporosity: Anomalous Solvent Permeation and High Flux Membranes," *Adv. Funct. Mater.* (2014), 24, 4729), which cannot be conducted at a large scale for industrial application. Some of these lab-scale membranes were also cross-linked via thermal treatment (Rong, et al., "Intrinsically Microporous Polymer Retains Porosity in Vacuum Thermolysis to Elecgtroactive Heterocarbon," *Langmuir* (2015), 31, 12300; Song, et al., "Controlled thermal oxidative crosslinking of polymers of intrinsic microporosity towards tunable molecular sieve membranes," *Nature communications* (2014), 5, 4813; Salinas, et al., "Ethylene/ethane permeation, diffusion and gas sorption properties of carbon molecular sieve membranes derived from the prototype ladder polymer of intrinsic microporosity (PIM-1)," *J. Membr. Sci.* (2016), 504, 133), UV treatment (Li, et al., U.S. Patent Publication No. 2013/0247756), or chemical crosslinking. (Du, et al., "Decarboxylation-Induced Cross-Linking of Polymers of Intrinsic Microporosity (PIMs) for Membrane Gas Separation," *Mac-* romolecules (2012), 45, 5134; Fritsch, et al., "High performance organic solvent nanofiltration membranes: Development and thorough testing of thin film composite membranes made of polymers of intrinsic microporosity (PIMs)," *J. Membr. Sci.* (2012), 401, 222). These preliminary researches explored the intrinsic separation performance of PIMs but did not contribute to the industrial fabrication and large-scale crosslinking of PIM membranes. Some reports fabricated PIM membranes via scalable blade casting (Fritsch, et al., "High performance organic solvent nanofiltration membranes: Development and thorough testing of thin film composite membranes made of polymers of intrinsic microporosity (PIMs)," *J. Membr. Sci.* (2012), 401, 222), roll-to-roll dip coating (Cook, et al., "Roll-to-roll dip coating of three different PIMs for Organic Solvent Nanofiltration," *J. Membr. Sci.* (2018), 558, 52) and dry-wet fiber spinning (Jue, et al., "Defect-free PIM-1 hollow fiber membranes," *J. Membr. Sci.* (2017), 530, 33); however, none of them had been adapted to undergo crosslinking conditions of the present invention.

Different from the aforementioned prior art, membrane fabrication techniques of the present invention are scalable and compatible with versatile crosslinking techniques, such as direct crosslinking, crosslinking via the addition of small molecules, and interfacial crosslinking.

Thus, there exists an unmet need for methods that yield highly specific, hyper-rigid cross-linked membranes that have both high membrane permeability and high selectivity along with thermal and chemical stability for gas and organic liquid separations.

SUMMARY OF THE INVENTION

Various non-limiting aspects and embodiments of the invention are described below.

In one aspect, the present invention provides a method of preparing a cross-linked polymer membrane comprising the steps of:

a) providing a first polymer comprising a first functional group selected from $-N_3$, $-C \equiv CH$, $C \equiv C-R'$, $-C \equiv N$, $-(C = O)-H$, $-SH$, $-CH = CH_2$, $-CH = CHR'$, $-NH_2$, $-NR'-NHR'$, and $-O-NHR'$ and a second polymer comprising a second functional group selected from $-N_3$, $-C \equiv CH$, $C \equiv C-R'$, $-C \equiv N$, $-(C = O)-H$, $-SH$, $-CH = CH_2$, $-CH = CHR'$, $-NH_2$, $-NR'-NHR'$, and $-O-NHR'$ wherein R' is selected from substituted or unsubstituted alkyl, substituted or unsubstituted heteroalkyl, substituted or unsubstituted aryl, substituted or unsubstituted heteroaryl, $-CN$, $-CO_2R''$, $-(C = O)-N(R'')_2$, and $-(C = O)-R''$, and R'' is independently at each occurrence selected from H, substituted or unsubstituted alkyl, substituted or unsubstituted heteroalkyl, substituted or unsubstituted aryl, and substituted or unsubstituted heteroaryl, and wherein the first functional group and the second functional group are capable of irreversibly reacting with each other to form a covalent connection;

b) fabricating the first polymer and the second polymer into a desired membrane;

c) crosslinking the fabricated membrane of step b) by reacting the first functional group and the second functional group to form the covalent connection, thus obtaining the cross-linked polymer membrane.

In one embodiment of the above method, the first polymer and the second polymer each have a chemical structure:

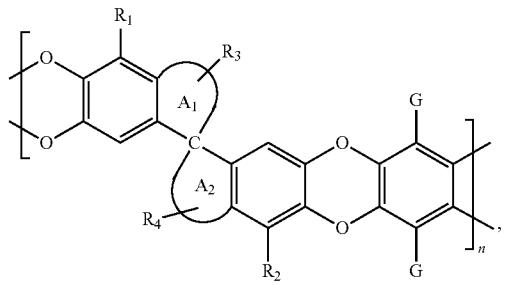

wherein: the carbon indicated by "C" denotes a spiro-carbon;

$A_1$ is selected from c and c

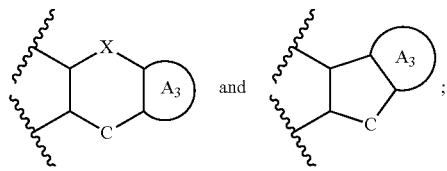

$A_2$ is

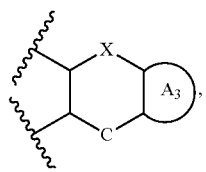

X is independently at each occurrence selected from $-CR_6$, $-O-$, $-S-$, $-N(R_6)_2$, $-C = O$, $-C = NR_6$, $-C = N-N(R_6)_2$, and $C = N-OR_6$;

$R_1$, $R_2$, $R_3$, and $R_4$ are each independently selected from H and $Y-Z$;

$R_6$ is independently at each occurrence selected from H, substituted or unsubstituted alkyl, substituted or unsubstituted heteroalkyl, substituted or unsubstituted aryl, and substituted or unsubstituted heteroaryl;

$A_3$ is a selected from substituted or unsubstituted $C_5$-$C_6$ aryl, substituted or unsubstituted $C_5$-$C_6$ heteroaryl, substituted or unsubstituted $C_5$-$C_6$ cycloalkyl and substituted or unsubstituted $C_5$-$C_6$ cyclic heterocycloalkyl;

Y is independently absent or selected from substituted or unsubstituted alkyl, substituted or unsubstituted aryl, $-NH-(C = O)-$; $=NO-C_{1-6}$ alkyl-; and $-(C = O)$-phenyl-;

Z is the functional group selected from $-N_3$, $-C \equiv CH$, $C \equiv C-R'$, $-C \equiv N$, $-(C = O)-H$, $-SH$, and $-CH = CH_2$;

R' is independently at each occurrence selected from substituted or unsubstituted alkyl, substituted or unsubstituted heteroalkyl, substituted or unsubstituted aryl, substituted or unsubstituted heteroaryl, $-CN$, $-CO_2R''$, $-(C = O)-N(R'')_2$, and $-(C = O)-R''$;

R'' is selected from H, substituted or unsubstituted alkyl, substituted or unsubstituted heteroalkyl, substituted or unsubstituted aryl, and substituted or unsubstituted heteroaryl; G is selected from Y—Z, halogen, $-CN$, substituted or unsubstituted aryl, and substituted or unsubstituted heteroaryl; and n is an integer from 5 to 100,000.

In one embodiment of the above method, the first polymer comprises the first functional group selected from —N₃ and —C≡CH, and the second polymer comprises the second functional group selected from —N₃ and —C≡CH, wherein when the first functional group is —N₃, the second functional group is —C≡CH, and when the first functional group is —C≡CH, the second functional group is —N₃.

In one embodiment of the above method, the desired membrane has a form factor selected from hollow fiber membranes, spiral wound membranes, plate-and-frame membranes, coated monoliths, tubes, and discs.

In one embodiment, the desired membrane form factor is a hollow fiber membrane.

In one embodiment of the above method, the desired membrane has a morphology selected from an integrally-skinned asymmetric morphology or a thin film composite morphology.

In one embodiment of the above method, the first polymer and the second polymer are fabricated into the desired membrane using one or more fabrication techniques selected from dry jet-wet quench solution spinning, slip casting, dip coating, blade coating, spin casting, chemical vapor deposition, interfacial polymerization, tape casting, and melt extrusion.

In one embodiment of the above method, the step b) of fabricating the first polymer and the second polymer into the desired membrane further comprises exchanging solvent and drying the fabricated membrane.

In one embodiment of the above method, the step c) of crosslinking the fabricated membrane of step b) comprises subjecting the fabricated membrane to heat, UV-visible light, a dehydrating agent, and/or a catalyst to react the first functional group and the second functional group.

In one embodiment of the above method, the step c) of crosslinking the fabricated membrane of step b) comprises submersing the fabricated membrane in a nonsolvent solution comprising a catalyst for the reaction between the first functional group and the second functional group.

In one embodiment of the above method, the step c) further comprises exchanging solvent.

In one aspect, the present invention provides a method of preparing a cross-linked polymer membrane according to Scheme 1:

Scheme 1

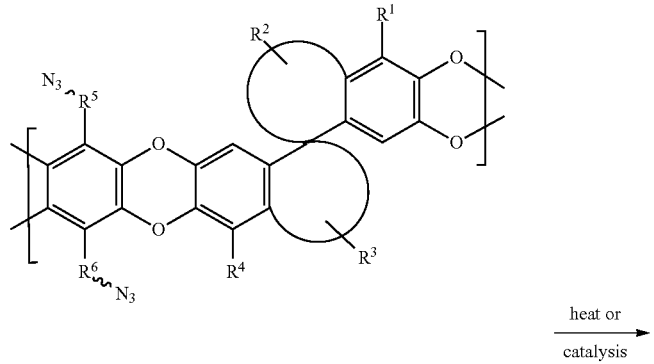

heat or catalysis

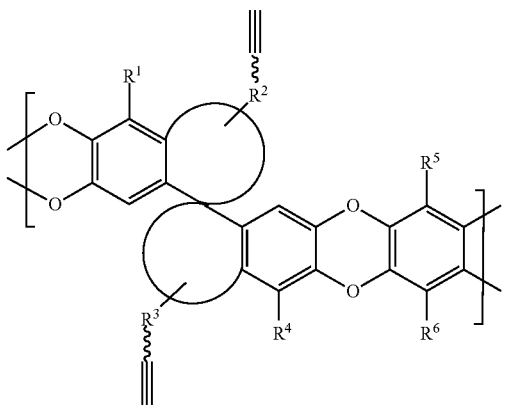

-continued

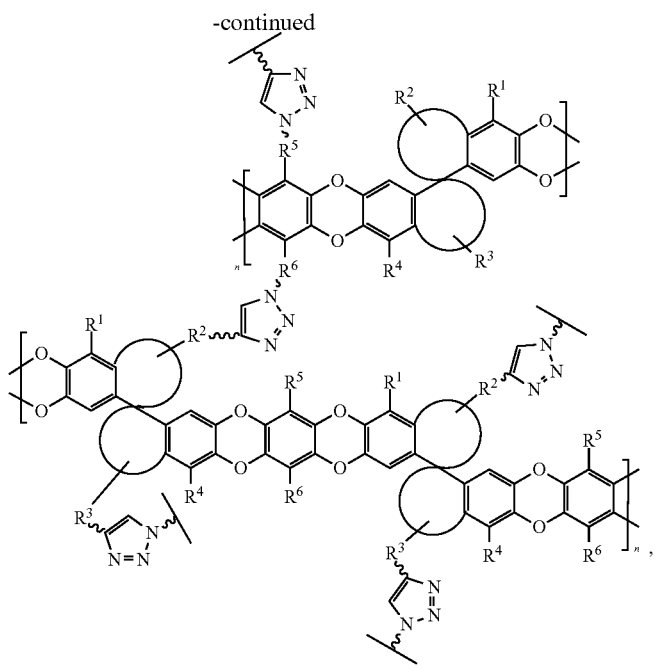

wherein $R_1$, $R_2$, $R_3$, $R_4$, $R_5$, and $R_6$ are each independently at each occurrence selected from H, substituted or unsubstituted alkyl, substituted or unsubstituted heteroalkyl, substituted or unsubstituted aryl, and substituted or unsubstituted heteroaryl, the method comprising the steps of:

a) providing a first polymer comprising a first functional group —$N_3$ and a second polymer comprising a second functional group —C≡CH, b) fabricating the first polymer and the second polymer into a desired membrane;

c) crosslinking the fabricated membrane of step b) by reacting the first functional group —$N_3$ and the second functional group —C≡CH to form a triazole connection, thus obtaining the cross-linked polymer membrane.

In one embodiment, the step c) of crosslinking the fabricated membrane of step b) comprises heating the fabricated membrane to between about room temperature and about 200° C. to react the first functional group and the second functional group.

In one embodiment, the step c) of crosslinking the fabricated membrane of step b) comprises submersing the fabricated membrane in a nonsolvent solution comprising a copper catalyst for the reaction between the first functional group —$N_3$ and the second functional group —C≡CH.

In one embodiment, the nonsolvent solution comprising a copper catalyst is a solution of copper(I) salt. Suitable Cu(I) salts include, but are not limited to, copper(I) ascorbate, copper(I) iodide, copper(I) bromide, copper(I) chloride, copper(I) acetate, $L_n$Cu(I) X, where L is selected from phosphine, amine, and/or pyridyl, n is an integer from 0 to 4, and X is selected from Cl, Br, I, OAc, and/or $BF_4$, and the combination of Cu(II) salts and sodium ascorbate, including but not limited to $CuSO_4$, $Cu(OAc)_2$, $CuBr_2$, $CuCl_2$. In one embodiment, the nonsolvent solution comprising a copper catalyst is a solution of copper (I) ascorbate.

In one aspect, the present invention provides a method of preparing a cross-linked polymer membrane according to Scheme 2:

Scheme 2

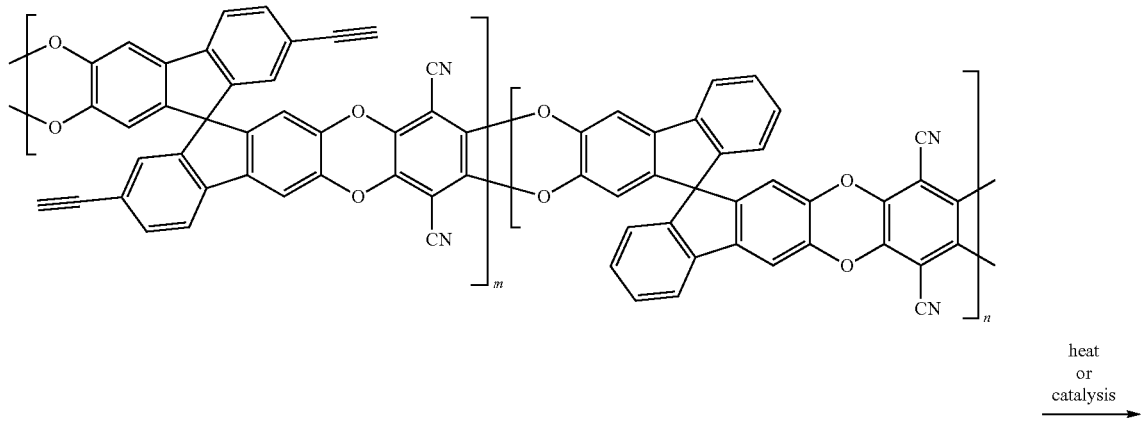

heat
or
catalysis
→

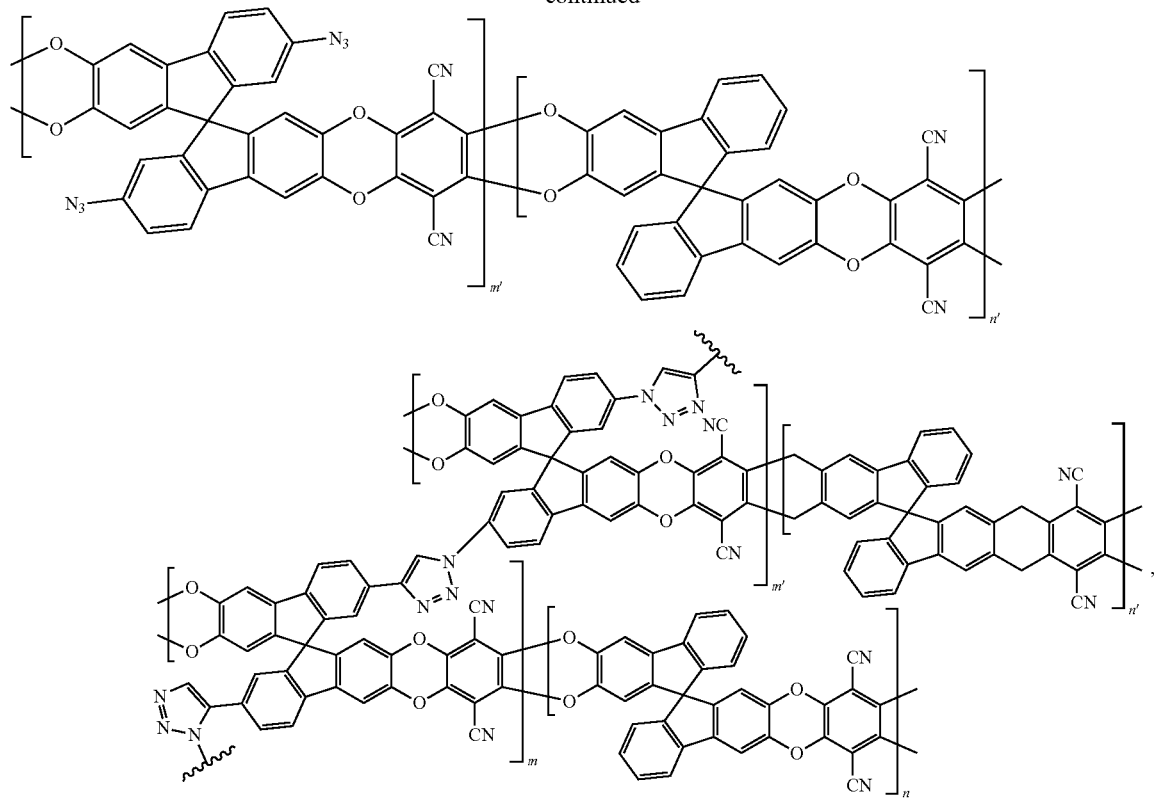

wherein n, n', m, and m' are each independently an integer from 5 to 100,000, the method comprising the steps of:

a) providing a first polymer comprising a first functional group —N₃ and a second polymer comprising a second functional group —C≡CH, b) fabricating the first polymer and the second polymer into a desired membrane;

c) crosslinking the fabricated membrane of step b) by reacting the first functional group —N₃ and the second functional group —C≡CH to form a triazole connection, thus obtaining the cross-linked polymer membrane.

In one embodiment, the step b) of fabricating the first polymer and the second polymer into a desired membrane is performed in a solvent.

In one embodiment, the step c) of crosslinking the fabricated membrane of step b) comprises submersing the fabricated membrane in a nonsolvent solution comprising a copper catalyst for the reaction between the first functional group —N₃ and the second functional group —C≡CH.

In one embodiment, the nonsolvent solution comprising a copper catalyst is a solution of copper ascorbate.

In one aspect, the present invention provides a cross-linked polymer membrane prepared according to any of the above-described methods.

In one embodiment, the membrane is insoluble in strong polar aprotic solvents. In one embodiment, the membrane is insoluble in organic solvents comprising dichloromethane, chlorobenzene, chloroform, methylene chloride, cyclohexane, hexanes, heptanes, 1,2-dichloroethane, diethyl ether, methyl t-butyl ether, carbon tetrachloride, xylenes, toluene, ethyl acetate, butyl acetate, DMF, DMAc, NMP, or DMSO, water, and/or fluorocarbons comprising perfluorohexane, perfluoroheptane, perfluorooctane, perfluorononane, 2H,3H-decafluoropentane, perfluorodecaline, perfluoromethylcyclohexane, hexafluorobenzene, octafluorotoluene, perfluoro(1,3-dimethylcyclohexane), perfluorotributylamine, or hexafluoroisopropyl methyl ether.

In another aspect, the present invention provides a method of preparing a cross-linked polymer membrane comprising the steps of:

a) providing a polymer comprising a first functional group selected from —N₃, —C≡CH, C=C—R', —C≡N, —(C=O)—H, —SH, —CH=CH₂, —CH=CHR', —NH₂, —NR'—NHR', and —O—NHR', wherein R' is selected from substituted or unsubstituted alkyl, substituted or unsubstituted heteroalkyl, substituted or unsubstituted aryl, substituted or unsubstituted heteroaryl, —CN, —CO₂R", —(C=O)—N(R")₂, and —(C=O)—R", and R" is independently at each occurrence selected from H, substituted or unsubstituted alkyl, substituted or unsubstituted heteroalkyl, substituted or unsubstituted aryl, and substituted or unsubstituted heteroaryl, and b) fabricating the polymer into a desired membrane;

c) contacting the fabricated membrane of step b) with a compound comprising a second functional group selected from —N₃, —C≡CH, C=C—R', —C≡N, —(C=O)—H, —SH, —CH=CH₂, —CH=CHR', —NH₂, —NR'—NHR', and —O—NHR', wherein the second functional group is capable of irreversibly reacting with the first functional group to form a covalent connection;

d) crosslinking the fabricated membrane of step b) with the compound of step c) by reacting the first functional group and the second functional group to form the covalent connection, thus obtaining the cross-linked polymer membrane.

In one embodiment of the above method, the polymer comprising the first functional group has the following chemical structure:

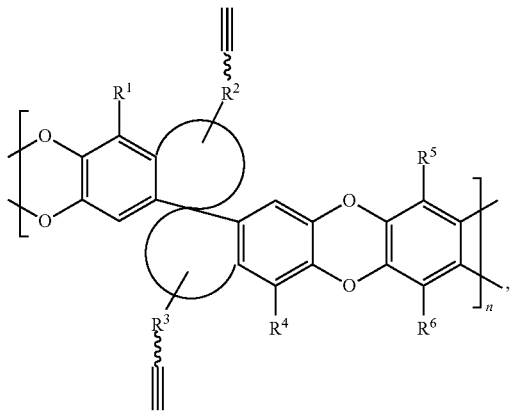

wherein $R_1$, $R_2$, $R_3$, $R_4$, $R_5$, and $R_6$ are each independently at each occurrence selected from H, substituted or unsubstituted alkyl, substituted or unsubstituted heteroalkyl, substituted or unsubstituted aryl, and substituted or unsubstituted heteroaryl, and n is an integer from 5 to 100,000.

In one embodiment of the above method, the second functional group is —$N_3$.

In one embodiment of the above method, the compound comprising the second functional group has a structure according to formula:

wherein R is selected from a substituted or unsubstituted alkyl, substituted or unsubstituted heteroalkyl, substituted or unsubstituted aryl, and substituted or unsubstituted heteroaryl.

In one embodiment of the above method, the step c) of contacting the fabricated membrane of step b) with a compound comprising the second functional group is performed by submersing the fabricated membrane in a solution of the compound comprising the second functional group.

In one aspect, the present invention provides a method of preparing a cross-linked polymer membrane according to Scheme 4:

Scheme 4

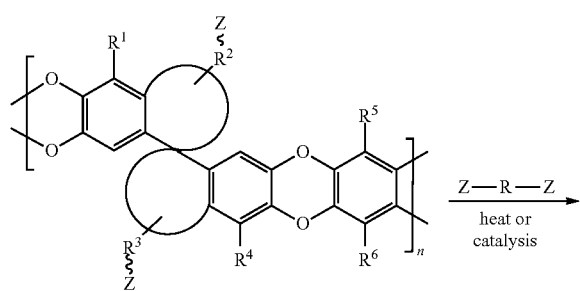

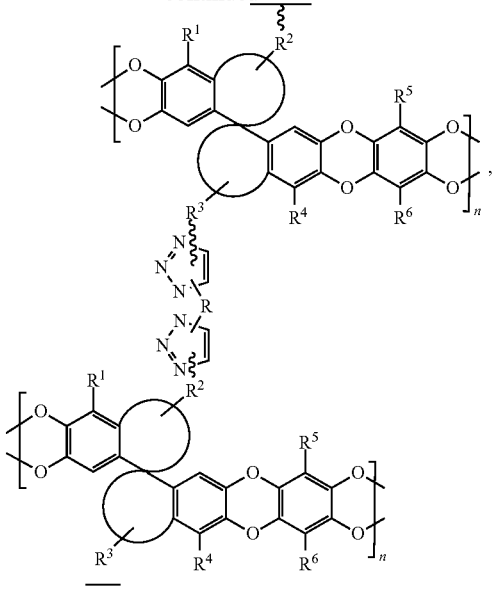

wherein Z is a group selected from —$N_3$ and —C≡CH,

R is selected from a substituted or unsubstituted alkyl, substituted or unsubstituted heteroalkyl, substituted or unsubstituted aryl, and substituted or unsubstituted heteroaryl, and wherein $R_1$, $R_2$, $R_3$, $R_4$, $R_5$, and $R_6$ are each independently at each occurrence selected from H, substituted or unsubstituted alkyl, substituted or unsubstituted heteroalkyl, substituted or unsubstituted aryl, and substituted or unsubstituted heteroaryl, and n is an integer from 5 to 100,000 the method comprising the steps of:

a) providing a polymer comprising a functional group Z selected from —$N_3$ and —C≡CH, b) fabricating the polymer into a desired membrane;

c) contacting the fabricated membrane of step b) with a compound comprising a functional group Z selected from —$N_3$ and —C≡CH, wherein if the polymer functional group of step (a) is —$N_3$, then the compound functional group is —C≡CH, and if the polymer functional group of step (a) is —C≡CH, then the compound functional group is —$N_3$;

d) crosslinking the fabricated membrane of step b) with the compound of step c) comprising the functional group by reacting the functional group —C≡CH with the functional group —$N_3$ to form a triazole connection, thus obtaining the cross-linked polymer membrane.

In one embodiment of the above method, the step d) of crosslinking the fabricated membrane of step b) with the compound of step c) comprises heating to from about room temperature to about 200° C.

In one embodiment of the above method, the step d) of crosslinking the fabricated membrane of step b) with the compound of step c) comprises submersing the fabricated membrane in a solution comprising the compound of step c) and a catalyst for initiating the reaction between the functional group —C≡CH and the functional group —$N_3$.

In one embodiment of the above method, the catalyst is a copper catalyst.

In one embodiment of the above method, the copper catalyst is copper ascorbate.

In one embodiment, the method is according to Scheme 5:

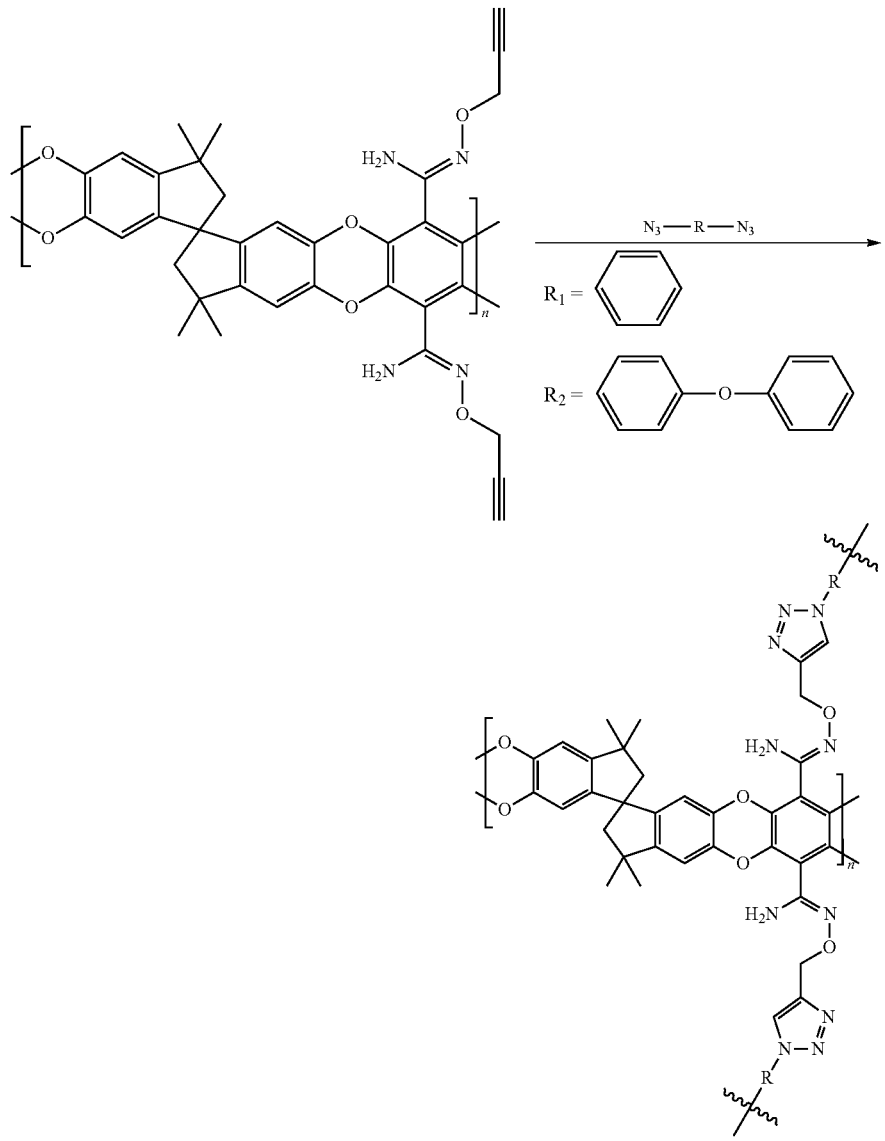

wherein n is an integer from 5 to 100,000, and

R is selected from a substituted or unsubstituted alkyl, substituted or unsubstituted heteroalkyl, substituted or unsubstituted aryl, and substituted or unsubstituted heteroaryl. In one embodiment, R is selected from $R_1$ and $R_2$, wherein $R_1$ is phenyl and $R_2$ is diphenyl ether.

In another aspect, the present invention provides a cross-linked polymer membrane prepared according to any of the methods described above.

In one embodiment, the cross-linked polymer membrane is insoluble in strong polar aprotic solvents. In one embodiment, the membrane is insoluble in organic solvents comprising dichloromethane, chlorobenzene, chloroform, methylene chloride, cyclohexane, hexanes, heptanes, 1,2-dichloroethane, diethyl ether, methyl t-butyl ether, carbon tetrachloride, xylenes, toluene, ethyl acetate, butyl acetate, DMF, DMAc, NMP, or DMSO, water, and/or fluorocarbons comprising perfluorohexane, perfluoroheptane, perfluorooctane, perfluorononane, 2H,3H-decafluoropentane, perfluorodecaline, perfluoromethylcyclohexane, hexafluorobenzene, octafluorotoluene, perfluoro(1,3-dimethylcyclohexane), perfluorotributylamine, or hexafluoroisopropyl methyl ether.

In another aspect, the present invention provides a method of preparing a cross-linked polymer membrane at an interface of a first solvent and a second solvent, wherein the first solvent is immiscible with the second solvent, the method comprising the steps of:

a) providing a polymer comprising a first functional group selected from —$N_3$, —C≡CH, C≡C—R', —C≡N, —(C=O)—H, —SH, —CH=$CH_2$, —CH=CHR', —$NH_2$, —NR'—NHR', and —O—NHR', wherein R' is selected from substituted or unsubstituted alkyl, substituted or unsubstituted heteroalkyl, substituted or unsubstituted aryl, substituted or unsubstituted heteroaryl, —CN, —$CO_2$R", —(C=O)—N(R")$_2$, and —(C=O)—R", and R" is independently at each occurrence selected from H, substituted or unsubstituted alkyl, substituted or unsubstituted heteroalkyl, substituted or unsubstituted aryl, and substituted or unsubstituted heteroaryl;

b) fabricating the polymer into a desired membrane;

c) contacting the fabricated membrane of step b) with a compound comprising a second functional group selected from —$N_3$, —C≡CH, C≡C—R', —C≡N, —(C=O)—H, —SH, —CH=$CH_2$, —CH=CHR', —$NH_2$, —NR'—NHR', and —O—NHR', wherein the second functional group is capable of irreversibly reacting with the first functional group to form a covalent connection, by dissolving the fabricated membrane and the compound in the first solvent;

d) combining the first solvent comprising fabricated membrane and the compound and a second solvent comprising a catalyst for initiating a reaction between the first functional group and the second functional group, e) crosslinking the fabricated membrane of step b) with the compound of step c) by reacting the first functional group and the second functional group to form the covalent connection, wherein the crosslinking reaction between the first functional group and the second functional group occurs at the interface of the first solvent and the second solvent, thereby forming the cross-linked polymer membrane at the interface of the first solvent and the second solvent.

In one embodiment, the first functional group is selected from —$N_3$ and —C≡CH, and the second functional group is selected from —$N_3$ and —C≡CH, wherein when the first functional group is —$N_3$, the second functional group is —C≡CH, and when the first functional group is —C≡CH, the second functional group is —$N_3$.

In one embodiment, the catalyst is a copper catalyst. In one embodiment, the catalyst is Cu(I) ascorbate.

In one embodiment, the first solvent is an organic solvent and the second solvent is selected from water and a fluorocarbon solvent, or wherein the first solvent is water and the second solvent is selected from an organic solvent and a fluorocarbon solvent; or when the first solvent is a fluorocarbon solvent and the second solvent is selected from an organic solvent and water.

In one embodiment, the first solvent is an organic solvent comprising dichloromethane, chlorobenzene, chloroform, methylene chloride, cyclohexane, hexanes, heptanes, 1,2-dichloroethane, diethyl ether, methyl t-butyl ether, carbon tetrachloride, xylenes, toluene, ethyl acetate, or butyl acetate, and the second solvent is selected from water and a fluorocarbon comprising perfluorohexane, perfluoroheptane, perfluorooctane, perfluorononane, 2H,3H-decafluoropentane, perfluorodecaline, perfluoromethylcyclohexane, hexafluorobenzene, octafluorotoluene, perfluoro(1,3-dimethylcyclohexane), perfluorotributylamine, or hexafluoroisopropyl methyl ether.

In one embodiment, the first solvent is water and the second solvent is selected from an organic solvent comprising dichloromethane, chlorobenzene, chloroform, methylene chloride, cyclohexane, hexanes, heptanes, 1,2-dichloroethane, diethyl ether, methyl t-butyl ether, carbon tetrachloride, xylenes, toluene, ethyl acetate, or butyl acetate, and a fluorocarbon solvent comprising perfluorohexane, perfluoroheptane, perfluorooctane, perfluorononane, 2H,3H-decafluoropentane, perfluorodecaline, perfluoromethylcyclohexane, hexafluorobenzene, octafluorotoluene, perfluoro(1,3-dimethylcyclohexane), perfluorotributylamine, or hexafluoroisopropyl methyl ether.

In one embodiment, the first solvent is a fluorocarbon solvent comprising perfluorohexane, perfluoroheptane, perfluorooctane, perfluorononane, 2H,3H-decafluoropentane, perfluorodecaline, perfluoromethylcyclohexane, hexafluorobenzene, octafluorotoluene, perfluoro(1,3-dimethylcyclohexane), perfluorotributylamine, or hexafluoroisopropyl methyl ether, and the second solvent is selected from water and an organic solvent comprising dichloromethane, chlorobenzene, chloroform, methylene chloride, cyclohexane, hexanes, heptanes, 1,2-dichloroethane, diethyl ether, methyl t-butyl ether, carbon tetrachloride, xylenes, toluene, ethyl acetate, or butyl acetate.

In another aspect, the present invention provides a method of preparing a cross-linked polymer membrane on solid support comprising the steps of:

a) providing a polymer comprising a first functional group selected from —$N_3$, —C≡CH, C≡C—R', —CN, —(C=O)—H, —SH, —CH=$CH_2$, —CH=CHR', —$NH_2$, —NR'—NHR', and —O—NHR', wherein R' is selected from substituted or unsubstituted alkyl, substituted or unsubstituted heteroalkyl, substituted or unsubstituted aryl, substituted or unsubstituted heteroaryl, —CN, —$CO_2R"$, —(C=O)—N(R")$_2$, and —(C=O)—R", and R" is independently at each occurrence selected from H, substituted or unsubstituted alkyl, substituted or unsubstituted heteroalkyl, substituted or unsubstituted aryl, and substituted or unsubstituted heteroaryl;

b) fabricating the polymer into a desired membrane by coating the solid support with the polymer;

c) contacting the solid support with the fabricated membrane of step b) with a compound comprising a second functional group selected from —$N_3$, —C≡CH, C≡C—R', —C≡N, —(C=O)—H, —SH, —CH=$CH_2$, —CH=CHR', —$NH_2$, —NR'—NHR', and —O—NHR', wherein the second functional group is capable of irreversibly reacting with the first functional group to form a covalent connection;

d) crosslinking the fabricated membrane of step b) with the compound of step c) by reacting the first functional group and the second functional group to form the covalent connection, thus obtaining the cross-linked polymer membrane of solid support.

In one embodiment, the solid support with the fabricated membrane of step b) is submersed in a solution comprising a catalyst for initiating the reaction of the first functional group with the second functional group prior to the step c).

In one embodiment, the solution comprising the catalyst is an aqueous solution and the catalyst is a water-soluble copper catalyst.

In one embodiment, the step c) of contacting the solid support with the fabricated membrane of step b) with the compound comprising the second functional group is performed by submersing the solid support with the fabricated membrane in a solution comprising the compound comprising the second functional group.

In one embodiment, the compound comprising the second functional group is dissolved in an organic solvent dichloromethane, chlorobenzene, chloroform, methylene chloride, cyclohexane, hexanes, heptanes, 1,2-dichloroethane, diethyl ether, methyl t-butyl ether, carbon tetrachloride, xylenes, toluene, ethyl acetate, butyl acetate, tetrahydrofuran, tetrahydropyran, dimethyl formamide, NMP, acetone, ethanol, methanol, and toluene.

In one embodiment, the coating of the solid support with the polymer is performed by spin coating.

In one embodiment, the solid support is selected from a ceramic surface, a zeolite surface, and a polymer surface.

In another aspect, the present invention provides a method of preparing a cross-linked polymer membrane on solid copper support comprising the steps of:

a) providing a polymer comprising a first functional group selected from —N₃, —C≡CH, C≡C—R', —CN, —(C═O)—H, —SH, —CH═CH₂, —CH═CHR', —NH₂, —NR'—NHR', and —O—NHR', wherein R' is selected from substituted or unsubstituted alkyl, substituted or unsubstituted heteroalkyl, substituted or unsubstituted aryl, substituted or unsubstituted heteroaryl, —CN, —CO₂R'', —(C═O)—N(R'')₂, and —(C═O)—R'', and R'' is independently at each occurrence selected from H, substituted or unsubstituted alkyl, substituted or unsubstituted heteroalkyl, substituted or unsubstituted aryl, and substituted or unsubstituted heteroaryl;

b) fabricating the polymer into a desired membrane by coating the copper support with the polymer;

c) contacting the copper support with the fabricated membrane of step b) with a compound comprising a second functional group selected from —N₃, —C≡CH, C≡C—R', —C≡N, —(C═O)—H, —SH, —CH═CH₂, —CH═CHR', —NH₂, —NR'—NHR', and —O—NHR', wherein the second functional group is capable of irreversibly reacting with the first functional group to form a covalent connection;

d) crosslinking the fabricated membrane of step b) with the compound of step c) by reacting the first functional group and the second functional group to form the covalent connection, thus obtaining the cross-linked polymer membrane of solid copper support.

In yet another aspect, the present invention provides a method of preparing a cross-linked polymer membrane on solid copper support comprising the steps of:

a) providing a first polymer comprising a first functional group selected from —N₃, —C≡CH, C≡C—R', —C≡N, —(C═O)—H, —SH, —CH═CH₂, —CH═CHR', —NH₂, —NR'—NHR', and —O—NHR', and a second polymer comprising a second functional group selected from —N₃, —C≡CH, C≡C—R', —C≡N, —(C═O)—H, —SH, —CH═CH₂, —CH═CHR', —NH₂, —NR'—NHR', and —O—NHR', wherein the second functional group is capable of irreversibly reacting with the first functional group to form a covalent connection, wherein R' is selected from substituted or unsubstituted alkyl, substituted or unsubstituted heteroalkyl, substituted or unsubstituted aryl, substituted or unsubstituted heteroaryl, —CN, —CO₂R'', —(C═O)—N(R'')₂, and —(C═O)—R'', and R'' is independently at each occurrence selected from H, substituted or unsubstituted alkyl, substituted or unsubstituted heteroalkyl, substituted or unsubstituted aryl, and substituted or unsubstituted heteroaryl;

b) coating the copper support with the first polymer and the second polymer;

c) crosslinking the first polymer and the second polymer by reacting the first functional group and the second functional group to form the covalent connection on solid copper support, thus obtaining the cross-linked polymer membrane of solid copper support.

In one embodiment, the first and the second polymer may be comprised in a single polymer blend comprising the first functional group and the second functional group.

In one embodiment, the crosslinking reaction is initiated by heating the copper support coated with the first polymer and the second polymer.

In yet another aspect, the present invention provides a method of preparing a cross-linked polymer membrane covalently attached to a solid support comprising the steps of:

a) covalently attaching to the solid support a compound comprising a first functional group selected from —N₃, —C≡CH, C≡C—R', —C≡N, —(C═O)—H, —SH, —CH═CH₂, —CH═CHR', —NH₂, —NR'—NHR', and —O—NHR', wherein R' is selected from substituted or unsubstituted alkyl, substituted or unsubstituted heteroalkyl, substituted or unsubstituted aryl, substituted or unsubstituted heteroaryl, —CN, —CO₂R'', —(C═O)—N(R'')₂, and —(C═O)—R'', and R'' is independently at each occurrence selected from H, substituted or unsubstituted alkyl, substituted or unsubstituted heteroalkyl, substituted or unsubstituted aryl, and substituted or unsubstituted heteroaryl;

b) fabricating a polymer membrane on the functionalized solid support with a polymer comprising a second functional group selected from —N₃, —C≡CH, C≡C—R', —C≡N, —(C═O)—H, —SH, —CH═CH₂, —CH═CHR', —NH₂, —NR'—NHR', and —O—NHR', wherein the second functional group is capable of irreversibly reacting with the first functional group to form a covalent connection, c) reacting the first functional group and the second functional group to form the cross-linked polymer membrane, thus obtaining the cross-linked polymer membrane covalently attached to the solid support.

In one embodiment, the reaction of step c) is initiated by heating the polymer-coated functionalized support.

In one embodiment, the reaction of step c) is initiated by submerging the polymer-coated functionalized support in a solution comprising a catalyst. In one embodiment, the catalyst is a copper catalyst.

In one aspect, the present invention provides a cross-linked polymer membrane prepared according to any of the method described above.

In one embodiment, the cross-linked polymer membrane is insoluble in strong polar aprotic solvents.

In one embodiment, the cross-linked polymer membrane is insoluble in organic solvents comprising dichloromethane, chlorobenzene, chloroform, methylene chloride, cyclohexane, hexanes, heptanes, 1,2-dichloroethane, diethyl ether, methyl t-butyl ether, carbon tetrachloride, xylenes, toluene, ethyl acetate, butyl acetate, DMF, DMAc, NMP, or DMSO, water, and/or fluorocarbons comprising perfluorohexane, perfluoroheptane, perfluorooctane, perfluorononane, 2H,3H-decafluoropentane, perfluorodecaline, perfluoromethylcyclohexane, hexafluorobenzene, octafluorotoluene, perfluoro(1,3-dimethylcyclohexane), perfluorotributylamine, or hexafluoroisopropyl methyl ether.

In one embodiment, the cross-linked polymer membrane has a molecular weight cut-off of about 150 to about 2000 Daltons, or about 150 to about 1500 Daltons, or about 150 to about 600 Daltons.

In one embodiment, the cross-linked polymer membrane has a pore size of about 0.5 nm to about 2 nm.

In another aspect, the present invention provides a liquid separation system comprising the cross-linked polymer membrane as described above.

In one embodiment, the liquid separation system of the invention is suitable for separation of crude oil.

In one embodiment, the liquid separation system of the invention is suitable for separation of whole crude oil and/or crude oil fractions.

In one embodiment, the liquid separation system of the invention is capable of separating a naphtha and/or a kerosene fraction of whole crude oil.

In another aspect, the present invention provides a method of separating two or more liquids using a cross-linked polymer membrane as described above.

In yet another aspect, the present invention provides a method of removing a homogenous catalyst from an organic solvent using a cross-linked polymer membrane as described above.

In one embodiment, the homogenous catalyst is selected from rhodium, nickel, and cobalt.

These and other aspects of the present invention will become apparent to those skilled in the art after a reading of the following detailed description of the invention, including the appended claims.

BRIEF DESCRIPTION OF THE DRAWINGS

FIG. 1A is a generalized schematic for direct crosslinking of complementary PIM polymers. FIG. 1B depicts one specific non-limiting embodiment of direct crosslinking utilizing spirobifluorene PIMs.

FIG. 3A is a generalized method for PIM-1 membrane crosslinking via nitrile conversion to tetrazoles and subsequent addition of small molecules. FIG. 3B shows exemplary cross linked membranes of the invention showing similar $CO_2/CH_4$ selectivity as PIM-1 with a loss in permeability for $CO_2$ possibly due to the cross linking. The cross-linked PIM membranes according to the present disclosure are significantly more resistant to plasticization than PIM-1, showing lower swelling in typical organic solvents despite having higher uptake (FIG. 3C).

FIG. 4 depicts interfacial cross-linking of PIM-1 polymer functionalized with alkyne side chains with a di-functional azide using water soluble Cu (I) catalyst. FIG. 4B(1) is a photograph of the initial reaction after layers were combined, FIG. 4B(2) is a photograph taken 24 hours after reaction started, FIG. 4B(3) is a photograph of the inversion of the test tube, and FIG. 4B(4) is a photograph of the membrane in THF.

FIG. 5A depicts support showing large cracks and uneven coloration, FIG. 5B depicts support under UV light, FIG. 5C depicts SEM imaging of support.

FIG. 7A depicts an initial interfacial polymerization with a water soluble di-functional azide and organic soluble tri-functional alkyne. FIG. 7B, left to right: initial reaction after layers were combined, 24 hours after reaction started, removal of precipitate at interface and submersion in THF, and dried solid from interface.

FIG. 8A depicts an interfacial polymerized to form a thin film membrane using a water soluble diazide. FIG. 8B, left to right: initial reaction after layers were combined, 24 hours after reaction started, and removal of precipitate at interface and submersion in THF.

FIG. 9A depicts interfacial polymerization to form a thin film membrane using an organic soluble long chain diazide and organic soluble trialkyne with a water soluble Cu(I) catalyst. FIG. 9B, left to right: (1) initial reaction after layers were combined, (2) 24 hours after reaction started, (3) removal of the organic layer, (4) inversion of reaction vessel, and (5) precipitate submersion in THF.

FIG. 10A depicts a generalized method for crosslinking alkyne and azide containing PIM films directly onto copper substrates. FIG. 10B provides one specific non-limiting example of crosslinking PIM film onto a CuO hollow fiber.

FIGS. 20(A and B) show general depictions of the cross-linking process with small-molecule cross-linkers. All molecules are merely representative and not encompassing the entire range of linkers; n=5-100.

FIG. 22A is a photograph of a free-standing polymer film; FIG. 22B is a photograph showing film defects; and FIG. 22C shows film cracking.

FIG. 24A is a permeance and rejection time plot of PIM-BADAS-1/PAN membranes with TIPB as solute in toluene at a feed flow rate of 30 mL/min; FIG. 24B is a plot of rejection vs. permeance of different PIMs spin coated on Matrimid® with TIPB (204.35 Da) as the solute in toluene. Data is compared against results for PIM TFCs by Cook et al. with α-methylstyrene dimer (236.35 Da) as solute in toluene.

FIG. 25A and FIG. 25B are permeance and rejection over time plots, respectively, of TIPB and mesitylene for PIM-BADAS-1 on Matrimid®. Feed solution contained a 7-component aromatic hydrocarbon mixture with toluene as the primary solvent.

DETAILED DESCRIPTION

Figure 2:
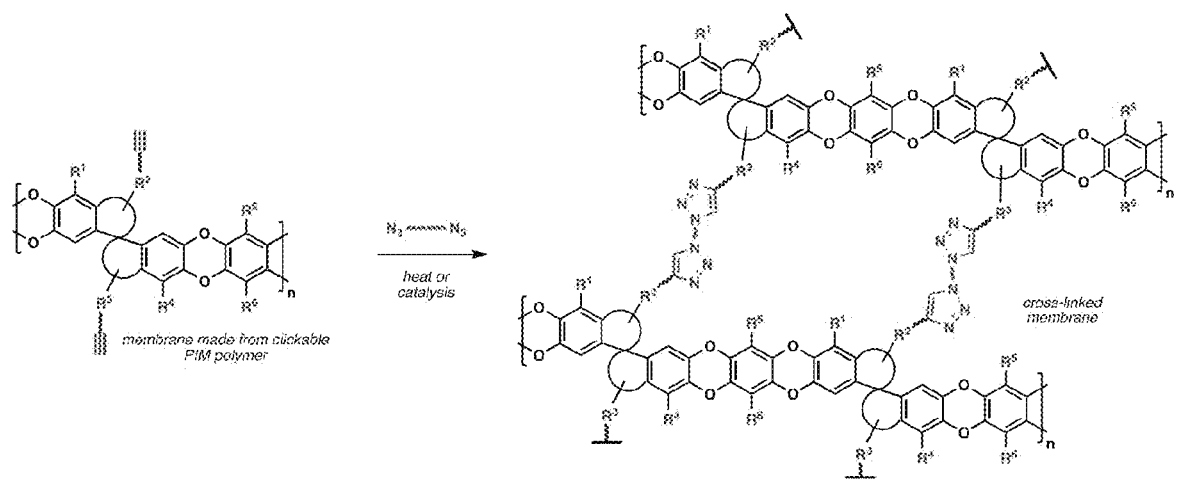
FIG. 2A is a generalized method for membrane crosslinking via addition of small molecules.
FIG. 2B depicts one specific non-limiting embodiment of membrane crosslinking via addition of small molecules utilizing PIM-1 as a starting point.
FIG. 2C is a photograph of before and after the reaction according to FIG. 2B.
Figure 2A:
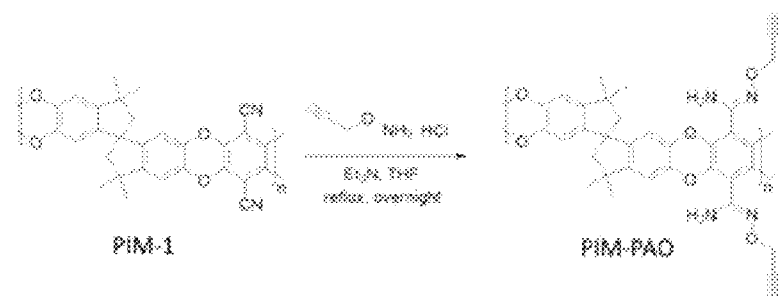
Figure 2A:
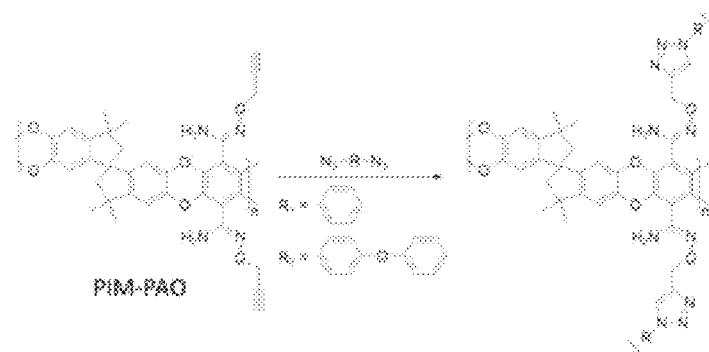
Figure 2A:
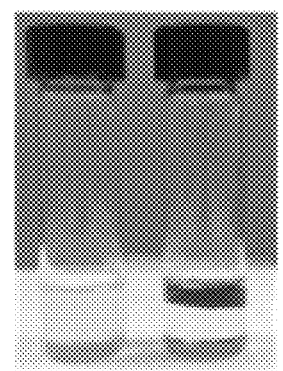

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Therefore, specific structural and functional details disclosed herein are not to be interpreted as limiting, but merely as a representative basis for teaching one skilled in the art to variously employ the present invention.

Unless defined otherwise, all technical and scientific terms used herein have the same meaning as commonly understood by one of ordinary skill in the art to which this invention belongs.

As used in this specification and the appended claims, the singular forms "a", "an", and "the" include plural references unless the context clearly dictates otherwise. Thus, for example, a reference to "a method" includes one or more methods, and/or steps of the type described herein and/or which will become apparent to those persons skilled in the art upon reading this disclosure.

Ranges can be expressed herein as from "about" or "approximately" one particular value and/or to "about" or "approximately" another particular value. When such a range is expressed, another embodiment includes from the one particular value and/or to the other particular value.

By "comprising" or "containing" or "including" is meant that at least the named compound, element, particle, or method step is present in the composition or article or method, but does not exclude the presence of other compounds, materials, particles, or method steps, even if the other such compounds, material, particles, or method steps have the same function as what is named.

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon, bicyclic hydrocarbon, or tricyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-30 aliphatic carbon atoms. In some embodiments, aliphatic groups contain 1-20 aliphatic carbon atoms. In other embodiments, aliphatic groups contain 1-10 aliphatic carbon atoms. In still other embodiments, aliphatic groups contain 1-6 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "cycloaliphatic," as used herein, refers to saturated or partially unsaturated cyclic aliphatic monocyclic, bicyclic, or polycyclic ring systems, as described herein, having from 3 to 14 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, the cycloalkyl has 3-6 carbons. The terms "cycloaliphatic," may also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic group is bicyclic. In some embodiments, a 'carbocyclic group is tricyclic. In some embodiments, a carbocyclic group is polycyclic. In some embodiments, "cycloaliphatic" (or "carbocycle" or "cycloalkyl") refers to a monocyclic $C_3$-$C_6$ hydrocarbon, or a $C_8$-$C_{10}$ bicyclic hydrocarbon that is completely saturated or that contains one or more units of unsaturation, but which is not aromatic, that has a single point of attachment to the rest of the molecule, or a $C_9$-$C_{16}$ tricyclic hydrocarbon that is completely saturated or that contains one or more units of unsaturation, but which is not aromatic, that has a single point of attachment to the rest of the molecule.

As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10 carbon atoms, or about 1 to 6 carbon atoms. In some embodiments, a cycloalkyl ring has from about 3-10 carbon atoms in their ring structure where such rings are monocyclic or bicyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

As used herein, the term "alkenyl" refers to an alkyl group, as defined herein, having one or more double bonds.

As used herein, the term "alkynyl" refers to an alkyl group, as defined herein, having one or more triple bonds.

The term "heteroalkyl" is given its ordinary meaning in the art and refers to alkyl groups as described herein in which one or more carbon atoms is replaced with a heteroatom (e.g., oxygen, nitrogen, sulfur, and the like). Examples of heteroalkyl groups include, but are not limited to, alkoxy, poly(ethylene glycol)-, alkyl-substituted amino, tetrahydrofuranyl, piperidinyl, morpholinyl, etc.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, binaphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone of as part of a larger moiety, e.g., "heteroaralkyl," or "heteroaralkoxy," refer to groups having 5 to 10 ring atoms (i.e., monocyclic or bicyclic), in some embodiments 5, 6, 9, or 10 ring atoms. In some embodiments, such rings have 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic, bicyclic, tricyclic, tetracyclic, and/or otherwise polycyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen.

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be monocyclic, bicyclic, tricyclic, tetracyclic, and/or otherwise polycyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring.

The term "unsaturated," as used herein, means that a moiety has one or more units of unsaturation.

The term "halogen" means F, Cl, Br, or I; the term "halide" refers to a halogen radical or substituent, namely —F, —Cl, —Br, or —I.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

The term "spiro compound" refers to a chemical compound that presents a twisted structure of two or more rings, in which at least 2 rings are linked together by one common atom, e.g., a carbon atom. When the common atom is located in the center of the compound, the compound is referred to as a "spirocentric compound." The common atom that connects the two or more rings is referred to as the "spiroatom." When such common atom is a carbon atom, it is referred to as the "spiro-carbon."

As used herein, ring fusions, including without limitation aliphatic and aromatic ring fusions, are represented by wavy bond connections, such as shown below.

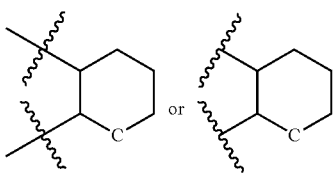 [SMILES: *C1CCCCC1* ; *C1CCCCC1*]

The connecting bonds may themselves be single or multiple (e.g., aromatic, double, triple, etc.) bonds. By way of non-limiting example, a spirocentric compound containing a spiro-carbon linking two bicyclic rings is shown below.

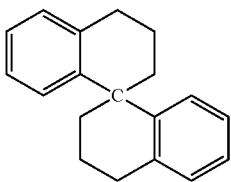 [SMILES: c1ccc2c(c1)CCCC21CCCc2ccccc21]

This compound may be schematically represented as follows:

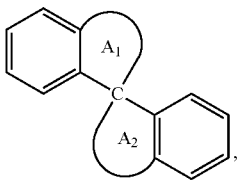

wherein $A_1$ and $A_2$ are each

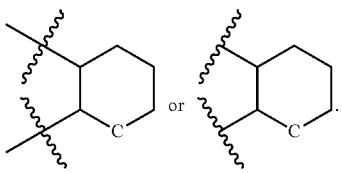 [SMILES: *C1CCCCC1* ; *C1CCCCC1*]

In the above example, the connecting bonds, represented by wavy bond connections, are aromatic bonds.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{11}C$- or $^{13}C$- or $^{14}C$-enriched carbon are within the scope of this invention.

The term "molecular weight cut-off" or "MWCO" is a characterization method to describe the pore size distribution and retention capabilities of membranes. It is defined as the lowest molecular weight (in Daltons) at which greater than 90% of a solute with a known molecular weight is retained by the membrane. Typically, the weight average molecular weight of the solute is used to determine MWCO. Dextran, polyethylene glycol, polystyrene and dye molecules of various molecular weights are commonly used to obtain the MWCO of membranes. For example, a membrane that can retain solutes with molecular weights of 10,000+ Daltons has a molecular weight cut-off of 10,000. ASTM E1343-90 describes a standard test method for MWCO evaluation of flat sheet ultrafiltration membranes.

It is also to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified.

Click chemistry reactions in general, and copper-catalyzed azide-alkyne cycloaddition reaction (CuAAC) specifically, and are known as fast, high conversion, specific and orthogonal to common chemical conversions. The present invention describes how CuAAC chemistry may be used to cross-link polymers and membranes for separation of gases and liquids. It has been surprisingly discovered that the use of click reactions in PIM crosslinking is efficient and well-controlled in a variety of conditions and configurations.

Other, less effective methodologies have been used to cross-link PIMs for the purposes of membrane preparations, e.g., nitrene-based and oxidative methodologies. Additionally, the covalent attachment of membranes to solid supports such as ceramic and alkyne-functionalized polyimides is also novel. Additionally, it has been surprisingly discovered that CuAAC reaction affords membrane polymerization at the interface of two liquid layers outside of microemulsions to form polymer nanoparticles (Roux, et al., "Facile and Rapid Access to Glyconanocapsules by CuAAC Interfacial Polyaddition in Miniemulsion Conditions," *ACS Macro Lett.* (2012), 1, 1074-1078).

I. Direct Crosslinking

In one aspect, the present invention provides a method of preparing a cross-linked polymer membrane by direct crosslinking.

In one aspect, the present invention provides a method of preparing a cross-linked polymer membrane comprising the steps of:

a) providing a first polymer comprising a first functional group selected from —$N_3$, —C≡CH, C≡C—R', —C≡N, —(C=O)—H, —SH, —CH=$CH_2$, —CH=CHR', —$NH_2$, —NR'—NHR', and —O—NHR' and a second polymer comprising a second functional group selected from —$N_3$, —C≡CH, C≡C—R', —C≡N, —(C=O)—H, —SH, —CH=$CH_2$, —CH=CHR', —$NH_2$, —NR'—NHR', and —O—NHR' wherein R' is selected from substituted or unsubstituted alkyl, substituted or unsubstituted heteroalkyl, substituted or unsubstituted aryl, substituted or unsubstituted heteroaryl, —CN, —$CO_2R"$, —(C=O)—N(R")$_2$, and —(C=O)—R", and R" is independently at each occurrence selected from H, substituted or unsubstituted alkyl, substituted or unsubstituted heteroalkyl, substituted or unsubstituted aryl, and substituted or unsubstituted heteroaryl, and wherein the first functional group and the second functional group are capable of irreversibly reacting with each other to form a covalent connection;

b) fabricating the first polymer and the second polymer into a desired membrane;

c) crosslinking the fabricated membrane of step b) by reacting the first functional group and the second functional group to form the covalent connection, thus obtaining the cross-linked polymer membrane.

In one embodiment, polymers comprising complementary functional groups (e.g., azide and alkyne) are first fabricated into the desired membrane.

In one embodiment, the desired membrane may have a form factor selected from hollow fiber membranes, spiral wound membranes, plate-and-frame membranes, coated monoliths, tubes, and discs. In one embodiment, the desired membrane may be a hollow fiber membrane.

In one embodiment, the desired membrane may have a morphology selected from an integrally-skinned asymmetric morphology or a thin film composite morphology.

In one embodiment, the first polymer and the second polymer are fabricated into the desired membrane using one or more fabrication techniques selected from dry jet-wet quench solution spinning, slip casting, dip coating, blade coating, spin casting, chemical vapor deposition, interfacial polymerization, tape casting, and melt extrusion.

In one embodiment, the step b) of fabricating the first polymer and the second polymer into the desired membrane further comprises exchanging solvent and drying the fabricated membrane.

In one embodiment, the step c) of crosslinking the fabricated membrane of step b) comprises subjecting the fabricated membrane to heat, UV-visible light, a dehydrating agent, and/or a catalyst to react the first functional group and the second functional group.

In one embodiment, the membranes may be heated to the point that the reaction between complementary functional groups begins, thus crosslinking the polymer in the dry state.

In one embodiment, the membranes may be heated to a temperature between about room temperature and about 400° C., preferably about room temperature and about 200° C., or between about 200° C. and about 400° C. to react the complementary functional groups, thus crosslinking the polymer in the dry state.

In one embodiment, the step c) of crosslinking the fabricated membrane of step b) comprises submersing the fabricated membrane in a nonsolvent solution comprising a catalyst for the reaction between the first functional group and the second functional group. This step can be combined with standard solvent exchange steps to reduce the number of manufacturing stages in the membrane fabrication pipeline.

In one embodiment, the step c) further comprises exchanging solvent.

In one embodiment, the first polymer comprises the first functional group selected from —N$_3$ and —C≡CH, and the second polymer comprises the second functional group selected from —N$_3$ and —C≡CH, wherein when the first functional group is —N$_3$, the second functional group is —C≡CH, and when the first functional group is —C≡CH, the second functional group is —N$_3$.

In one embodiment, the first polymer and the second polymer each have a chemical structure:

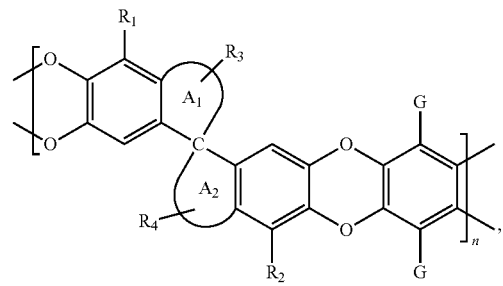

wherein: the carbon indicated by "C" denotes a spiro-carbon;

$A_1$ is selected from

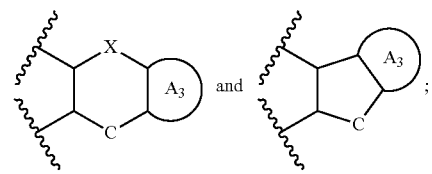

$A_2$ is

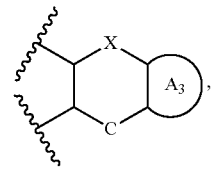

X is independently at each occurrence selected from —CR$_6$, —O—, —S—, —N(R$_6$)$_2$, —C=O, —C=NR$_6$, —C=N—N(R$_6$)$_2$, and C=N—OR$_6$;

R$_1$, R$_2$, R$_3$, and R$_4$ are each independently selected from H and Y—Z;

R$_6$ is independently at each occurrence selected from H, substituted or unsubstituted alkyl, substituted or unsubstituted heteroalkyl, substituted or unsubstituted aryl, and substituted or unsubstituted heteroaryl;

A$_3$ is a selected from substituted or unsubstituted C$_5$-C$_6$ aryl, substituted or unsubstituted C$_5$-C$_6$ heteroaryl, substituted or unsubstituted C$_5$-C$_6$ cycloalkyl and substituted or unsubstituted C$_5$-C$_6$ cyclic heterocycloalkyl;

Y is independently absent or selected from substituted or unsubstituted alkyl, substituted or unsubstituted aryl, —NH—(C=O)—; =NO—C$_{1-6}$ alkyl-; and —(C=O)-phenyl-;

Z is the functional group selected from —N$_3$, —C≡CH, C≡C—R', —C≡N, —(C=O)—H, —SH, and —CH=CH$_2$;

R' is independently at each occurrence selected from substituted or unsubstituted alkyl, substituted or unsubstituted heteroalkyl, substituted or unsubstituted aryl, substituted or unsubstituted heteroaryl, —CN, —CO$_2$R", —(C=O)—N(R")$_2$, and —(C=O)—R";

R" is selected from H, substituted or unsubstituted alkyl, substituted or unsubstituted heteroalkyl, substituted or unsubstituted aryl, and substituted or unsubstituted heteroaryl;

G is selected from Y—Z, halogen, —CN, substituted or unsubstituted aryl, and substituted or unsubstituted heteroaryl; and n is an integer from 5 to 100,000.

In one embodiment, the present invention provides a method of preparing a cross-linked polymer membrane according to Scheme 1:

Scheme 1
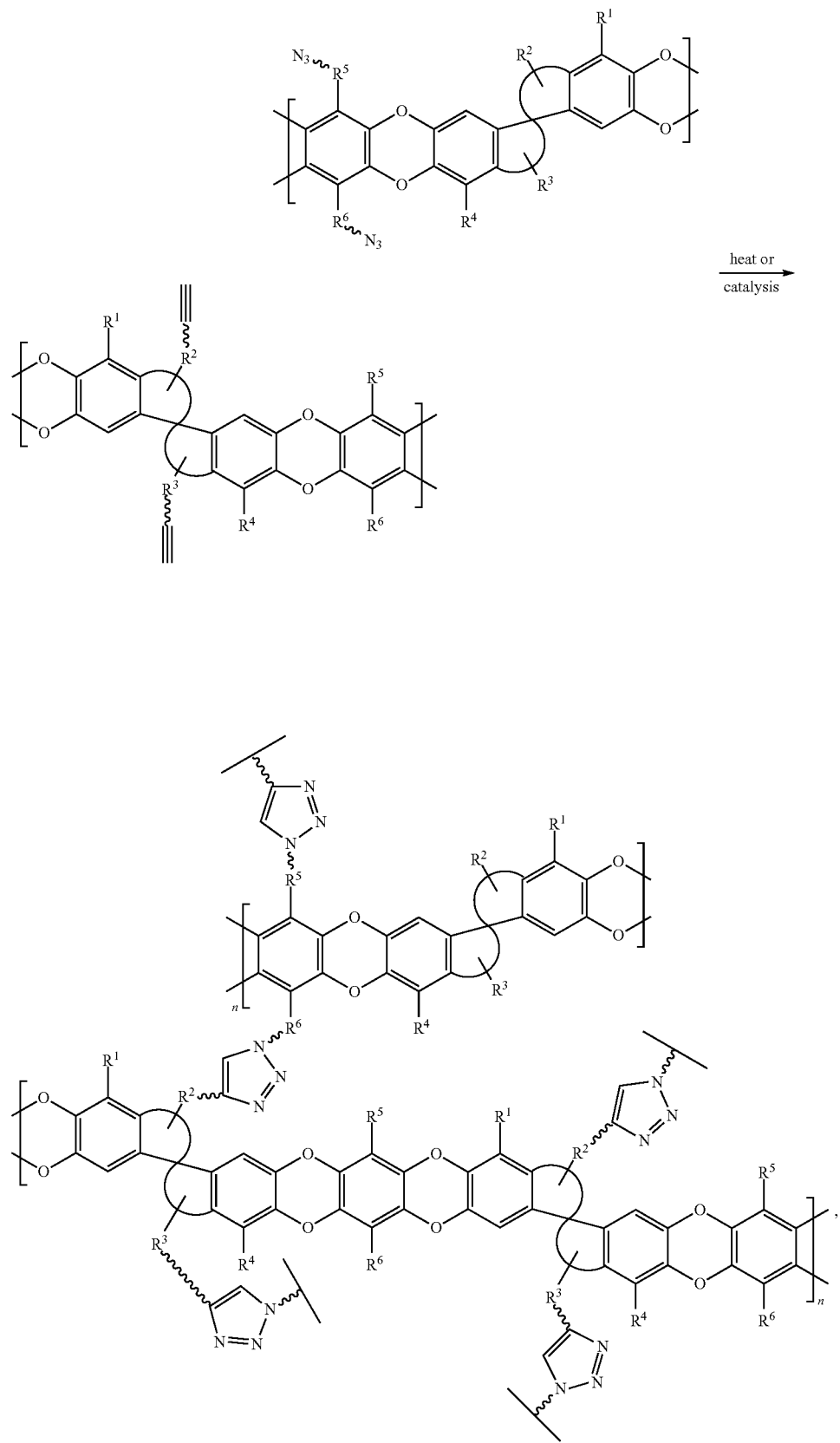

wherein $R_1$, $R_2$, $R_3$, $R_4$, $R_5$, and $R_6$ are each independently at each occurrence selected from H, substituted or unsubstituted alkyl, substituted or unsubstituted heteroalkyl, substituted or unsubstituted aryl, and substituted or unsubstituted heteroaryl, the method comprising the steps of:

a) providing a first polymer comprising a first functional group —$N_3$ and a second polymer comprising a second functional group —C≡CH, b) fabricating the first polymer and the second polymer into a desired membrane;

c) crosslinking the fabricated membrane of step b) by reacting the first functional group —$N_3$ and the second functional group —C≡CH to form a triazole connection, thus obtaining the cross-linked polymer membrane.

In one embodiment, step c) of crosslinking the fabricated membrane of step b) comprises heating the fabricated membrane to between about room temperature and about 200° C. to react the first functional group and the second functional group.

In one embodiment, the step c) of crosslinking the fabricated membrane of step b) comprises submersing the fabricated membrane in a nonsolvent solution comprising a copper catalyst for the reaction between the first functional group —$N_3$ and the second functional group —C≡CH.

In one embodiment, the nonsolvent solution comprising a copper catalyst is a solution of copper(I) salt. Suitable Cu(I) salts include, but are not limited to, copper(I) ascorbate, copper(I) iodide, copper(I) bromide, copper(I) chloride, copper(I) acetate, $L_n$Cu(I) X, where L is selected from phosphine, amine, and/or pyridyl, n is an integer from 0 to 4, and X is selected from Cl, Br, I, OAc, and/or $BF_4$, and the combination of Cu(II) salts and sodium ascorbate, including but not limited to $CuSO_4$, $Cu(OAc)_2$, $CuBr_2$, $CuCl_2$. In one embodiment, the nonsolvent solution comprising a copper catalyst is a solution of copper (I) ascorbate.

In one embodiment, the present invention provides a method of preparing a cross-linked polymer membrane according to Scheme 2:

Scheme 2

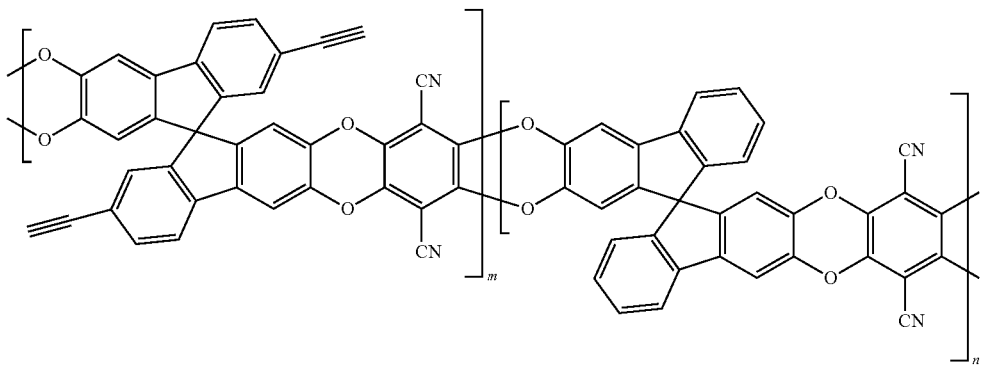

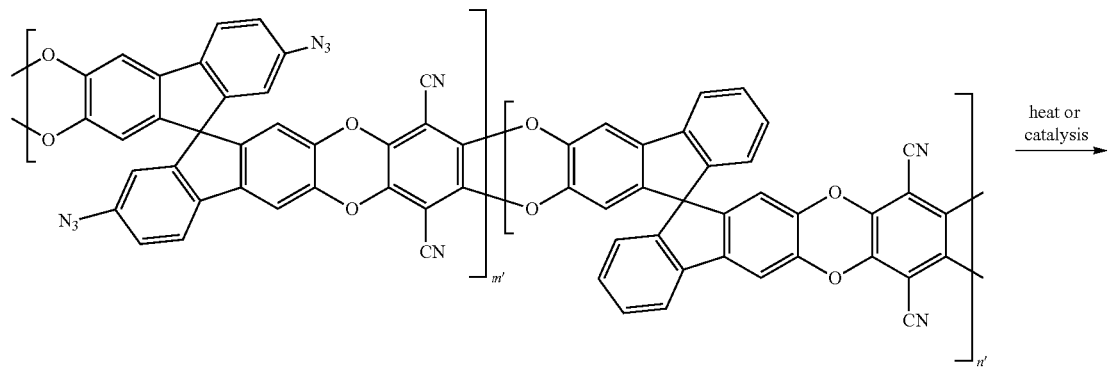

-continued

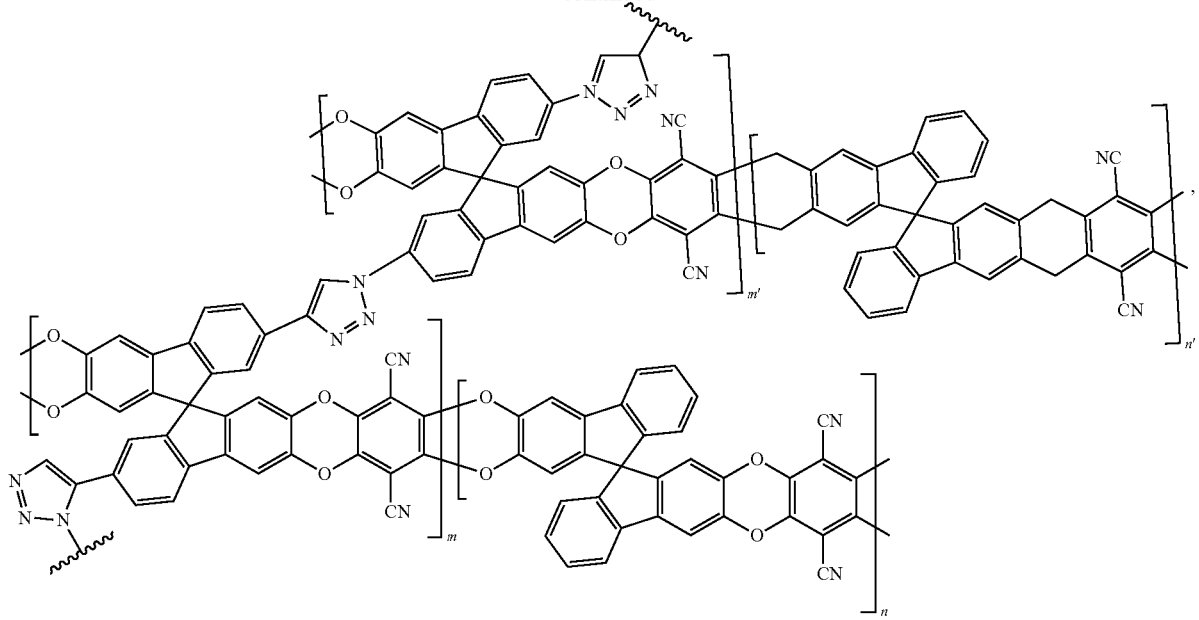

wherein n, n', m', and m' are each independently an integer from 5 to 100,000, the method comprising the steps of:

a) providing a first polymer comprising a first functional group —N₃ and a second polymer comprising a second functional group —C≡CH, b) fabricating the first polymer and the second polymer into a desired membrane;

c) crosslinking the fabricated membrane of step b) by reacting the first functional group —N₃ and the second functional group —C≡CH to form a triazole connection, thus obtaining the cross-linked polymer membrane.

In one embodiment, the step b) of fabricating the first polymer and the second polymer into a desired membrane is performed in a solvent.

In one embodiment, the step c) of crosslinking the fabricated membrane of step b) comprises submersing the fabricated membrane in a nonsolvent solution comprising a copper catalyst for the reaction between the first functional group —N3 and the second functional group —C≡CH.

In one embodiment, the nonsolvent solution comprising a copper catalyst is a solution of copper ascorbate.

In one aspect of the present invention, a cross-linked polymer membrane prepared according to any of the methods described above is provided.

In one embodiment, the membrane according to the invention is insoluble in strong polar aprotic solvents. In one embodiment, the membrane is insoluble in organic solvents comprising dichloromethane, chlorobenzene, chloroform, methylene chloride, cyclohexane, hexanes, heptanes, 1,2-dichloroethane, diethyl ether, methyl t-butyl ether, carbon tetrachloride, xylenes, toluene, ethyl acetate, butyl acetate, DMF, DMAc, NMP, or DMSO, water, and/or fluorocarbons comprising perfluorohexane, perfluoroheptane, perfluorooctane, perfluorononane, 2H,3H-decafluoropentane, perfluorodecaline, perfluoromethylcyclohexane, hexafluorobenzene, octafluorotoluene, perfluoro(1,3-dimethylcyclohexane), perfluorotributylamine, or hexafluoroisopropyl methyl ether.

II. Crosslinking Via Addition of Small Molecule

In this aspect, the initial membrane formation is similar to the direct crosslinking described above. In one variation, after fabrication of the membrane the as-formed membrane can be submerged in a solution of an additional molecule that crosslinks the polymer membrane. This step can be combined with normal solvent exchange processes to reduce manufacturing stages in the membrane fabrication pipeline.

In another embodiment, the membrane may be cast with the small molecule present.

Examples of such small molecules are shown in FIG. 2. The general method of achieving this type of crosslinking is also shown in Scheme 3.

Scheme 3

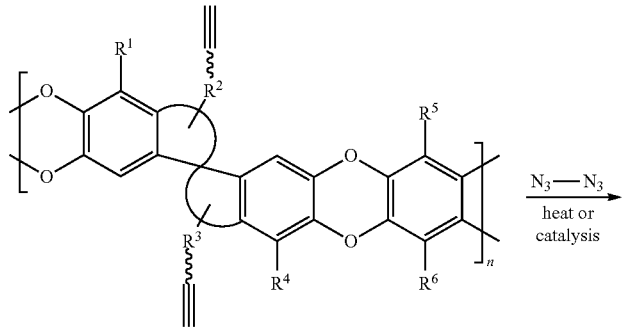

-continued

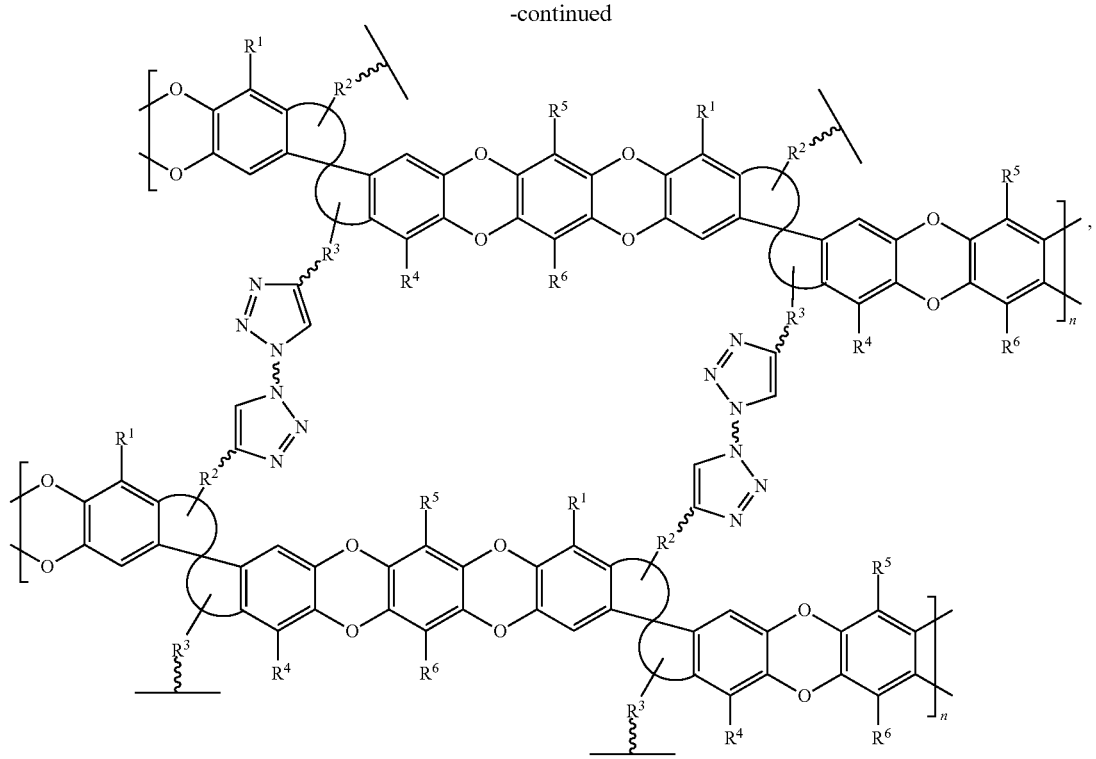

wherein $R_1$, $R_2$, $R_3$, $R_4$, $R_5$, and $R_6$ are each independently at each occurrence selected from H, substituted or unsubstituted alkyl, substituted or unsubstituted heteroalkyl, substituted or unsubstituted aryl, and substituted or unsubstituted heteroaryl, and n is an integer from 5 to 100,000.

In one aspect, the present invention provides a method of preparing a cross-linked polymer membrane comprising the steps of:

a) providing a polymer comprising a first functional group selected from —$N_3$, —C≡CH, C≡C—R', —C≡N, —(C═O)—H, —SH, —CH═$CH_2$, —CH═CHR', —$NH_2$, —NR'—NHR', and —O—NHR', wherein R' is selected from substituted or unsubstituted alkyl, substituted or unsubstituted heteroalkyl, substituted or unsubstituted aryl, substituted or unsubstituted heteroaryl, —CN, —$CO_2$R", —(C═O)—N(R")$_2$, and —(C═O)—R", and R" is independently at each occurrence selected from H, substituted or unsubstituted alkyl, substituted or unsubstituted heteroalkyl, substituted or unsubstituted aryl, and substituted or unsubstituted heteroaryl, and b) fabricating the polymer into a desired membrane;

c) contacting the fabricated membrane of step b) with a compound comprising a second functional group selected from —$N_3$, —C≡CH, C—C—R', —C≡N, —(C═O)—H, —SH, —CH═$CH_2$', —CH═CHR', —$NH_2$, —NR'—NHR', and —O—NHR', wherein the second functional group is capable of irreversibly reacting with the first functional group to form a covalent connection;

d) crosslinking the fabricated membrane of step b) with the compound of step c) by reacting the first functional group and the second functional group to form the covalent connection, thus obtaining the cross-linked polymer membrane.

In one embodiment of the above method, the polymer comprising the first functional group has the following chemical structure:

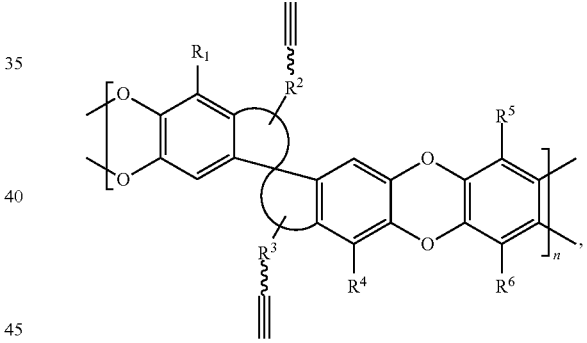

wherein $R_1$, $R_2$, $R_3$, $R_4$, $R_5$, and $R_6$ are each independently at each occurrence selected from H, substituted or unsubstituted alkyl, substituted or unsubstituted heteroalkyl, substituted or unsubstituted aryl, and substituted or unsubstituted heteroaryl, and n is an integer from 5 to 100,000.

In one embodiment, the compound comprising the second functional group has a structure according to formula:

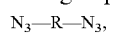

$N_3$—R—$N_3$, wherein R is selected from a substituted or unsubstituted alkyl, substituted or unsubstituted heteroalkyl, substituted or unsubstituted aryl, and substituted or unsubstituted heteroaryl.

In one embodiment, step c) of contacting the fabricated membrane of step b) with a compound comprising the second functional group is performed by submersing the fabricated membrane in a solution of the compound comprising the second functional group.

In one embodiment, the present invention provides a method of preparing a cross-linked polymer membrane according to Scheme 4:

Scheme 4

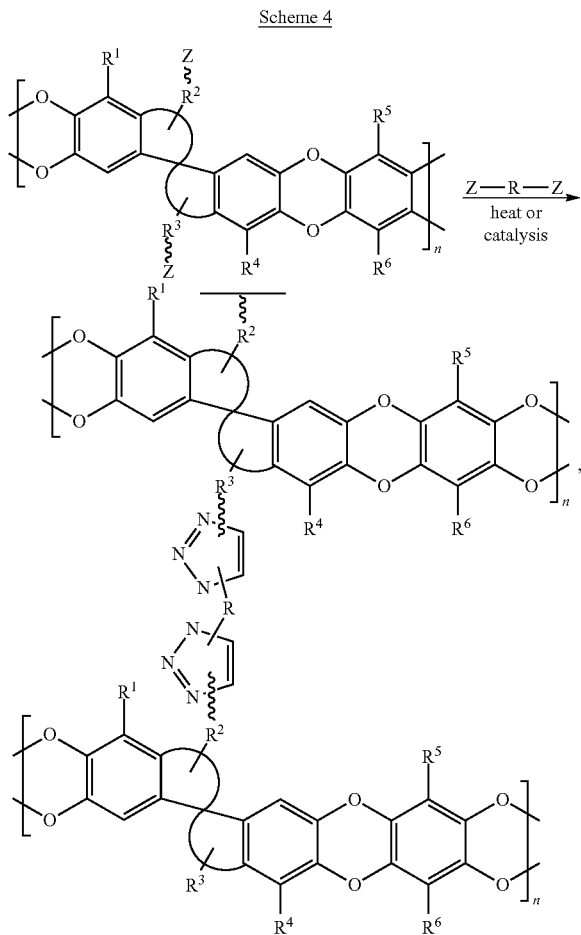

wherein Z is a group selected from —N$_3$ and —C≡CH,

R is selected from a substituted or unsubstituted alkyl, substituted or unsubstituted heteroalkyl, substituted or unsubstituted aryl, and substituted or unsubstituted heteroaryl, and wherein R$_1$, R$_2$, R$_3$, R$_4$, R$_5$, and R$_6$ are each independently at each occurrence selected from H, substituted or unsubstituted alkyl, substituted or unsubstituted heteroalkyl, substituted or unsubstituted aryl, and substituted or unsubstituted heteroaryl, the method comprising the steps of:

a) providing a polymer comprising a functional group Z selected from —N$_3$ and —C≡CH, b) fabricating the polymer into a desired membrane;

c) contacting the fabricated membrane of step b) with a compound comprising a functional group Z selected from —N$_3$ and —C≡CH, wherein if the polymer functional group of step (a) is —N$_3$, then the compound functional group is —C≡CH, and if the polymer functional group of step (a) is —C≡CH, then the compound functional group is —N$_3$;

d) crosslinking the fabricated membrane of step b) with the compound of step c) comprising the functional group by reacting the functional group —C≡CH with the functional group —N$_3$ to form a triazole connection, thus obtaining the cross-linked polymer membrane.

In one embodiment, step d) of crosslinking the fabricated membrane of step b) with the compound of step c) comprises heating to from about room temperature to about 200° C.

In one embodiment, the step d) of crosslinking the fabricated membrane of step b) with the compound of step c) comprises submersing the fabricated membrane in a solution comprising the compound of step c) and a catalyst for initiating the reaction between the functional group —C≡CH and the functional group —N$_3$.

In one embodiment, the catalyst is a copper catalyst including, but not limited to, copper(I) ascorbate, copper(I) iodide, copper(I) bromide, copper(I) chloride, copper(I) acetate, L$_n$Cu(I) X, where L is selected from phosphine, amine, and/or pyridyl, n is an integer from 0 to 4, and X is selected from Cl, Br, I, OAc, and/or BF$_4$, and the combination of Cu(II) salts and sodium ascorbate, including but not limited to CuSO$_4$, Cu(OAc)$_2$, CuBr$_2$, CuCl$_2$.

In one embodiment, the copper catalyst is copper ascorbate.

In one embodiment, the present invention provides a method of preparing a cross-linked polymer membrane according to Scheme 5:

Scheme 5

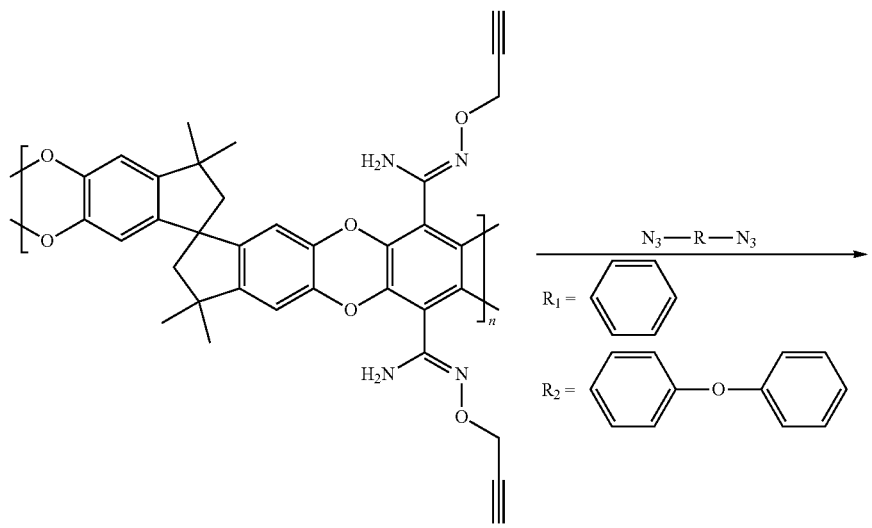

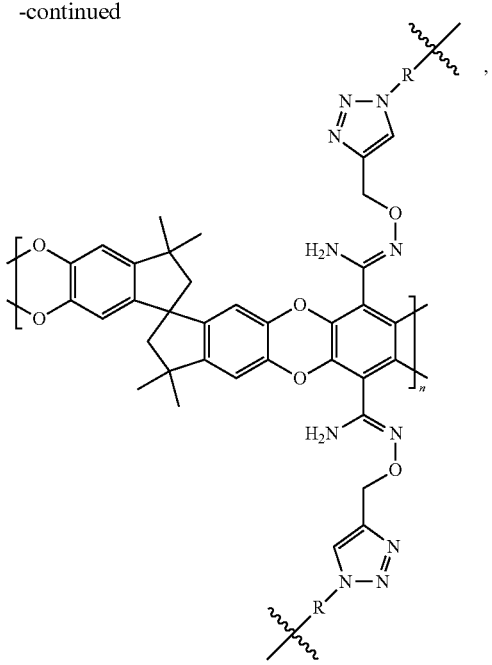

wherein n is an integer from 5 to 100,000, and

R independently at each occurrence is selected from substituted or unsubstituted alkyl, substituted or unsubstituted heteroalkyl, substituted or unsubstituted aryl, and substituted or unsubstituted heteroaryl.

In one embodiment, R is selected from $R_1$ and $R_2$, wherein $R_1$ is phenyl and $R_2$ is diphenyl ether.

In one aspect of the present invention, a cross-linked polymer membrane prepared according to any of the methods described above is provided.

In one embodiment, the membrane according to the invention is insoluble in strong polar aprotic solvents. In one embodiment, the membrane is insoluble in organic solvents comprising dichloromethane, chlorobenzene, chloroform, methylene chloride, cyclohexane, hexanes, heptanes, 1,2-dichloroethane, diethyl ether, methyl t-butyl ether, carbon tetrachloride, xylenes, toluene, ethyl acetate, butyl acetate, DMF, DMAc, NMP, or DMSO, water, and/or fluorocarbons comprising perfluorohexane, perfluoroheptane, perfluorooctane, perfluorononane, 2H,3H-decafluoropentane, perfluorodecaline, perfluoromethylcyclohexane, hexafluorobenzene, octafluorotoluene, perfluoro(1,3-dimethylcyclohexane), perfluorotributylamine, or hexafluoroisopropyl methyl ether.

III. Interfacial Crosslinking

In one aspect of the present invention, a membrane support is first fabricated using conventional membrane manufacturing techniques (e.g., dry jet, wet quench solution spinning). The membrane support is then dipped in a solution of one crosslinker material, and then dipped in a second solution of a polymer dissolved in a solvent that is immiscible with the solvent in the first solution. A crosslinked membrane is then formed at the liquid-liquid interface, which can be engineered to occupy the outer surface of the membrane support. Other fabrication approaches include counterflow of the catalyst/crosslinker solution and the polymer solution.

Without wishing to be bound by any theory, it is hypothesized that by polymerizing and cross-linking PIM by interfacial polymerization on a solid support, a 100-200 nm thick PIM-1 membrane could be cast and mechanical integrity would increase with the addition of a solid support.

III.1. Interfacial Crosslinking of Free-Standing Film

In one aspect, the present invention provides a method of preparing a cross-linked polymer membrane at an interface of a first solvent and a second solvent, wherein the first solvent is immiscible with the second solvent, the method comprising the steps of:

a) providing a polymer comprising a first functional group selected from —$N_3$, —C≡CH, C≡C—R', —C≡N, —(C=O)—H, —SH, —CH=$CH_2$, —CH=CHR', —$NH_2$, —NR'—NHR', and —O—NHR', wherein R' is selected from substituted or unsubstituted alkyl, substituted or unsubstituted heteroalkyl, substituted or unsubstituted aryl, substituted or unsubstituted heteroaryl, —CN, —$CO_2$R", —(C=O)—N(R")$_2$, and —(C=O)—R", and R" is independently at each occurrence selected from H, substituted or unsubstituted alkyl, substituted or unsubstituted heteroalkyl, substituted or unsubstituted aryl, and substituted or unsubstituted heteroaryl;

b) fabricating the polymer into a desired membrane;

c) contacting the fabricated membrane of step b) with a compound comprising a second functional group selected from —$N_3$, —C≡CH, C≡C—R', —C≡N, —(C=O)—H, —SH, —CH=$CH_2$, —CH=CHR', —$NH_2$, —NR'—NHR', and —O—NHR', wherein the second functional group is capable of irreversibly reacting with the first functional group to form a covalent connection, by dissolving the fabricated membrane and the compound in the first solvent;

d) combining the first solvent comprising fabricated membrane and the compound and a second solvent comprising a catalyst for initiating a reaction between the first functional group and the second functional group, e) crosslinking the fabricated membrane of step b) with the compound of step c) by reacting the first functional group and the second functional group to form the covalent connection, wherein the crosslinking reaction between the first functional group and the second functional group occurs at the interface of the first solvent and the second solvent, thereby forming the cross-linked polymer membrane at the interface of the first solvent and the second solvent.

In one embodiment, the first functional group is selected from —$N_3$ and —C≡CH, and the second functional group is selected from —$N_3$ and —C≡CH, wherein when the first functional group is —$N_3$, the second functional group is —C≡CH, and when the first functional group is —C≡CH, the second functional group is —$N_3$.

In one embodiment, the catalyst is a copper catalyst. In one embodiment, the catalyst is a copper (I) catalyst. In one embodiment, the catalyst is copper ascorbate.

In one embodiment, the first solvent is an organic solvent and the second solvent is selected from water and a fluorocarbon solvent, or wherein the first solvent is water and the second solvent is selected from an organic solvent and a fluorocarbon solvent; or when the first solvent is a fluorocarbon solvent and the second solvent is selected from an organic solvent and water.

In one embodiment, the first solvent is an organic solvent comprising dichloromethane, chlorobenzene, chloroform, methylene chloride, cyclohexane, hexanes, heptanes, 1,2-dichloroethane, diethyl ether, methyl t-butyl ether, carbon tetrachloride, xylenes, toluene, ethyl acetate, or butyl acetate, and the second solvent is selected from water and a fluorocarbon comprising perfluorohexane, perfluoroheptane, perfluorooctane, perfluorononane, 2H,3H-decafluoropentane, perfluorodecaline, perfluoromethylcyclohexane, hexafluorobenzene, octafluorotoluene, perfluoro(1,3-dimethylcyclohexane), perfluorotributylamine, or hexafluoroisopropyl methyl ether.

In one embodiment, the first solvent is water and the second solvent is selected from an organic solvent comprising dichloromethane, chlorobenzene, chloroform, methylene chloride, cyclohexane, hexanes, heptanes, 1,2-dichloroethane, diethyl ether, methyl t-butyl ether, carbon tetrachloride, xylenes, toluene, ethyl acetate, or butyl acetate, and a fluorocarbon solvent comprising perfluorohexane, perfluoroheptane, perfluorooctane, perfluorononane, 2H,3H-decafluoropentane, perfluorodecaline, perfluoromethylcyclohexane, hexafluorobenzene, octafluorotoluene, perfluoro(1,3-dimethylcyclohexane), perfluorotributylamine, or hexafluoroisopropyl methyl ether.

In one embodiment, the first solvent is a fluorocarbon solvent comprising perfluorohexane, perfluoroheptane, perfluorooctane, perfluorononane, 2H,3H-decafluoropentane, perfluorodecaline, perfluoromethylcyclohexane, hexafluorobenzene, octafluorotoluene, perfluoro(1,3-dimethylcyclohexane), perfluorotributylamine, or hexafluoroisopropyl methyl ether, and the second solvent is selected from water and an organic solvent comprising dichloromethane, chlorobenzene, chloroform, methylene chloride, cyclohexane, hexanes, heptanes, 1,2-dichloroethane, diethyl ether, methyl t-butyl ether, carbon tetrachloride, xylenes, toluene, ethyl acetate, or butyl acetate.

III.2. Interfacial Crosslinking on a Solid Support

In one aspect, the present invention provides a method of preparing a cross-linked polymer membrane on a solid support comprising the steps of:

a) providing a polymer comprising a first functional group selected from —$N_3$, —C≡CH, C≡C—R', —C≡N, —(C=O)—H, —SH, —CH=$CH_2$, —CH=CHR', —$NH_2$, —NR'—NHR', and —O—NHR', wherein R' is selected from substituted or unsubstituted alkyl, substituted or unsubstituted heteroalkyl, substituted or unsubstituted aryl, substituted or unsubstituted heteroaryl, —CN, —$CO_2$R", —(C=O)—N(R")$_2$, and —(C=O)—R", and R" is independently at each occurrence selected from H, substituted or unsubstituted alkyl, substituted or unsubstituted heteroalkyl, substituted or unsubstituted aryl, and substituted or unsubstituted heteroaryl;

b) submerging a solid support into a solution comprising the polymer comprising the first functional group and a compound comprising a second functional group selected from —$N_3$, —C≡CH, C≡C—R', —C≡N, —(C=O)—H, —SH, —CH=$CH_2$, —CH=CHR', —$NH_2$, —NR'—NHR', and —O—NHR', wherein the second functional group is capable of irreversibly reacting with the first functional group to form a covalent connection;

d) crosslinking the polymer of step a) with the compound of step b) by reacting the first functional group and the second functional group to form the covalent connection on solid support, thus obtaining the cross-linked polymer membrane of a solid support.

In one embodiment, the solid support is submersed in a solution comprising a catalyst for initiating the reaction of the first functional group with the second functional group prior to the step b).

In one embodiment, the solution comprising the catalyst is an aqueous solution and the catalyst is a water-soluble copper catalyst.

In one embodiment, the solution comprising the polymer comprising the first functional group and the compound comprising the second functional group comprises a solvent selected from dichloromethane, chlorobenzene, chloroform, methylene chloride, cyclohexane, hexanes, heptanes, 1,2-dichloroethane, diethyl ether, methyl t-butyl ether, carbon tetrachloride, xylenes, toluene, ethyl acetate, butyl acetate, tetrahydrofuran, tetrahydropyran, dimethyl formamide, NMP, acetone, ethanol, methanol, and toluene.

In one embodiment, the solid support is selected from a metal surface, a ceramic surface, a zeolite surface, and a polymer surface.

IV Covalent Attachment to a Solid Support

A solid support, e.g., a ceramic membrane support, can be functionalized with molecules that are complementary to groups on the backbone of a polymer that will be utilized to fabricate the membrane. The ceramic support is coated with a polymer solution, and the resulting membrane composite is heated to initiate reaction between the complementary groups or soaked in a nonsolvent solution containing the catalyst for the reaction.

The present invention discloses fabrication of defect-free supported microporous membranes covalently bonded to ceramic supports. To fabricate this supported membrane, a solution of functionalized polymers in organic/aqueous solvents at a concentration of 0.01% to 80% w/w with/without additives (additives may be used for further crosslinking or used to initiate reactions) were spin-coated on selective ceramic discs with reactive functional groups. Chemical reaction between polymers and functionalized ceramic surfaces was then initiated by heating or other catalytic methods to form covalent bond. Other coating techniques such as drop casting, dip coating, ink jet printing or roll-to-roll fabrications may also be used to form polymer coatings.

In one aspect, the present invention provides a method of preparing a cross-linked polymer membrane covalently attached to a solid support comprising the steps of:

a) covalently attaching to the solid support a compound comprising a first functional group selected from —$N_3$, —C≡CH, C≡C—R', —C≡N, —(C=O)—H, —SH, —CH=$CH_2$, —CH=CHR', —$NH_2$, —NR'—NHR', and —O—NHR', wherein R' is selected from substituted or unsubstituted alkyl, substituted or unsubstituted heteroalkyl, substituted or unsubstituted aryl, substituted or unsubstituted heteroaryl, —CN, —CO$_2$R", —(C=O)—N(R")$_2$, and —(C=O)—R", and R" is independently at each occurrence selected from H, substituted or unsubstituted alkyl, substituted or unsubstituted heteroalkyl, substituted or unsubstituted aryl, and substituted or unsubstituted heteroaryl;

b) fabricating a polymer membrane on the functionalized solid support with a polymer comprising a second functional group selected from —N$_3$, —C≡CH, C≡C—R', —C≡N, —(C=O)—H, —SH, —CH=CH$_2$, —CH=CHR', —NH$_2$, —NR'—NHR', and —O—NHR', wherein the second functional group is capable of irreversibly reacting with the first functional group to form a covalent connection, c) reacting the first functional group and the second functional group to form the cross-linked polymer membrane, thus obtaining the cross-linked polymer membrane covalently attached to the solid support.

In one embodiment, the reaction of step c) is initiated by heating the polymer-coated functionalized support.

In one embodiment, the reaction of step c) is initiated by submerging the polymer-coated functionalized support in a solution comprising a catalyst. In one embodiment, the catalyst is a copper catalyst.

V. Interfacial Polymerization

In one aspect, a membrane support may be first fabricated using conventional membrane manufacturing techniques (e.g., dry jet, wet quench solution spinning). The membrane support is then dipped in a solution of one monomer, and then dipped in a second solution of another monomer dissolved in a solvent that is immiscible with the solvent in the first solution. The polymer membrane is formed at the liquid-liquid interface, which can be engineered to occupy the outer surface of the membrane support.

VI. Direct Cast and Crosslink on Copper Membrane Surface

In one aspect, the present invention provides a method of preparing a cross-linked polymer membrane on solid copper support comprising the steps of:

a) providing a first polymer comprising a first functional group selected from —N$_3$, —C≡CH, C≡C—R', —C≡N, —(C=O)—H, —SH, —CH=CH$_2$, —CH=CHR', —NH$_2$, —NR'—NHR', and —O—NHR', and a second polymer comprising a second functional group selected from —N$_3$, —C≡CH, C≡C—R', —C≡N, —(C=O)—H, —SH, —CH=CH$_2$, —CH=CHR', —NH$_2$, —NR'—NHR', and —O—NHR', wherein the second functional group is capable of irreversibly reacting with the first functional group to form a covalent connection, wherein R' is selected from substituted or unsubstituted alkyl, substituted or unsubstituted heteroalkyl, substituted or unsubstituted aryl, substituted or unsubstituted heteroaryl, —CN, —CO$_2$R", —(C=O)—N(R")$_2$, and —(C=O)—R", and R" is independently at each occurrence selected from H, substituted or unsubstituted alkyl, substituted or unsubstituted heteroalkyl, substituted or unsubstituted aryl, and substituted or unsubstituted heteroaryl;

b) coating the copper support with the first polymer and the second polymer;

c) crosslinking the first polymer and the second polymer by reacting the first functional group and the second functional group to form the covalent connection on solid copper support, thus obtaining the cross-linked polymer membrane of solid copper support.

In one embodiment, the first and the second polymer may be comprised in a single polymer blend comprising the first functional group and the second functional group.

In one embodiment, the crosslinking reaction is initiated by heating the copper support coated with the first polymer and the second polymer.

VII. Methods for Vapor and Liquid Separations

The favorable combination of porosity, rigidity, thermal, chemical and mechanical stability imparted by the cross-linking of the materials when forming a membrane allows high permeability and selectivity of these materials for both gas and liquid separations. The cross-linked membranes based on these polymers separate the molecules based on the relative difference between their solubility and diffusion (molecular size and shape) through the polymer.

The membranes have a molecular weight cut-off (i.e., >90% rejection of species higher than a specified molecular weight) in the 150-2000 Dalton range, and more preferably in the 150-1500 Dalton range, and more specifically 150-600 Dalton range. The pore size of the membranes can be in the range of 0.5-2 nm making them suitable for the separation of a range of gas and liquids in petrochemical, refining, upstream, natural gas, air purification and pharmaceutical applications.

The membranes can be used for various vapor separation applications such as Ethane, Propane, Butane, and other of volatile organic compounds (VOC) from air, CH$_4$, or Nitrogen.

The membranes can be used for a range of liquid separations as well. The membrane can achieve size based separation of whole crude and crude fractions. Typical whole crude molecular weight ranges from 50-2000 Dalton. The membranes can provide a naphtha or kerosene cut out of the whole crude where the membrane has a MWCO of 100-500 Daltons. Within the naphtha and kerosene range the cross-linked membranes can separate further based on MW and molecular class. These membranes can be exploited to give class based separation of aromatics, cyclo-paraffins, n- and iso-paraffins within a certain crude fraction such as the naphtha (IBP-350° F.) and kerosene (350-500° F.), distillate (500-650° F.) and vacuum gas oil (650-1050° F.) fractions. Due to the MWCO of these membranes in the <500 Dalton range, the membranes can be used to remove asphaltenes, multi-ring (3+ ring) aromatics, hetero atoms, metals (Nickel, Vanadium, Iron, Calcium), sulfides from crude oil and its fractions.

The membranes can further be utilized in a nanofiltration mode for the removal of homogenous catalysts such as Rhodium, Nickel Ligand based, cobalt carbonyl catalyst from organic solvents, polyolefin oligomer and polymers from hexane, sulfolane/NMP solvents from vacuum reside or vacuum gas oil range aromatic molecules, metallocene catalyst in higher olefins from solvents and lube oil from solvents such as MEK and toluene. The membranes can be utilized for the dehydration of organics such as alcohols (ethanol, butanol) or ketones from water. Cross-linked membranes provide the required structural, chemical, and mechanical stability to the membranes which enables the separation of various organic molecules which would otherwise swell, plasticize or dissolve un-crosslinked membranes significantly reducing their practical lifetime.

The membranes can alternatively be used as a membrane reactor due to their high thermal, chemical and mechanical stability. Membrane reactors enable selective permeation of a product or reactant molecule thus improving the efficiency of equilibrium-controlled reactions. Examples of membrane reactors include p-xylene selective membrane to improve the efficiency of vapor or liquid phase isomerization reaction, H$_2$ selective membrane to improve the efficiency of direct methane to liquids reaction, water gas shift conversion reaction and propane dehydrogenation reaction, improving esterification yields by removal of water.

The membranes can be used in processes with multiple stages or a cascade type configuration operating under various modalities, e.g. nanofiltration (NF), reverse osmosis (RO), forward osmosis (FO), pressure retarded osmosis (PRO), pervaporation, gas separations and with different geometries, e.g. hollow fiber, monolith, spiral wound, and plate-frame, disc, coupons. The membrane process can be operated to get a permeate yield from about 5 wt. %-95 wt. %. Flux through the membrane can vary depending on the membrane pore size and test conditions. The flux to be in the range of about 0.1-20 gallons/ft$^2$/day range.

Membranes employed in this process should be stable at temperature from about 75-760° F. (24-404° C.), e.g., between about 120-575° F. (49-302° C.) or 212-392° F. (100-200° C.). Finally, whether operating in UF, NF, RO, FO, or pervaporation modalities, the presently disclosed processes require elevated transmembrane pressures. Membranes used herein should be able to withstand transmembrane pressures greater than from about ambient to about 2000 psig (about 13.8 MPag) depending on the membrane modality. For UF, NF and RO the feed is pressurized typically between about 100 psig (about 700 kPag) to 2000 psig (about 13.8 MPag), with about 2000 psig (about 13.8 MPag) being a typical limit for a commercial membrane module. In UF, NF and RO the permeate side is typically between ambient pressure to about 100 psig (about 700 kPag). In pervaporation the feed is anywhere between ambient to about 60 psig (about 400 kPag) and the permeate side is at a vacuum with pressures being typically about 0.2-0.3 bar (3-5 psia) but can be as low as about 0.02 bar. In FO pressure differential does not drive the separation but rather, the driving force is forward osmotic pressure by use of a concentration gradient. In FO a large molecule naturally draws the faster permeating species through the membrane because of its higher osmotic pressure. FO requires another separation step in the permeate but the draw molecule is quite large in comparison to the permeate molecule and then can be easily separated using known techniques, such as distillation.

The membranes may be positioned in a single membrane unit (stage) or in several units, wherein each unit may be comprised of one or more separate membranes. Typically, the number of membrane units may depend on the surface area of the separate membranes in combination with the required quantity of steam to be permeated. The membrane units may include membranes of the same type, or a different type, in terms of composition or configuration. As a consequence, the membrane units may differ from each other, in terms of one or more of shape, permeance, permselectivity, or surface area available for permeation. Furthermore, the membranes may be arranged in series or in parallel, for example.

In one aspect, the membranes may be spin coated on supports that contain longitudinal pores due to their high permeances, although some compaction of the TFC is expected to occur.

EXAMPLES

The following examples illustrate specific aspects of the instant description. The examples should not be construed as limiting, as the examples merely provide specific understanding and practice of the embodiments and their various aspects.

Example 1: Direct Crosslinking

Spirobifluorene PIMs with a specific ratio of alkynes on the backbone were blended in solution with complementary spirobifluorene PIMs containing azides. This polymer solution was processed into a thin film (either free standing or dip-coated onto a fiber). The resulting films were heated above 200° C. to initiate the crosslinking reaction, or were soaked in aqueous solutions of copper (I) catalyst (CuAAC) (FIG. 1). The resulting films were found to be insoluble in strong polar aprotic solvents such as THF.

Example 2: Crosslinking Via Addition of Small Molecule

The nitrile handle on PIM-1 was converted into an alkyne handle, which enables the use of diazide-type crosslinkers. This "PIM-PAO" polymer was dissolved into a casting solvent (e.g., THF) and can be subsequently processed into thin films via knife casting, dip-coating onto fiber supports, or directly spinning the polymer. After processing into a membrane, the PIM-PAO can be crosslinked in solution. One embodiment of this resulted in films with 99% gel content that were totally insoluble in strong polar aprotic solvents (FIG. 2B)

FIG. 3 highlights another specific pathway for generating clickable handles on the PIM backbone. This approach converts some fraction of the nitriles in the PIM-1 backbone into tetrazoles. The tetrazoles can be decorated with a variety of functionalities including alkyne handles that can be subsequently crosslinked using small diazide molecules after membrane fabrication. This crosslinking resulted in significantly reduced solvent swelling of the polymer film while still maintaining very high solvent loadings (FIG. 3B, 3C), thus indicating that the microporosity was likely retained.

Example 3: Interfacial Crosslinking of Free-Standing Film

The initial reaction using PIM-1 utilized a PIM-1 polymer (60,000 kDa M$_w$) functionalized with alkyne sidechains as a "monomer" and used a small di-functional azide to create a cross-linked network at the interface (FIG. 4). Both alkyne functionalized PIM-1 and the diazide were dissolved in chloroform and a water soluble Cu(I) catalyst was used. Since the azide and alkyne will only react in the presence of the Cu(I) catalyst, cross-linking will only occur at the interface. A thin, almost transparent membrane formed after 24 hours (FIG. 4B2). When the test tube was inverted, the membrane could support the weight of the organic solvent layer (FIG. 4B3). Once the membrane was removed from the test tube, it was insoluble in a variety of solvents (FIG. 4B4).

Example 4: Interfacial Crosslinking on a Solid Support

Figures 5A, 5B, 5C:
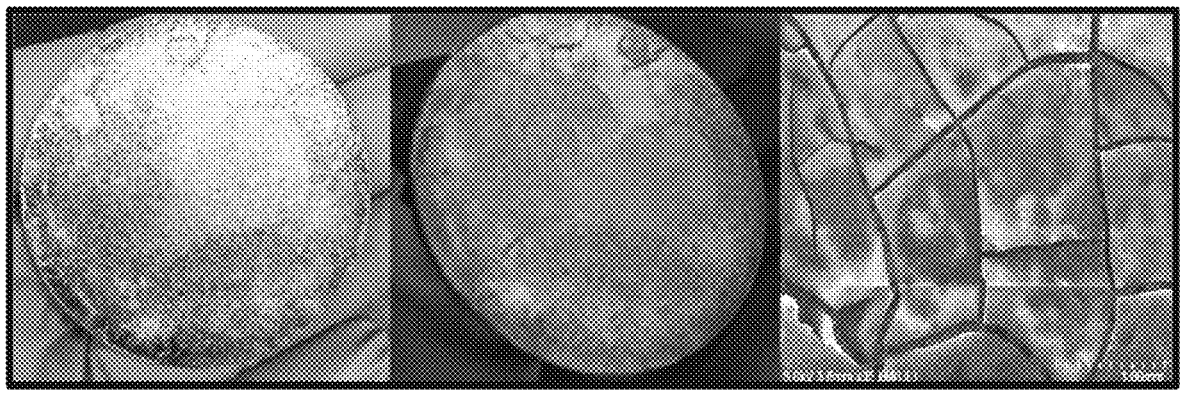
FIGS. 5A-5C depict interfacial cross-linking of PIM-1 polymer on a stainless steel macro-porous support.

Dip coating was initially used to coat the stainless steel macro-porous support with PIM polymer. Using the same reaction shown in FIG. 4. A stainless steel disk was first submerged into a solution of water containing the CuSO$_4$ and sodium ascorbate. The disk was allowed to stay submerged for 5 minutes, before it was removed and excess water on the surface was removed with a Kimwipe. The disk was then submerged into a chloroform solution containing the alkyne functionalized PIM-1 polymer and diazide cross-linker and was allowed to stay in solution overnight. Unreacted monomer and cross-linker were washed away with multiple chloroform washes. As shown in FIG. 5, a large amount of cracking was seen on the polymer surface, resulting in a cracked and non-continuous membrane layer.

It is hypothesized that a combination of factors in the polymerization led to cracking of the membrane; a very large degree of cross-linking, a long reaction time leading to thicker membranes, and delamination of the polymer from the support.

Example 5: Covalent Attachment to a Solid Support

In the above Examples, the PIM-1 was functionalized so that ever nitrile group on the backbone was converted to a tetrazole and alkylated with an alkyne. To reduce the amount of cross-linking, a 10% functionalized alkyne PIM was synthesized.

Additionally, a commercially available polyimide (Matrimid®) was used to cast asymmetric solid supports of micron level thickness. The polyimide dope composition was optimized to produce a defect-free thin skin layer on top of a macroporous bulk layer with a target permeance of a few hundred LMH-bar for commonly tested solvents such as ethanol, toluene, etc. A mixture of 1,6 hexanediamine (a normal Matrimid® cross-linker) and propargyl amine were used to cross-link the Matrimid® films. By incorporating the propargyl amine into the cross-linking of the film, alkyne handles were now present throughout the Matrimid®.

Initially, dip coating was used to covalently attach the PIM to the support. The support (containing alkynes) was first submerged in a water solution containing a copper catalyst for 5 minutes. Once removed from the water solution, the Matrimid® was then submerged in to a chloroform solution containing azide functionalized PIM overnight. Unreacted PIM was removed through multiple chloroform washes. Upon testing in a dead end cell, the permeance of heptane dropped from 450 to 45 LMH/bar for the PIM-Matrimid® thin-film composite when compared to bare Matrimid®. However, SEM analysis showed that two supports had stacked on top of each other which compromised the permeation result.

Figure 6:
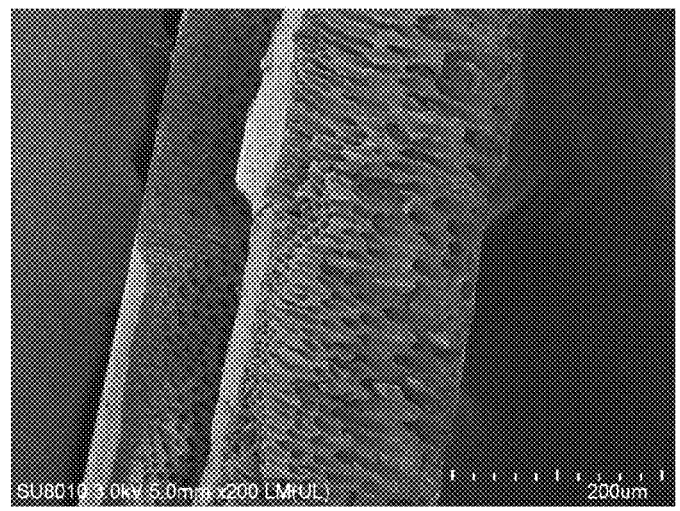
FIG. 6 is a SEM image of stacked Matrimid® supports treated with PIM that showed a decrease in permeance of heptane.
Figure 11:
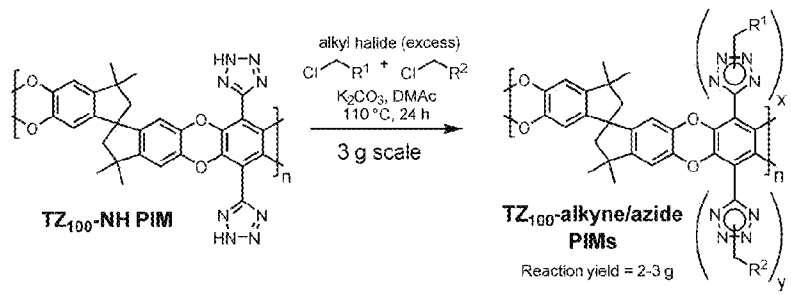
FIG. 11 depicts illustrative non-limiting examples of covalent bonding between reactive functional groups on a ceramic support and polymers containing alkyne or azide functional groups.
Figure 11:
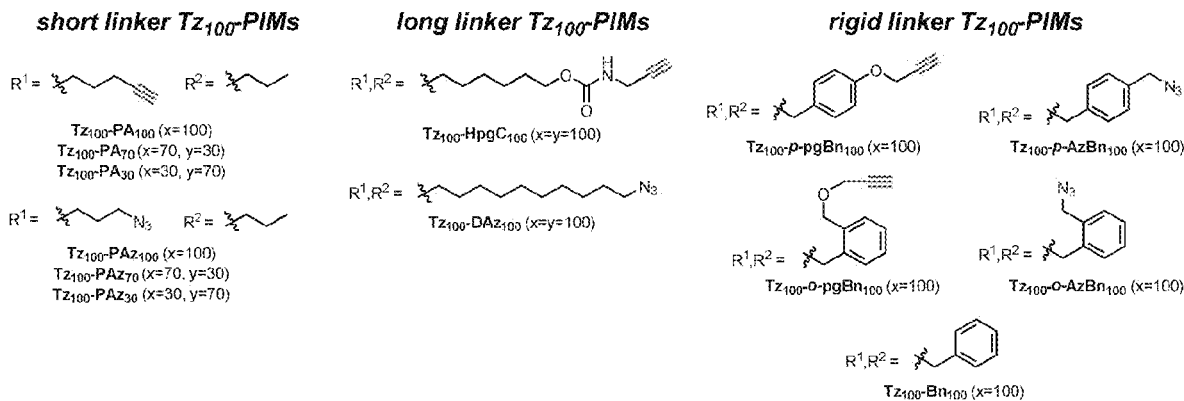

Spin coating was attempted to better control the thickness and uniformity of the functionalized PIM-1 on supports. The flexible, soft polyimide supports were stabilized on a uniformly porous vacuum chuck which ensured flatness and prevented damage by indentation from the conventional, centered vacuum orifice. Polymer was dissolved in chloroform or THF and purified twice using PTFE filters. The solution was dropped onto the skin layer side of the cross-linked polyimide support which was spun at a set revolution rate in a purge of nitrogen gas. The concentration of polymer in the solution, the volume of solution dropped and the spin speed and duration were essential in determining the thickness and uniformity of the nascent film A 0.3 wt % solution of a PIM in THE (as shown in FIG. 6) was spun coat for 30 seconds at 1000 rpm on to a polyacrylonitrile support as a preliminary experiment and placed in a cross flow cell with a 1 mol % triisopropylbenzene/toluene mixture for 120 hours. Under a pressure range of 10-30 bar, the rejection of TIPB remained at 35% while the permeance decreased nearly linearly from 2.4 to 1.8 LMH/bar due to suspected fouling.

It is hypothesized that covalently attached PIMs onto a support using click chemistry avoids the delamination of polymer from the film that usually results in decreased rejection over continuous use.

Figure 19:
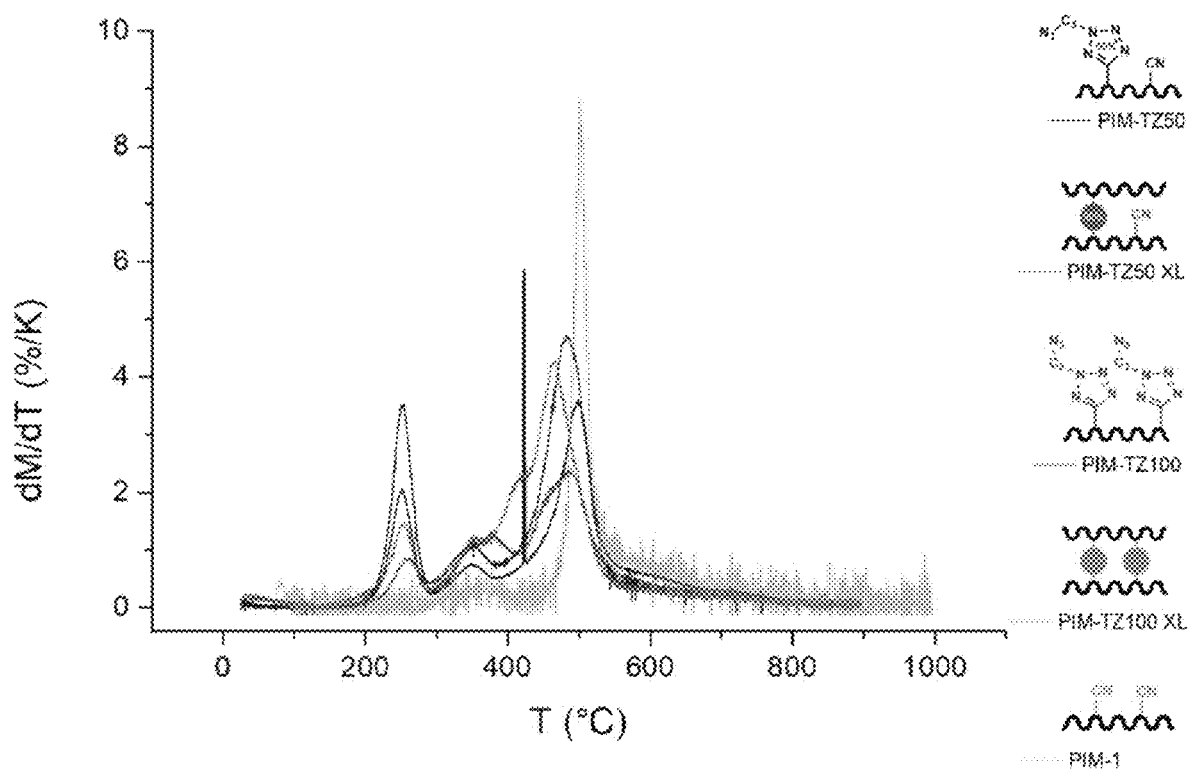
FIG. 19 is a derivative of the magnetization with respect to temperature versus temperature plot for exemplary membranes according to the invention.
Figure 21:
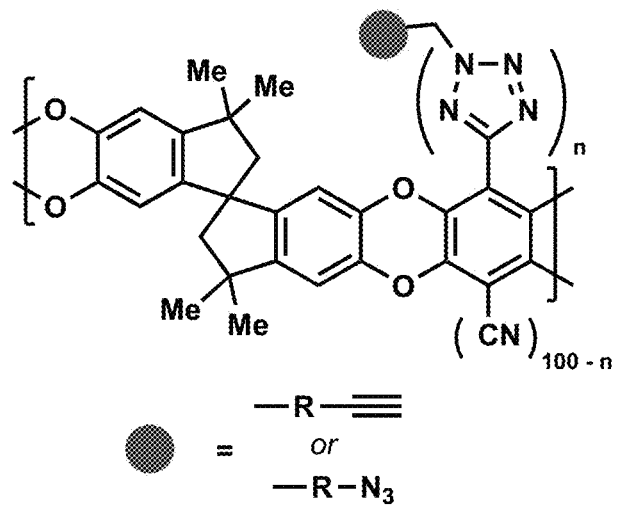
FIG. 21 is a general figure for azide and alkyne-functionalized tetrazole PIMs.
Figure 22:
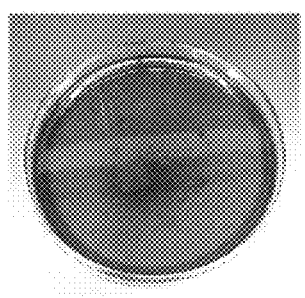
FIG. 22 show photographs of films of new amine-linked PIMs materials.
Figure 22:
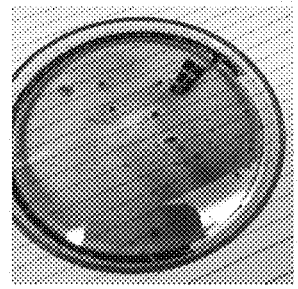
Figure 22:
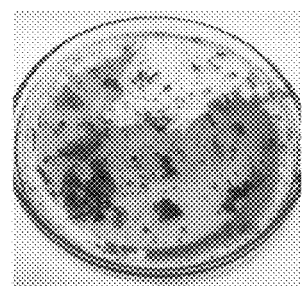
Figure 23:
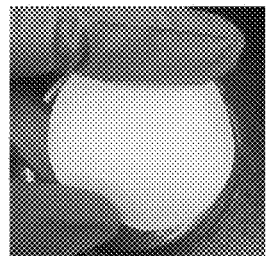
FIGS. 23(A and B) show photographs of examples of films of new amine-linked PIMs materials on solid support.
Figure 23:
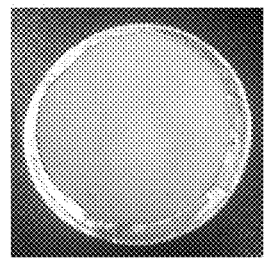

An exemplary dM/dT vs T(K) plot is shown as FIG. 19. Peaks at about 225° C. are from the decomposition of azide present on functionalized PIMs. The black and blue traces are non-cross-linked materials. The pink and red are cross-linked and show the azide signal decreasing as a result of reacting with a dialkyne cross-linker. Additionally, the increase of the peaks in the 400-500° C. range are indicative of the presence of triazole. IR spectroscopy is not suitable to determine the degree of cross-linking as the azide signals are generally too weak to be observed, especially at useful degrees of functionalization (<25%).

Example 6: Additional Embodiments

Once proper casting methods have been optimized resulting in a continuous thin film on top of the solid support, variations on the functionalized on PIM can be explored. Various handles can be functionalized off of the PIM backbones, as shown in Scheme 5. Matrimid® can be functionalized with azides instead of alkynes to covalently attach alkyne PIM. Additionally cross-linkers can be added to increase the degree of crosslinking. It is hypothesized that the separation properties of the polymer can be tuned based on the linkers.

Scheme 6. PIM that was spun coat on PAN in THF for preliminary testing in a cross flow cell containing TIPB/toluene

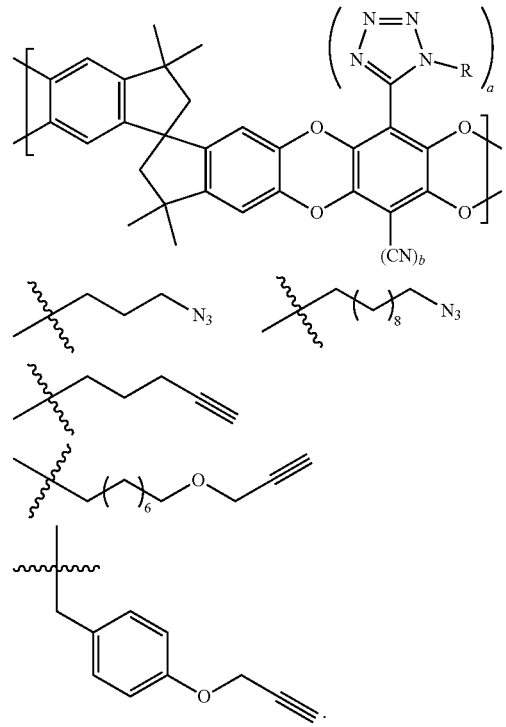

Example 7: Interfacial Polymerization in Liquid Phases

Interfacial CuAAC polymerization was investigated using a variety of multi-functional azide and alkyne monomers, such as those shown in Scheme 6. Monomers B-1, B-2, B-3, and B-4 have been synthesized, purified, and used in interfacial CuAAC polymerization. Both a water soluble, $CuSO_4$ and sodium ascorbate, and organic soluble, $(Ph_3P)_2CuOAc$, catalyst have been screened. To monitor the interfacial CuAAC reaction, longer reaction times, ≥24 hours, were employed to ensure complete membrane formation. Membranes were formed after 24 hours.

Scheme 7: Potential organic and water soluble mulit-functional azides and alkynes for interfacial step growth "click" polymerizations

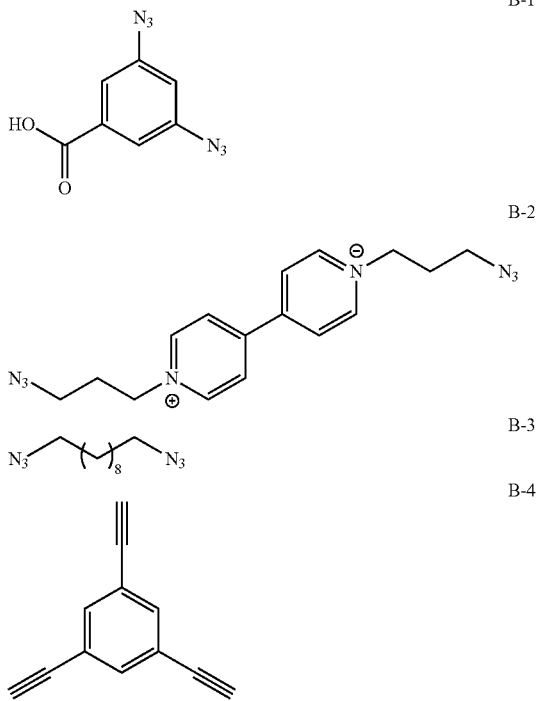

In one attempt, interfacial CuAAC was performed with a water soluble di-functional azide and an organic soluble tri-functional alkyne in the presence of an organic soluble Cu(I) catalyst (FIG. 7). Initially, after the immiscible monomer solutions met, no solid formed at the interface (FIG. 7B, left to right), however, after 24 hours a solid was present at the interface. When the solid was removed from the reaction and washed with THF, the solid did not dissolve. This indicates that cross-linking has occurred. However, the polymerization resulted in a powder, instead of a membrane.

To aid in the design of future monomers and experimental setup, it is important to understand why a powder formed instead of the desired membrane. The initial hypothesis is that the monomers are not soluble enough in their respective layers, therefore only a low concentration of monomers could be reacted. This could lead to a slow reaction rate and incomplete polymerization. By increasing the solubility of the monomers, the concentration of monomers in solution can be increased, thus the reaction rate will increase, and the polymer will reach a higher molecular weight before precipitation. This hypothesis led to the second interfacial polymerization, in which a more water soluble diazide was used. However, the results were similar to the first reaction, with an insoluble powder forming after 24 hours (FIG. 8).

The second hypothesis is that the triazole moiety is poorly soluble, and once a certain degree of conversion to triazoles is reached, the polymer precipitates and stops further polymerization. Without wishing to be bound by any theory, it is postulated that this could be happening when only small oligomers have formed, creating a powder. It was thought that by decreasing the number of triazole linkages, the polymer would remain soluble longer and larger polymers would form. To test this hypothesis, longer carbon chains were used between each triazole formed in the polymerization. (FIG. 9)

Each polymerization consists of three components (2 monomers and the Cu(I) catalyst). Since both organic and aqueous Cu(I) sources are available, both aqueous and organic azides and alkynes can be used in this reaction, which is unlike normal interfacial polymerization where each monomer must be in its respective layer. This leads to a very large pool of azide and alkyne monomers that can be synthesized for use in this reaction.

Example 8: Polymerization on Solid Metal Support

Membrane supports can be fabricated out of metal oxides (e.g., CuO, ZnO, and others) using conventional membrane fabrication techniques. Here, the metal oxide can be chosen as a catalyst for a polymerization or crosslinking reaction. An example crosslinking reaction that can be catalyzed by the membrane support is shown in FIG. 10. After the support is dipped in the polymer solution, the composite membrane can be heated to initiate the crosslinking reaction.

In one specific example, a tertrazole-functionalized PIM-1 blend containing both azide and alkyne groups or a diazide or dialkyne small molecule cross-linker was dissolved into THF and cast onto a copper plate. Cross-linking took place, catalyzed by the copper plate. The solvent was allowed to dry, and the cross-linked film-copper composite was heated dried at 50° C. in a vacuum oven.

This method was extended to form testable membranes by using CuO hollow fiber supports (FIG. 10B). In one specific example, a tertrazole-functionalized PIM-1 blend containing both azide and alkyne groups or a diazide or dialkyne small molecule cross-linker was dissolved into chloroform. In this case, the CuO hollow fiber was dipped into the polymer blend solution where the CuO catalyzed cross-linking at the surface of the fiber. After the solvent was removed, the fiber was rinsed with chloroform, THF, methanol, and hexanes and then dried at 50° C. in a vacuum oven. A 0.5 wt % solution of azide or alkyne-functionalized PIM-1 and small molecule cross-linker and no added reducing agent gave the best result.

Scheme 8: representative linkers and small molecule cross-linkers

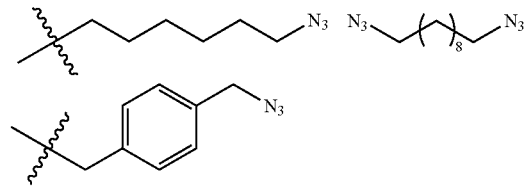

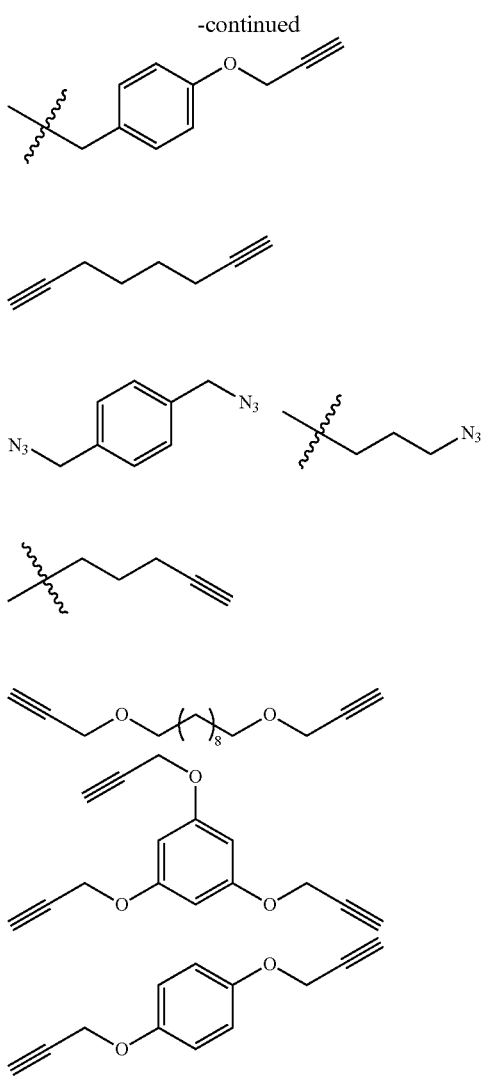

Example 9: Anchoring on a Ceramic Surface

Figure 12:
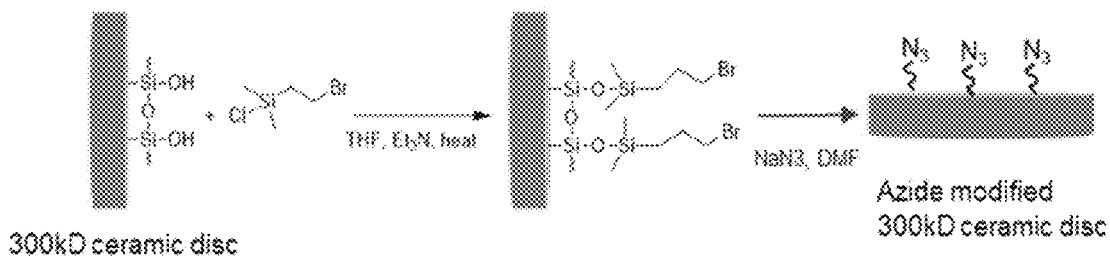
FIG. 12 is a schematic illustration of the functionalization of ceramic disc with azide groups.

Ceramic discs with various oxides on the surface were functionalized to install chemical reaction partners with functionalized polymers. For instance, a 300 kD MWCO ceramic membrane disc with a nominal pore size of approximately 15 nm with a $ZrO_2$ membrane layer and a $TiO_2$ support layer surface was used. The ceramic disc can be pretreated with other inorganic oxide layers, for example $SiO_2$, $Al_2O_3$ layers. The surface functional group, e.g. Ti—OH, Si—OH, Al—OH groups were first converted into reactive azide functional groups via a 2-step reaction (FIG. 12).

Figure 13:
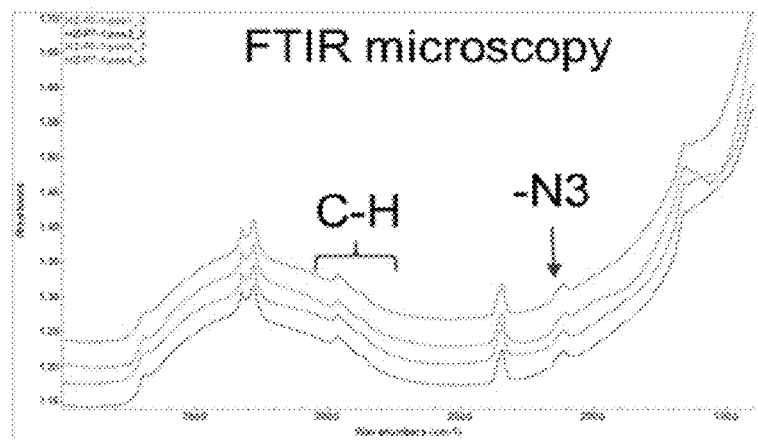
FIG. 13 shows FTIR microscopy spectra of azide modified ceramic disc, showing the desired alkyl and azide IR bands. Spectra were taken from different regions of ceramic disc.

First, 2-bromoethyldimethylchlorosilane was reacted with surface functional groups on ceramic surface, and the end-bromide functional groups were converted to azides by nucleophilic attack of sodium azide. The surface functionalization was confirmed by FTIR microscopy as shown in FIG. 13. FTIR microscopy spectra are quite similar at different regions of ceramic disc, showing the even modification of ceramic disc with azide functional groups.

Figure 14:
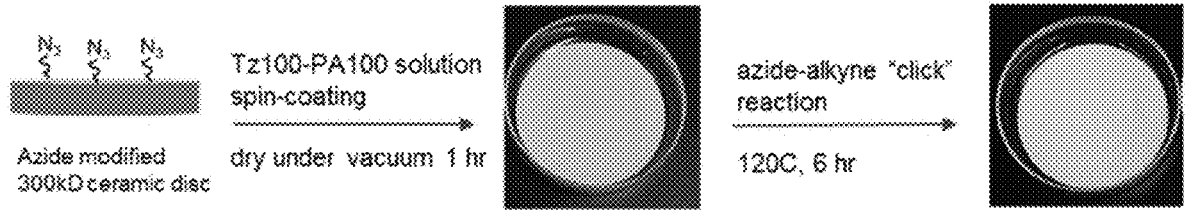
FIG. 14 is a schematic illustration of a coating and click reaction process according to an embodiment of the disclosure.
Figure 15:
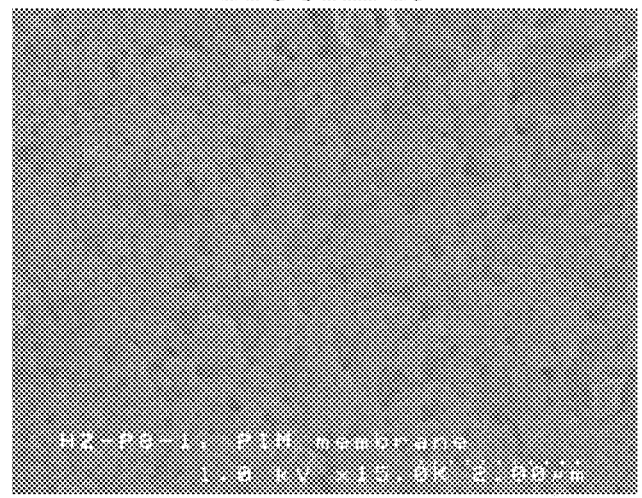
FIG. 15 is a SEM image of a coated membrane according to an embodiment of the disclosure.

As shown in FIG. 14, a solution of azide functionalized porous polymer Tz100-PA100 (FIG. 3A) in THF solution at 0.1 g/mL was then spin-coated on ceramic disc at 3000 rpm for 2 min. The resulting disc was then dried in fume hood for 3 hours and then under vacuum for 3 hours before baking at 120° C. for 6 hours under inert atmosphere. The resulting membrane was then washed with THF for 4 hours before drying under vacuum. SEM image showed even coating of polymers on surface (FIG. 15).

Example 10: Evaluation of Membrane Permeability

Figure 16:
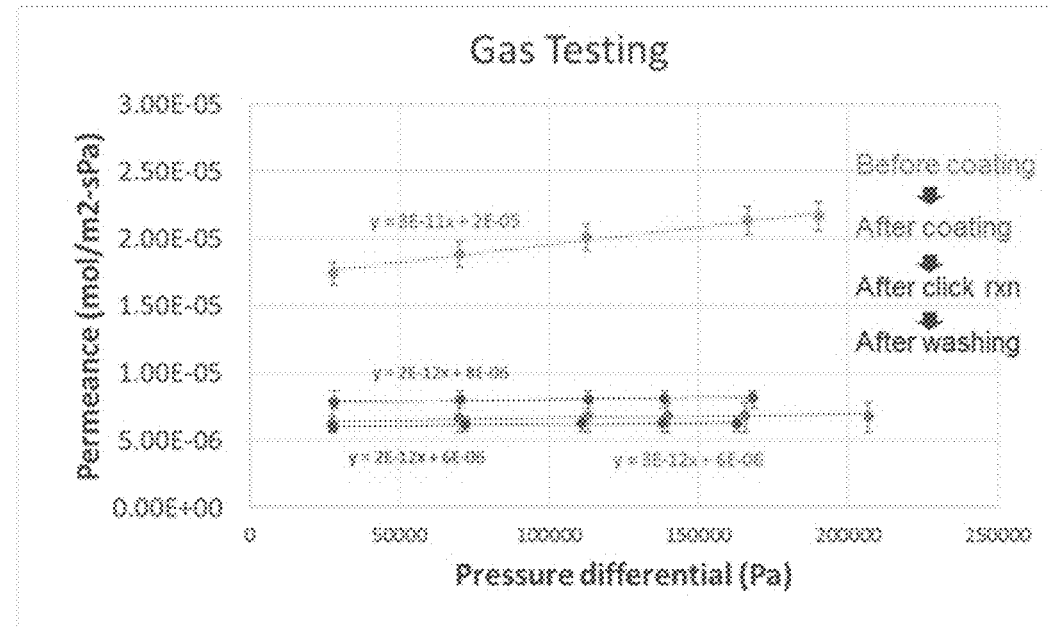
FIG. 16 depicts gas testing permeance of ceramic membranes at different steps of fabrication process.

Nitrogen gas testing was used to evaluate the membrane performance. As seen in FIG. 16, the slope of the permeance plot dropped significantly after initial polymer coating, which indicates a significant decrease in membrane defects. No significant change in permeance and slope show in the last steps of fabrication, indicating minimum material loss and change of polymer coating.

Figure 17:
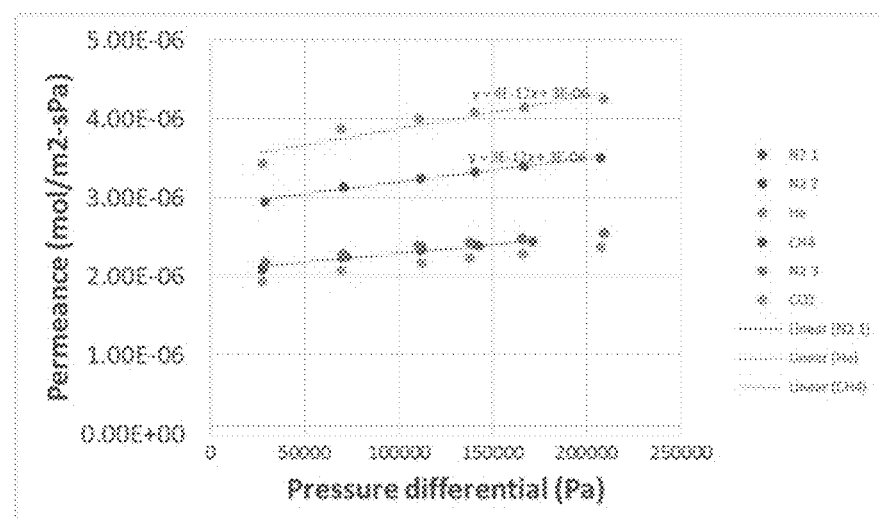
FIG. 17 depicts gas testing permeance of ceramic membranes for multi-gas testing.

Further study of the supported membrane with multi-gas (nitrogen, helium, methane and carbon dioxide) revealed different selectivity towards different gases (FIG. 17).

Figure 18:
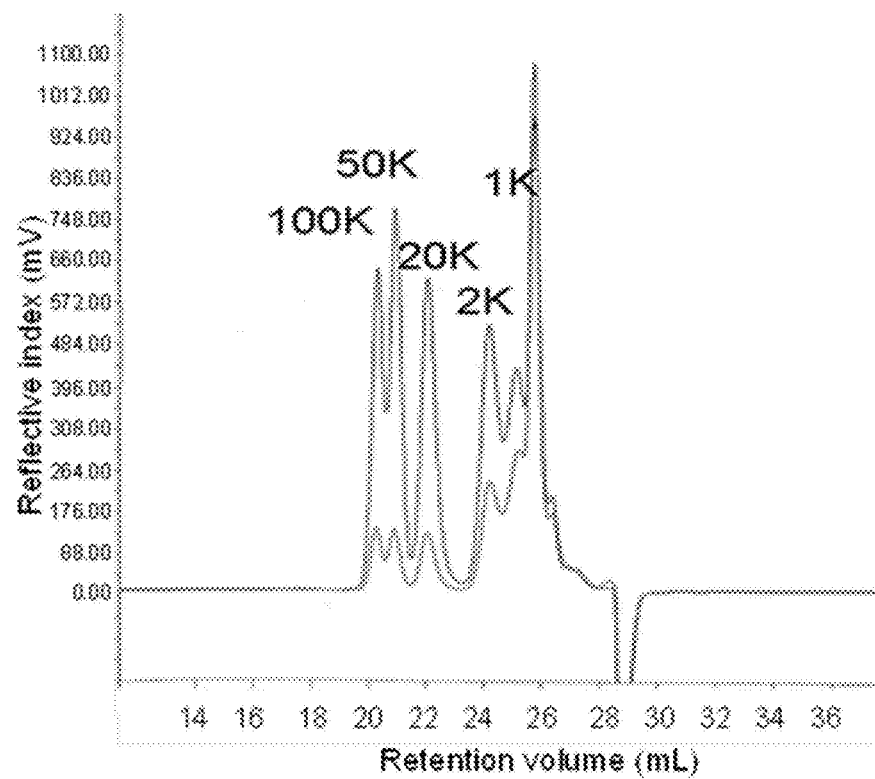
FIG. 18 depicts GPC traces of polystyrenes before (original blend) and after (permeate) passing through porous supported membrane.

To study the molecular separation properties of the supported porous membranes, the membrane rejection of polystyrene with different molecular weights were studied. In this study, polystyrenes with narrow molecular distribution but different molecular weights (weight average molecular weights of 100 kDa, 50 kDa, 20 kDa, 2 kDa and 1 kDa) were dissolved in cyclohexane at 0.1 g/L. This polymer mixture solution was then used to pass through porous supported membrane in a testing cell at a pressure of 150 Psi. First permeant (10 g) was collected in 6 hours for a disc area of 0.001734945 $m^2$. GPC traces of polystyrenes before and after passing through porous supported membrane showed molecular weight based rejection of polystyrene above 2 kDa. (FIG. 18).

Example 11

A series of PIM-like polymers has been synthesized using Buchwald-Hartwig coupling, all containing a spirobifluorene core and varying diamine structures. The polymers synthesized are shown in Scheme 8. Upon synthesis, each material was tested for membrane forming properties followed by its separation abilities.

Scheme 9: series of amine-linked PIMs synthesized via Buchwald-Hartwig coupling

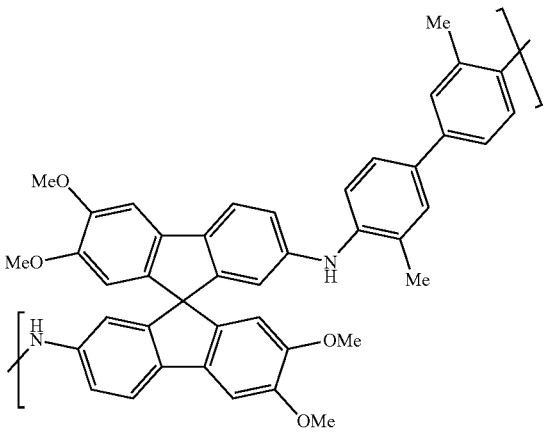

PIM-BADAS-1

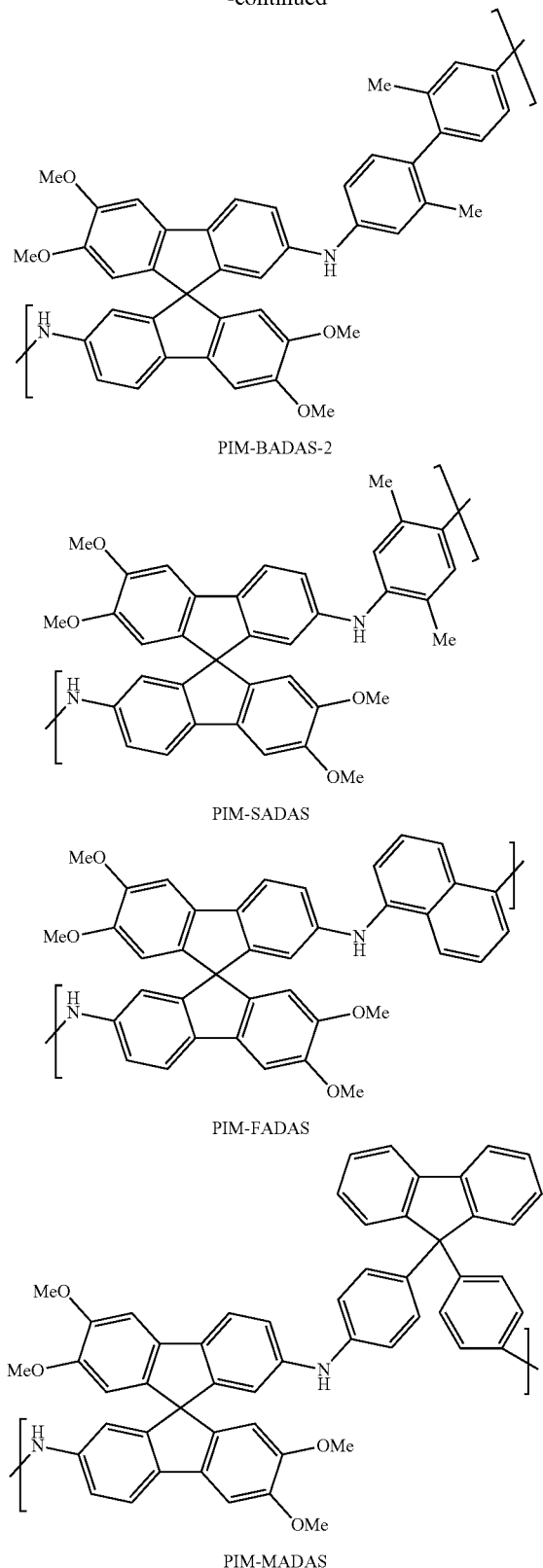

PIM-BADAS-2

PIM-SADAS

PIM-FADAS

PIM-MADAS

Films of these materials have been found to form readily but proved difficult to remove from the casting dish. Polymeric films are often removed by "floating" the film off the dish with a non-solvent (i.e. methanol), but in this case the films often remained adhered. Attempts to sonicate and peel the film free resulted in cracking. Additionally, these films often had small defects (bubbles, cracks, uneven coating, etc.) making this method of film formation undesirable.

To avoid these problems, efforts have shifted from forming free-standing films to forming films on a solid support. Forming thin-films on polymer supports has been explored through drop casting and spin coating polymer solutions onto the support. Observation of films made through these methods suggested spin coating to be the method that provides the most uniform and repeatable films. Many films have been successfully produced through this method and taken forward to separation testing.

Example 12

The membranes were spin coated on supports that contain longitudinal pores due to their high permeances, although some compaction of the TFC is expected to occur. The support fabricated through spinodal decomposition showed a permeance ($\geq 50$ L m$^{-2}$ h$^{-1}$ bar$^{-1}$) that was more than ten-fold higher than the permeance expected for the TFCs, where the thin film acts as the separating material (1-10 L m$^{-2}$ h$^{-1}$ bar$^{-1}$). Upon considering commonly used parameters, 0.5 mL of a 0.3 wt % polymer solution of PIM-BADAS-1, PIM-BADAS-2, PIM-SADAS, and Az-Tz$_{10}$-PIM (10% azide-functionalized tetrazole PIM-1) in THF were spin coated on to Matrimid® supports. A Matrimid® support was also spin coated with a mixture of equal volumes of 0.3 wt % azide-functionalized Tz$_{10}$-PIM and 0.3 wt % alkyne cross-linker. These were rotated at a speed of 1000 rpm for 60 seconds and the procedure was repeated to generate a '2-layer' film. The TFC with cross-linker was placed in a 1M organic Cu(I) solution overnight to catalyze the cross-linking. PIM-BADAS-1 was also spin coated to form a '3-layer film' on a commercially available PAN support (Sterlitech Corporation).

PIM-BADAS-1 on PAN was placed in a cross-flow cell with a feed of 1 mol % TIPB in toluene at 30 mL/min. An HPLC pump was used to circulate the feed and the pressure was initially mistakenly set at 15 bar then lowered to 10 bar within an hour and permeate was collected immediately and again, after 3 hours. Additional permeate was collected at least 15 hours after the pressure was changed in the experiment. FIG. 24 shows the permeance and rejection time plot at various applied pressures. The rejection was calculated by measuring the ratio of concentrations of the TIPB in the permeate and feed through gas chromatography (GC).

TFCs formed by spin coating PIM-BADAS-1, Az-Tz$_{10}$-PIM and a mixture of Az-Tz$_{10}$-PIM and an alkyne cross-linker on Matrimid® were placed in crossflow cells and tested with the same feed composition as above and a feed pressure of 15 bar. As shown in FIG. 24B, a higher rejection of TIPB was obtained compared to results using other PIM TFCs reported by Cook et al. (Cook, et al., "Roll-to-roll dip coating of three different PIMs for Organic Solvent Nanofiltration," *J. Membr. Sci.* (2018), 558, 52) at 30 bar with α-methylstyrene dimer as the solute. The rejection for PIM-BADAS-1/Matrimid® is also higher than what was obtained for PIM-BADAS-1/PAN membrane although there was a ten-fold decrease in permeance. It should be noted that no attempts were made to reduce the thickness of the PIM layers in the PIM-BADAS-1, Az-Tz10-PIM and crosslinked samples.

A decline in permeance with time is indicative of either membrane support compaction, membrane fouling, membrane aging, or a combination of the three. If membrane support compaction is strong enough to cause a decrease in permeance, the thin polymer film will no longer dominate the separation and the rejection of the solute is expected to decrease. Apart from a few outliers possibly due to instrument error, the rejection was stable between 35-38% and so, membrane compaction is disqualified. At the end of the experiment, the TFC membrane was retrieved and significant darkening of the active layer was noted and attributed to membrane fouling. The calculated rejection of TIPB (204.35 Da) falls at the higher end of the 18-45% range that was previously reported for the rejection of the larger α-methylstyrene dimer (236.35 Da) solute by PIM-1/PAN TFC.

Example 13

PIM-BADAS-1 on Matrimid® was also subject to a 7-component organic solvent mixture separation in cross-flow mode. The feed contained 1 mol % each of p-xylene, o-xylene, mesitylene, naphthalene, biphenyl and TIPB in toluene and was supplied at 20 mL/min at 10 bar. The resulting permeance (FIG. 25A) is comparable to the binary mixture result while the rejection of TIPB (FIG. 25B) jumps to about 80% after a 40+ hour period. Moreover, a slight rejection of mesitylene (MW 120.19 Da) was also recorded (FIG. 25B). Other solutes showed no rejection over the 66 hour testing period as shown in the following table:

rejection is negatively dependent on permeance as a result of nanoscopic defects in the thin films. Under the same spin coating conditions, small changes in environmental factors like humidity and temperature as well as surface pore size of the support can affect the quality of the thin film formed.

Example 14

A solution of PIM was prepared by dissolving PIM polymers in chloroform at 0.8 wt % and then filtrated using PTFE filter (FGLP04700, Merck) with the pore size of 200 nm. The coating was conducted on a roll-to-roll pilot line (RK Print, UK) using crosslinked polyetherimide membrane (average pore size: 9 nm) with a web width of 30 cm at a casting speed of 1.5 m/min, and then dried at 55° C. in an air-convection dryer. All of the process was conducted continuously.

Figure 27A:
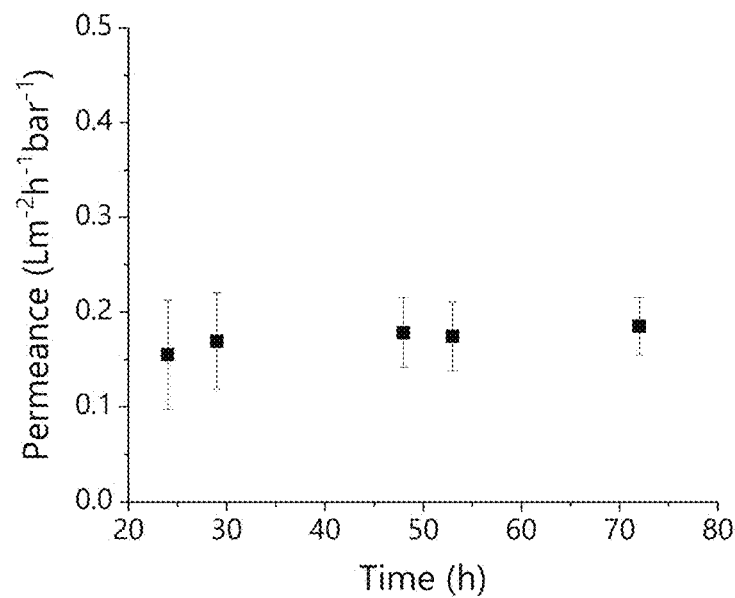
FIG. 27A and FIG. 27B are permeance and rejection over time plots, respectively, of TIPB for PIM-BADAS-1 coated on PEI under a binary feed of 1 mol % TIPB in toluene at 15 bar.
Figure 27B:
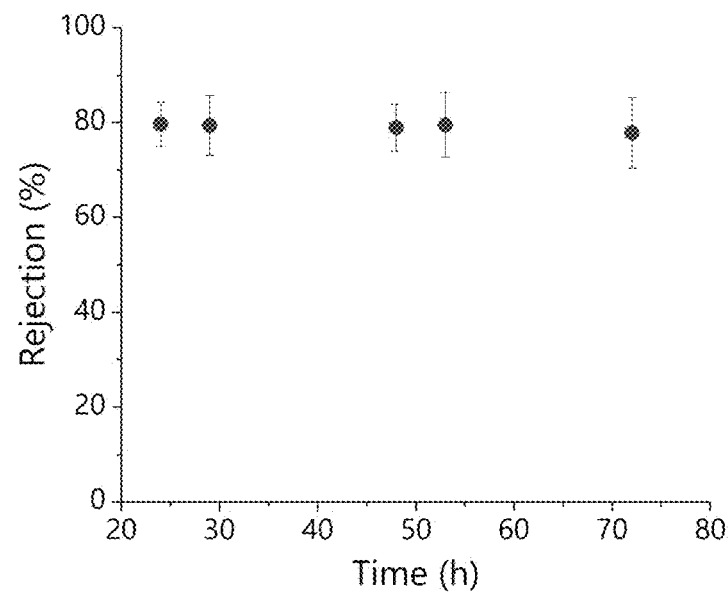

Three coupons were obtained from the roll and tested in a cross flow set up under 1 mol % TIPB/toluene at 15 bar. The resulting permeance and rejection of TIPB agree with what was obtained in Example 13 as shown in FIGS. 27A and B. Thus, we can establish that the TIPB rejection of a defect-free PIM-BADAS-1 membrane lies around 80% for a dilute mixture of solutes in toluene. These samples were

|  | p-Xylene | o-Xylene | Mesitylene |
|---|---|---|---|
| Structure | H₃C—⟨⟩—CH₃ | CH₃, CH₃ (o-xylene) | (mesitylene structure) |
| MW (g/mol) | 106.17 | 106.17 | 120.19 |
| Rejection (%) | −3 | 0 | 12 |

|  | Naphthalene | Biphenyl | TIPB |
|---|---|---|---|
| Structure | (naphthalene) | (biphenyl) | (TIPB) |
| MW (g/mol) | 128.17 | 154.21 | 204.36 |
| Rejection (%) | −5 | −2 | 83 |

Steady-State Rejection of the Solutes in the 7-Component Mixture Feed for PIM-BADAS-1 on Matrimid®

The low or no rejection of most species below MW of 200 and high rejection of TIPB indicates the membrane has a MWCO of about 200 Daltons. The higher rejection of mesitylene (a branched molecule) versus naphthalene (a linear molecule) both with similar molecular weight shows that the membrane also separates based on the shape of the molecule when the size (as represented by the MW) of the molecules are the same.

Figure 26:
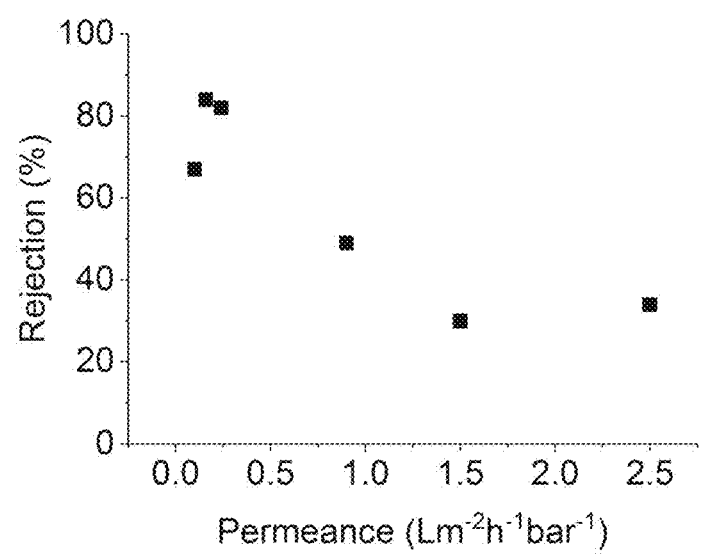
FIG. 26 is a rejection versus permeance plot of data recorded for different samples of TIPB for PIM-BADAS-1 on Matrimid® in a binary feed of 1 mol % TIPB in toluene.
Figure 28:
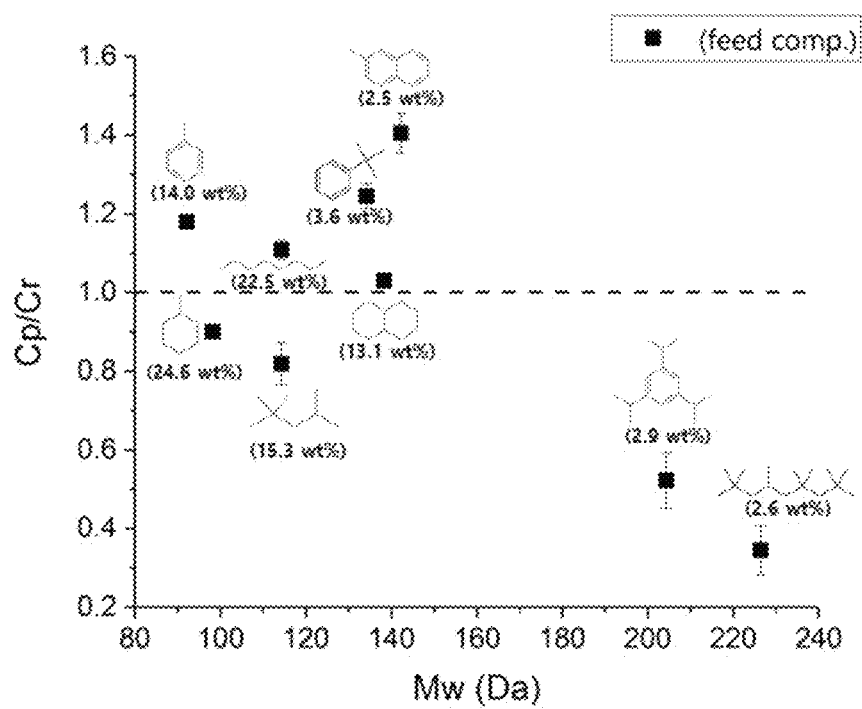
FIG. 28 displays the ratio of the concentration in the permeate to the retentate against the molecular weight of the chemical for a complex hydrocarbon mixture fed to PIM-BADAS-1 TFCs coated on PEI at 40 bar.

For several PIM-BADAS-1/Matrimid® supports fabricated in the same manner, a range of permeances and rejections of TIPB from toluene were obtained and are collectively shown in FIG. 26. It is hypothesized that the further investigated for the separation of a complex, multi-component mixture that resembled a real crude oil cut. A feed containing nine hydrocarbon components at concentrations as listed in FIG. 28 resulted in respectable separation factors (Table 1, below) amongst inter-class as well as intra-class molecules at a permeance of 0.02 Lm$^{-2}$ h$^{-1}$ bar$^{-1}$. There is a clear size-based exclusion of molecules larger than 200 Da whereas below 150 Da, aromatic molecules are preferentially transported through the membrane. This is especially true for the polyaromatic, 1-methylnapthalene. These results align with the expectations derived from the separations of dilute, feed mixtures that are listed in previous examples.

TABLE 1

Separation factors of selected groups of a complex, hydrocarbon mixture using PIM-BADAS-1 TFC membranes coated on PEI.

| | Separation Factors |
|---|---|
| aromatic/aromatic toluene/TIPB | 2.3 |
| aromatic/branched aliphatic toluene/isocetane | 3.4 |
| cyclic aliphatic/branched aliphatic methylcyclohexane/isocetane | 2.6 |
| linear/branched aliphatic n-octane/isocetane | 3.2 |

Example 15

Figure 29A:
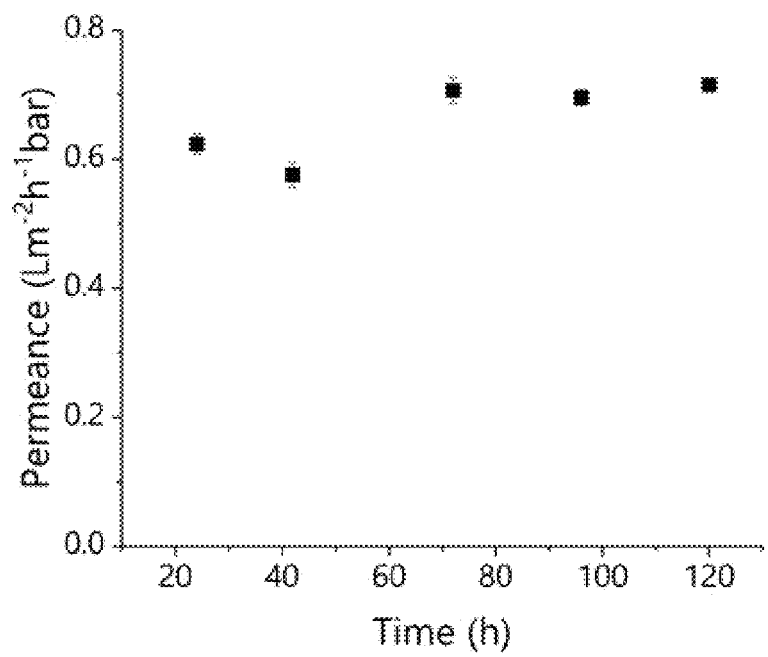
FIG. 29A and FIG. 29B are permeance and rejection over time plots, respectively, of TIPB for PIM-SADAS coated on PEI under a binary feed of 1 mol % TIPB in toluene at 15 bar.
Figure 29B:
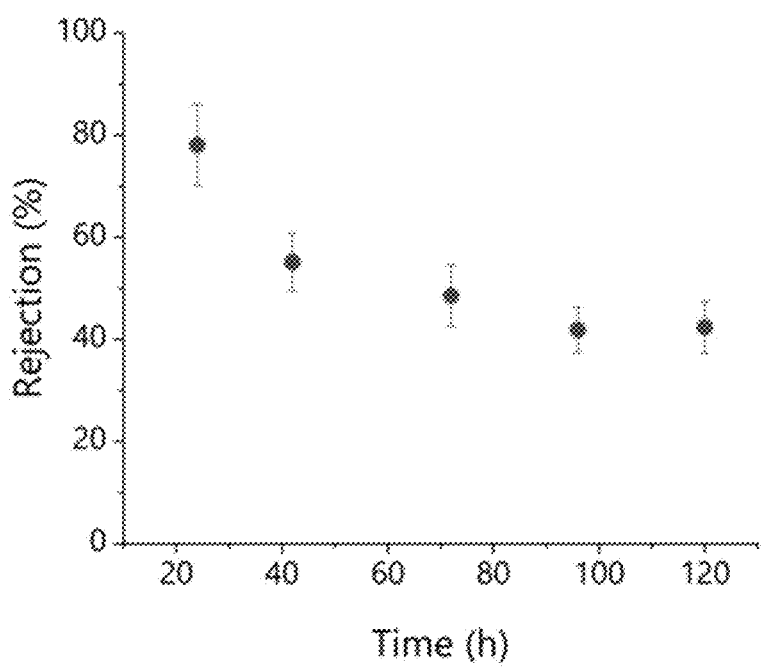

Following this, PIM-SADAS was blade coated on a polyetherimide (PEI) sheet with a non-woven polyester backing using a 1-mil blade and a 2 wt. % polymer dope in chloroform that was cooled to 4° C. A 1 mol % TIPB/toluene solution was fed to three coupons from this sheet under 15 bar in a cross flow system. As shown in FIG. 29B, the results indicate that while PIM-SADAS initially exhibited similar performance to PIM-BADAS-1 with ~80% rejection of TIPB, the separation efficiency decreased over time. This could be due to the partial solubility of the polymer that was visually observed when the feed solution started to impart a slight pink tinge. Upon $^1$H NMR analysis, no polymer was detected in the spent feed solution, suggesting that even small amounts of dissolution of the polymer may be sufficient to decrease the efficacy of the membrane. In such a case, one could maintain the separation performance temporally by crosslinking the polymer.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings. Accordingly, the present description is intended to embrace all such alternatives, modifications, and variances which fall within the scope of the appended claims.

All patents, applications, publications, test methods, literature, and other materials cited herein are hereby incorporated by reference in their entirety as if physically present in this specification.

Additional embodiments are articulated below.

Embodiment 1

A method of preparing a cross-linked polymer membrane comprising the steps of:

a) providing a first polymer comprising a first functional group selected from —N$_3$, —C≡CH, C≡C—R', —C≡N, —(C═O)—H, —SH, —CH═CH$_2$, —CH═CHR', —NH$_2$, —NR'—NHR', and —O—NHR' and a second polymer comprising a second functional group selected from —N$_3$, —C≡CH, C≡C—R', —C≡N, —(C═O)—H, —SH, —CH═CH$_2$, —CH═CHR', —NH$_2$, —NR'—NHR', and —O—NHR' wherein R' is selected from substituted or unsubstituted alkyl, substituted or unsubstituted heteroalkyl, substituted or unsubstituted aryl, substituted or unsubstituted heteroaryl, —CN, —CO$_2$R", —(C═O)—N(R")$_2$, and —(C═O)—R", and R" is independently at each occurrence selected from H, substituted or unsubstituted alkyl, substituted or unsubstituted heteroalkyl, substituted or unsubstituted aryl, and substituted or unsubstituted heteroaryl, and wherein the first functional group and the second functional group are capable of irreversibly reacting with each other to form a covalent connection;

b) fabricating the first polymer and the second polymer into a desired membrane;

c) crosslinking the fabricated membrane of step b) by reacting the first functional group and the second functional group to form the covalent connection, thus obtaining the cross-linked polymer membrane.

Embodiment 2

The method of embodiment 1, wherein the first polymer and the second polymer each have a chemical structure:

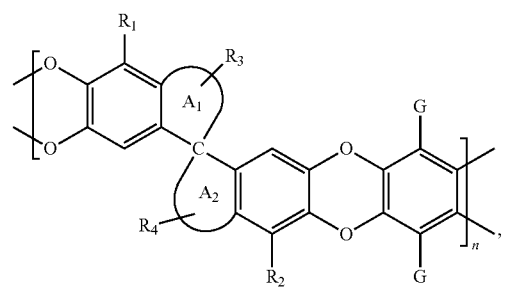

wherein: the carbon indicated by "C" denotes a spiro-carbon;

A$_1$ is selected from

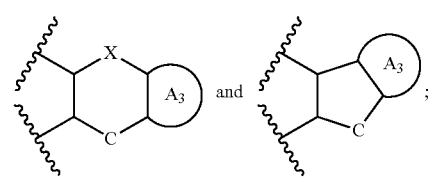

$A_2$ is

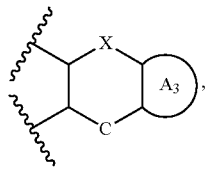

X is independently at each occurrence selected from —$CR_6$—, —O—, —S—, —$N(R_6)_2$, —C=O, —$C=NR_6$, —$C=N-N(R_6)_2$, and $C=N-OR_6$;

$R_1$, $R_2$, $R_3$, and $R_4$ are each independently selected from H and Y—Z;

$R_6$ is independently at each occurrence selected from H, substituted or unsubstituted alkyl, substituted or unsubstituted heteroalkyl, substituted or unsubstituted aryl, and substituted or unsubstituted heteroaryl;

$A_3$ is a selected from substituted or unsubstituted $C_5$-$C_6$ aryl, substituted or unsubstituted $C_5$-$C_6$ heteroaryl, substituted or unsubstituted $C_5$-$C_6$ cycloalkyl and substituted or unsubstituted $C_5$-$C_6$ cyclic heterocycloalkyl;

Y is independently absent or selected from substituted or unsubstituted alkyl, substituted or unsubstituted aryl, —NH—(C=O)—; =NO—$C_{1-6}$ alkyl-; and —(C=O)-phenyl-;

Z is the functional group selected from —$N_3$, —C≡CH, C=C—R', —C≡N, —(C=O)—H, —SH, and —CH=$CH_2$;

R' is independently at each occurrence selected from substituted or unsubstituted alkyl, substituted or unsubstituted heteroalkyl, substituted or unsubstituted aryl, substituted or unsubstituted heteroaryl, —CN, —$CO_2R"$, —(C=O)—N(R")$_2$, and —(C=O)—R";

R" is selected from H, substituted or unsubstituted alkyl, substituted or unsubstituted heteroalkyl, substituted or unsubstituted aryl, and substituted or unsubstituted heteroaryl;

G is selected from Y—Z, halogen, —CN, substituted or unsubstituted aryl, and substituted or unsubstituted heteroaryl; and n is an integer from 5 to 100,000.

Embodiment 3

The method of embodiment 2, wherein the first polymer comprises the first functional group selected from —$N_3$ and —C≡CH, and the second polymer comprises the second functional group selected from —$N_3$ and —C≡CH, wherein when the first functional group is —$N_3$, the second functional group is —C≡CH, and when the first functional group is —C≡CH, the second functional group is —$N_3$.

Embodiment 4

The method of embodiment 1, wherein the desired membrane has a form factor selected from hollow fiber membranes, spiral wound membranes, plate-and-frame membranes, coated monoliths, tubes, and discs.

Embodiment 5

The method of embodiment 4, wherein the desired membrane form factor is a hollow fiber membrane.

Embodiment 6

The method of embodiment 1, wherein the desired membrane has a morphology selected from an integrally-skinned asymmetric morphology or a thin film composite morphology.

Embodiment 7

The method of embodiment 1, wherein the first polymer and the second polymer are fabricated into the desired membrane using one or more fabrication techniques selected from dry jet-wet quench solution spinning, slip casting, dip coating, blade coating, spin casting, chemical vapor deposition, interfacial polymerization, tape casting, and melt extrusion.

Embodiment 8

The method of embodiment 1, wherein the step b) of fabricating the first polymer and the second polymer into the desired membrane further comprises exchanging solvent and drying the fabricated membrane.

Embodiment 9

The method of embodiment 1, wherein the step c) of crosslinking the fabricated membrane of step b) comprises subjecting the fabricated membrane to heat, UV-visible light, a dehydrating agent, and/or a catalyst to react the first functional group and the second functional group.

Embodiment 10

The method of embodiment 1, wherein the step c) of crosslinking the fabricated membrane of step b) comprises submersing the fabricated membrane in a nonsolvent solution comprising a catalyst for the reaction between the first functional group and the second functional group.

Embodiment 11

The method of embodiment 10, wherein the step c) further comprises exchanging solvent.

Embodiment 12

A method of preparing a cross-linked polymer membrane according to Scheme 1:

Scheme 1
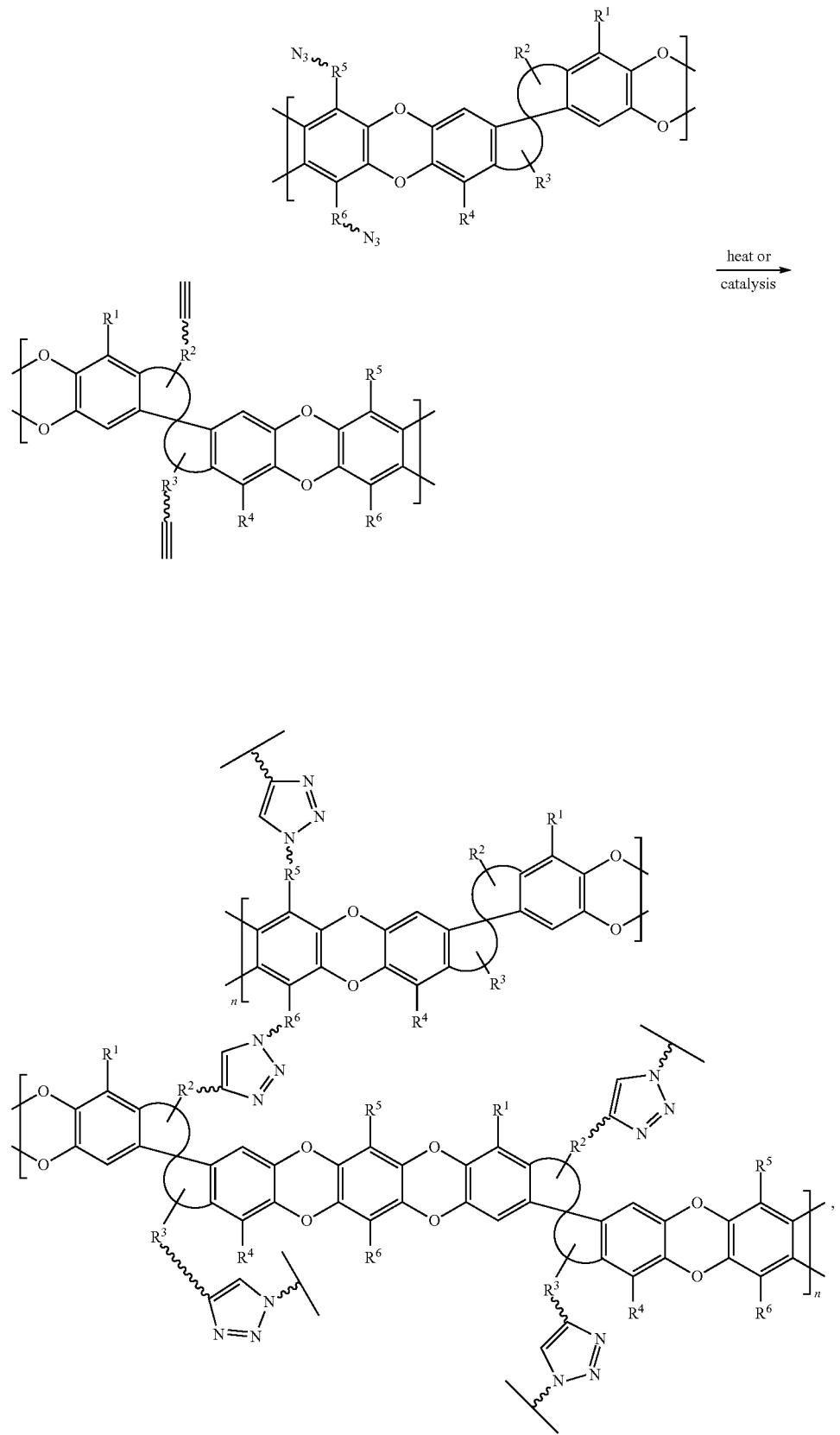

wherein $R_1$, $R_2$, $R_3$, $R_4$, $R_5$, and $R_6$ are each independently at each occurrence selected from H, substituted or unsubstituted alkyl, substituted or unsubstituted heteroalkyl, substituted or unsubstituted aryl, and substituted or unsubstituted heteroaryl, the method comprising the steps of:

a) providing a first polymer comprising a first functional group —$N_3$ and a second polymer comprising a second functional group —C≡CH, b) fabricating the first polymer and the second polymer into a desired membrane;

c) crosslinking the fabricated membrane of step b) by reacting the first functional group —$N_3$ and the second functional group —C≡CH to form a triazole connection, thus obtaining the cross-linked polymer membrane.

Embodiment 13

The method of embodiment 12, wherein step c) of crosslinking the fabricated membrane of step b) comprises heating the fabricated membrane to between about room temperature and about 200° C. to react the first functional group and the second functional group.

Embodiment 14

The method of embodiment 12, wherein the step c) of crosslinking the fabricated membrane of step b) comprises submersing the fabricated membrane in a nonsolvent solution comprising a copper catalyst for the reaction between the first functional group —$N_3$ and the second functional group —C≡CH.

Embodiment 15

The method of embodiment 14, wherein the nonsolvent solution comprising a copper catalyst is a solution of copper (I) salt.

Embodiment 16

The method of embodiment 15, wherein the copper(I) salt is selected from copper(I) ascorbate, copper(I) iodide, copper(I) bromide, copper(I) chloride, copper(I) acetate, $L_n$Cu (I) X, where L is selected from phosphine, amine, and pyridyl, n is an integer from 0 to 4, and X is selected from Cl, Br, I, OAc, and $BF_4$.

Embodiment 17

The method of embodiment 15, wherein the copper(I) salt is a combination of Cu(II) salt selected from $CuSO_4$, $Cu(OAc)_2$, $CuBr_2$, $CuCl_2$ and sodium ascorbate.

Embodiment 18

The method of embodiment 14 or 15, wherein the nonsolvent solution comprising a copper catalyst is a solution of copper (I) ascorbate.

Embodiment 19

A method of preparing a cross-linked polymer membrane according to Scheme 2:

Scheme 2

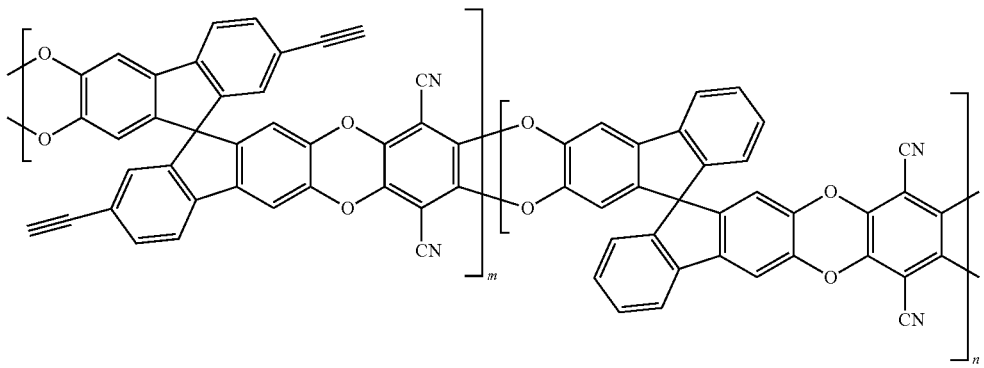

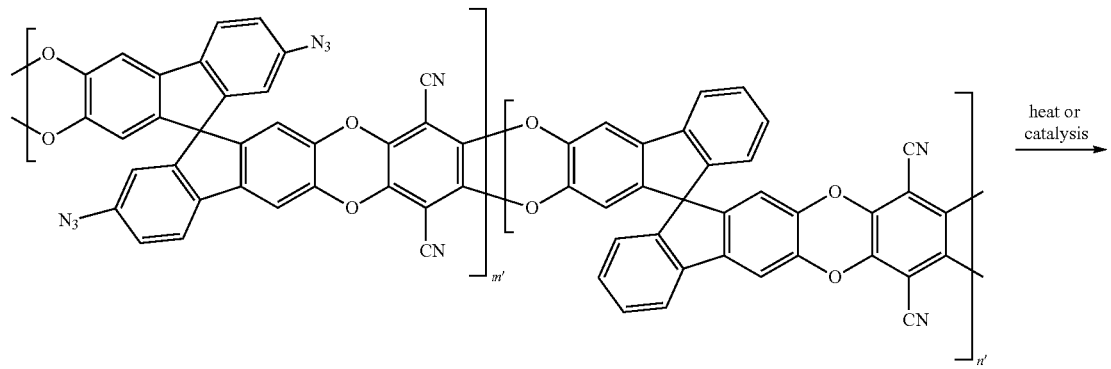

-continued

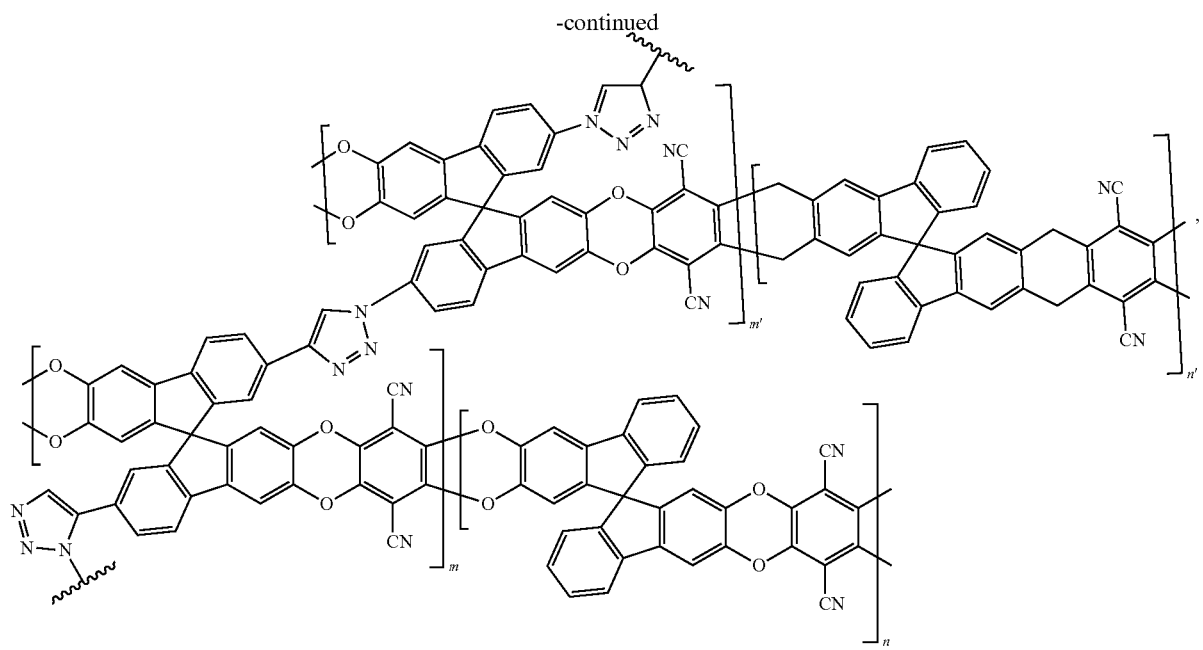

wherein n, n', m, and m' are each independently an integer from 5 to 100,000, the method comprising the steps of:

a) providing a first polymer comprising a first functional group —N$_3$ and a second polymer comprising a second functional group —C≡CH, b) fabricating the first polymer and the second polymer into a desired membrane;

c) crosslinking the fabricated membrane of step b) by reacting the first functional group —N$_3$ and the second functional group —C≡CH to form a triazole connection, thus obtaining the cross-linked polymer membrane.

Embodiment 20

The method of embodiment 19, wherein the step b) of fabricating the first polymer and the second polymer into a desired membrane is performed in a solvent.

Embodiment 21

The method of embodiment 19, wherein the step c) of crosslinking the fabricated membrane of step b) comprises submersing the fabricated membrane in a nonsolvent solution comprising a copper catalyst for the reaction between the first functional group —N$_3$ and the second functional group —C≡CH.

Embodiment 22

The method of embodiment 21, wherein the nonsolvent solution comprising a copper catalyst is a solution of copper ascorbate.

Embodiment 23

A method of preparing a cross-linked polymer membrane comprising the steps of:

a) providing a polymer comprising a first functional group selected from —N$_3$, —C≡CH, C≡C—R', —C≡N, —(C=O)—H, —SH, —CH=CH$_2$, —CH=CHR', —NH$_2$, —NR'—NHR', and —O—NHR', wherein R' is selected from substituted or unsubstituted alkyl, substituted or unsubstituted heteroalkyl, substituted or unsubstituted aryl, substituted or unsubstituted heteroaryl, —CN, —CO$_2$R", —(C=O)—N(R")$_2$, and —(C=O)—R", and R" is independently at each occurrence selected from H, substituted or unsubstituted alkyl, substituted or unsubstituted heteroalkyl, substituted or unsubstituted aryl, and substituted or unsubstituted heteroaryl, and b) fabricating the polymer into a desired membrane;

c) contacting the fabricated membrane of step b) with a compound comprising a second functional group selected from —N$_3$, —C≡CH, C≡C—R', —C≡N, —(C=O)—H, —SH, —CH=CH$_2$, —CH=CHR', —NH$_2$, —NR'—NHR', and —O—NHR', wherein the second functional group is capable of irreversibly reacting with the first functional group to form a covalent connection;

d) crosslinking the fabricated membrane of step b) with the compound of step c) by reacting the first functional group and the second functional group to form the covalent connection, thus obtaining the cross-linked polymer membrane.

Embodiment 24

The method of embodiment 23, wherein the polymer comprising the first functional group has the following chemical structure:

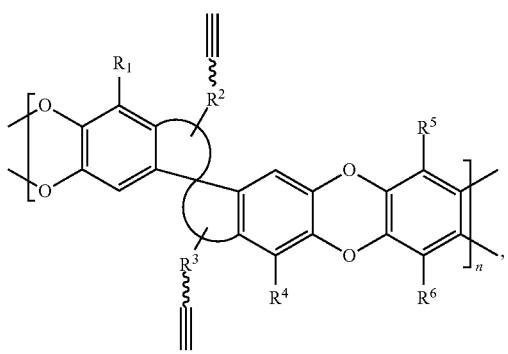

wherein $R_1$, $R_2$, $R_3$, $R_4$, $R_5$, and $R_6$ are each independently at each occurrence selected from H, substituted or unsubstituted alkyl, substituted or unsubstituted heteroalkyl, substituted or unsubstituted aryl, and substituted or unsubstituted heteroaryl, and n is an integer from 5 to 100,000.

Embodiment 25

The method of embodiment 23, wherein the second functional group is —$N_3$.

Embodiment 26

The method of embodiment 23, wherein the compound comprising the second functional group has a structure according to formula:

$N_3$—R—$N_3$, wherein R is selected from a substituted or unsubstituted alkyl, substituted or unsubstituted heteroalkyl, substituted or unsubstituted aryl, and substituted or unsubstituted heteroaryl.

Embodiment 27

The method of embodiment 23, wherein step c) of contacting the fabricated membrane of step b) with a compound comprising the second functional group is performed by submersing the fabricated membrane in a solution of the compound comprising the second functional group.

Embodiment 28

A method of preparing a cross-linked polymer membrane according to Scheme 3:

Scheme 4

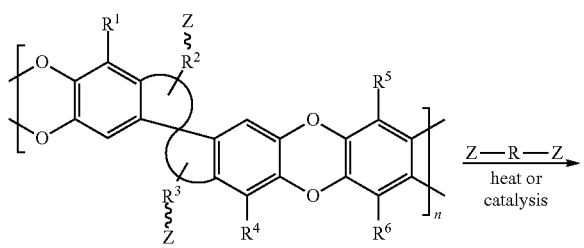

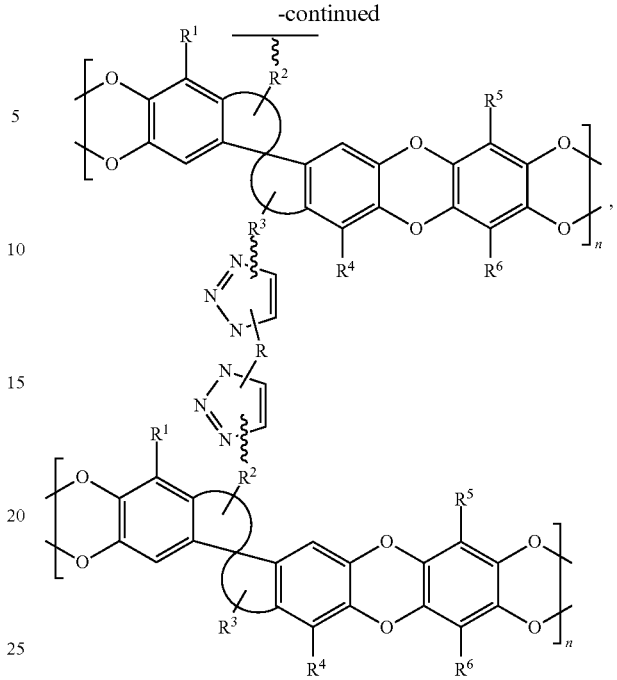

wherein Z is a group selected from —$N_3$ and —C≡CH,

R is selected from a substituted or unsubstituted alkyl, substituted or unsubstituted heteroalkyl, substituted or unsubstituted aryl, and substituted or unsubstituted heteroaryl, and wherein $R_1$, $R_2$, $R_3$, $R_4$, $R_5$, and $R_6$ are each independently at each occurrence selected from H, substituted or unsubstituted alkyl, substituted or unsubstituted heteroalkyl, substituted or unsubstituted aryl, and substituted or unsubstituted heteroaryl, and n is an integer from 5 to 100,000, the method comprising the steps of:

a) providing a polymer comprising a functional group Z selected from —$N_3$ and —C≡CH, b) fabricating the polymer into a desired membrane;

c) contacting the fabricated membrane of step b) with a compound comprising a functional group Z selected from —$N_3$ and —C≡CH, wherein if the polymer functional group of step (a) is —$N_3$, then the compound functional group is —C≡CH, and if the polymer functional group of step (a) is —C≡CH, then the compound functional group is —$N_3$;

d) crosslinking the fabricated membrane of step b) with the compound of step c) comprising the functional group by reacting the functional group —C≡CH with the functional group —$N_3$ to form a triazole connection, thus obtaining the cross-linked polymer membrane.

Embodiment 29

The method of embodiment 28, wherein step d) of crosslinking the fabricated membrane of step b) with the compound of step c) comprises heating to from about room temperature to about 200° C.

Embodiment 30

The method of embodiment 28, wherein the step d) of crosslinking the fabricated membrane of step b) with the compound of step c) comprises submersing the fabricated membrane in a solution comprising the compound of step c) and a catalyst for initiating the reaction between the functional group —C≡CH and the functional group —$N_3$.

Embodiment 31

The method of embodiment 28, wherein the catalyst is a copper catalyst.

Embodiment 32

The method of embodiment 31, wherein the copper catalyst is a copper(I) salt.

Embodiment 33

The method of embodiment 32, wherein the copper(I) salt is selected from copper(I) ascorbate, copper(I) iodide, copper(I) bromide, copper(I) chloride, copper(I) acetate, and $L_nCu(I) X$, where L is selected from phosphine, amine, and pyridyl, n is an integer from 0 to 4, and X is selected from Cl, Br, I, OAc, and $BF_4$.

Embodiment 34

The method of embodiment 32, wherein the copper(I) salt is a combination of Cu(II) salt selected from $CuSO_4$, $Cu(OAc)_2$, $CuBr_2$, $CuCl_2$ and sodium ascorbate.

Embodiment 35

The method of embodiments 31-34, wherein the copper catalyst is copper (I) ascorbate.

Embodiment 36

The method of embodiment 28 according to Scheme 4:

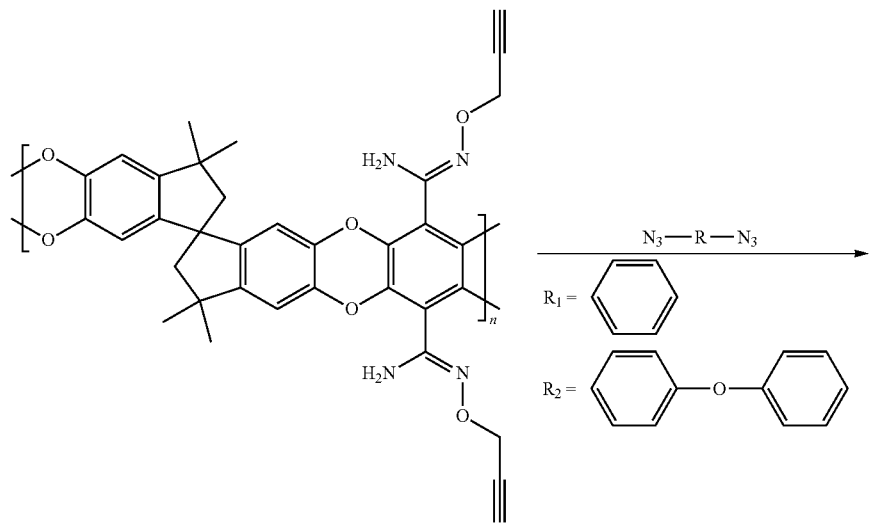

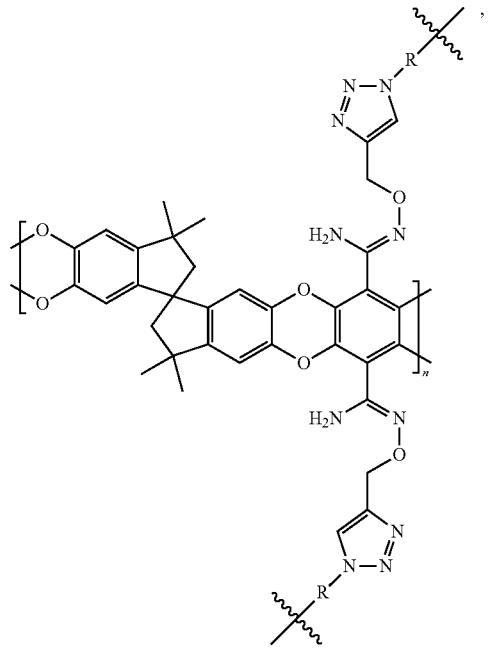

wherein n is an integer from 5 to 100,000, and

R independently at each occurrence is selected from substituted or unsubstituted alkyl, substituted or unsubstituted heteroalkyl, substituted or unsubstituted aryl, and substituted or unsubstituted heteroaryl.

Embodiment 37

A method of preparing a cross-linked polymer membrane at an interface of a first solvent and a second solvent, wherein the first solvent is immiscible with the second solvent, the method comprising the steps of:

a) providing a polymer comprising a first functional group selected from —$N_3$, —C≡CH, C≡C—R', —C≡N, —(C═O)—H, —SH, —CH═$CH_2$, —CH═CHR', —$NH_2$, —NR'—NHR', and —O—NHR', wherein R' is selected from substituted or unsubstituted alkyl, substituted or unsubstituted heteroalkyl, substituted or unsubstituted aryl, substituted or unsubstituted heteroaryl, —CN, —$CO_2$R", —(C═O)—N(R")$_2$, and —(C═O)—R", and R" is independently at each occurrence selected from H, substituted or unsubstituted alkyl, substituted or unsubstituted heteroalkyl, substituted or unsubstituted aryl, and substituted or unsubstituted heteroaryl;

b) fabricating the polymer into a desired membrane;

c) contacting the fabricated membrane of step b) with a compound comprising a second functional group selected from —$N_3$, —C≡CH, C≡C—R', —C≡N, —(C═O)—H, —SH, —CH═$CH_2$, —CH═CHR', —$NH_2$, —NR'—NHR', and —O—NHR', wherein the second functional group is capable of irreversibly reacting with the first functional group to form a covalent connection, by dissolving the fabricated membrane and the compound in the first solvent;

d) combining the first solvent comprising fabricated membrane and the compound and a second solvent comprising a catalyst for initiating a reaction between the first functional group and the second functional group, e) crosslinking the fabricated membrane of step b) with the compound of step c) by reacting the first functional group and the second functional group to form the covalent connection, wherein the crosslinking reaction between the first functional group and the second functional group occurs at the interface of the first solvent and the second solvent, thereby forming the cross-linked polymer membrane at the interface of the first solvent and the second solvent.

Embodiment 38

The method of embodiment 37, wherein the first functional group is selected from —$N_3$ and —C≡CH, and the second functional group is selected from —$N_3$ and —C≡CH, wherein when the first functional group is —$N_3$, the second functional group is —C≡CH, and when the first functional group is —C≡CH, the second functional group is —$N_3$.

Embodiment 39

The method of embodiment 37, wherein the catalyst is a copper catalyst.

Embodiment 40

The method of embodiment 37, wherein the first solvent is an organic solvent and the second solvent is selected from water and a fluorocarbon solvent, or wherein the first solvent is water and the second solvent is selected from an organic solvent and a fluorocarbon solvent; or when the first solvent is a fluorocarbon solvent and the second solvent is selected from an organic solvent and water.

Embodiment 41

The method of embodiment 37, wherein the first solvent is an organic solvent comprising dichloromethane, chlorobenzene, chloroform, methylene chloride, cyclohexane, hexanes, heptanes, 1,2-dichloroethane, diethyl ether, methyl t-butyl ether, carbon tetrachloride, xylenes, toluene, ethyl acetate, or butyl acetate, and the second solvent is selected from water and a fluorocarbon comprising perfluorohexane, perfluoroheptane, perfluorooctane, perfluorononane, 2H,3H-decafluoropentane, perfluorodecaline, perfluoromethylcyclohexane, hexafluorobenzene, octafluorotoluene, perfluoro (1,3-dimethylcyclohexane), perfluorotributylamine, or hexafluoroisopropyl methyl ether.

Embodiment 42

The method of embodiment 37, wherein the first solvent is water and the second solvent is selected from an organic solvent comprising dichloromethane, chlorobenzene, chloroform, methylene chloride, cyclohexane, hexanes, heptanes, 1,2-dichloroethane, diethyl ether, methyl t-butyl ether, carbon tetrachloride, xylenes, toluene, ethyl acetate, or butyl acetate, and a fluorocarbon solvent comprising perfluorohexane, perfluoroheptane, perfluorooctane, perfluorononane, 2H,3H-decafluoropentane, perfluorodecaline, perfluoromethylcyclohexane, hexafluorobenzene, octafluorotoluene, perfluoro(1,3-dimethylcyclohexane), perfluorotributylamine, or hexafluoroisopropyl methyl ether.

Embodiment 43

The method of embodiment 37, wherein the first solvent is a fluorocarbon solvent comprising perfluorohexane, perfluoroheptane, perfluorooctane, perfluorononane, 2H,3H-decafluoropentane, perfluorodecaline, perfluoromethylcyclohexane, hexafluorobenzene, octafluorotoluene, perfluoro(1, 3-dimethylcyclohexane), perfluorotributylamine, or hexafluoroisopropyl methyl ether, and the second solvent is selected from water and an organic solvent comprising dichloromethane, chlorobenzene, chloroform, methylene chloride, cyclohexane, hexanes, heptanes, 1,2-dichloroethane, diethyl ether, methyl t-butyl ether, carbon tetrachloride, xylenes, toluene, ethyl acetate, or butyl acetate.

Embodiment 44

A method of preparing a cross-linked polymer membrane on a solid support comprising the steps of:

a) providing a polymer comprising a first functional group selected from —$N_3$, —C≡CH, C≡C—R', —C≡N, —(C═O)—H, —SH, —CH═$CH_2$, —CH═CHR', —$NH_2$, —NR'—NHR', and —O—NHR', wherein R' is selected from substituted or unsubstituted alkyl, substituted or unsubstituted heteroalkyl, substituted or unsubstituted aryl, substituted or unsubstituted heteroaryl, —CN, —$CO_2$R", —(C═O)—N(R")$_2$, and —(C═O)—R", and R" is independently at each occurrence selected from H, substituted or unsubstituted alkyl, substituted or unsubstituted heteroalkyl, substituted or unsubstituted aryl, and substituted or unsubstituted heteroaryl;

b) submerging a solid support into a solution comprising the polymer comprising the first functional group and a compound comprising a second functional group selected from —N₃, —C≡CH, C≡C—R', —C≡N, —(C=O)—H, —SH, —CH=CH₂, —CH=CHR', —NH₂, —NR'—NHR', and —O—NHR', wherein the second functional group is capable of irreversibly reacting with the first functional group to form a covalent connection;

d) crosslinking the polymer of step a) with the compound of step b) by reacting the first functional group and the second functional group to form the covalent connection on solid support, thus obtaining the cross-linked polymer membrane of a solid support.

Embodiment 45

The method of embodiment 44, wherein the solution comprising the catalyst is an aqueous solution and the catalyst is a water-soluble copper catalyst.

Embodiment 46

The method of embodiment 44, wherein the solution comprising the polymer comprising the first functional group and the compound comprising the second functional group comprises a solvent selected from dichloromethane, chlorobenzene, chloroform, methylene chloride, cyclohexane, hexanes, heptanes, 1,2-dichloroethane, diethyl ether, methyl t-butyl ether, carbon tetrachloride, xylenes, toluene, ethyl acetate, butyl acetate, tetrahydrofuran, tetrahydropyran, dimethyl formamide, NMP, acetone, ethanol, methanol, and toluene.

Embodiment 47

The method of embodiment 44, wherein the solid support is selected from a ceramic surface, a zeolite surface, and a polymer surface. A method of preparing a cross-linked polymer membrane on solid copper support comprising the steps of:

a) providing a first polymer comprising a first functional group selected from —N₃, —C≡CH, C≡C—R', —C≡N, —(C=O)—H, —SH, —CH=CH₂, —CH=CHR', —NH₂, —NR'—NHR', and —O—NHR', and a second polymer comprising a second functional group selected from —N₃, —C≡CH, C≡C—R', —C≡N, —(C=O)—H, —SH, —CH=CH₂, —CH=CHR', —NH₂, —NR'—NHR', and —O—NHR', wherein the second functional group is capable of irreversibly reacting with the first functional group to form a covalent connection;

wherein R' is selected from substituted or unsubstituted alkyl, substituted or unsubstituted heteroalkyl, substituted or unsubstituted aryl, substituted or unsubstituted heteroaryl, —CN, —CO₂R", —(C=O)—N(R")₂, and —(C=O)—R", and R" is independently at each occurrence selected from H, substituted or unsubstituted alkyl, substituted or unsubstituted heteroalkyl, substituted or unsubstituted aryl, and substituted or unsubstituted heteroaryl;

b) coating the copper support with the first polymer and the second polymer;

c) crosslinking the first polymer and the second polymer by reacting the first functional group and the second functional group to form the covalent connection on solid copper support, thus obtaining the cross-linked polymer membrane of solid copper support.

Embodiment 48

The method of embodiment 47, wherein the first and the second polymer are comprised in a single polymer blend comprising the first functional group and the second functional group.

Embodiment 49

The method of embodiment 47, wherein the crosslinking reaction is initiated by heating the copper support coated with the first polymer and the second polymer.

Embodiment 50

A method of preparing a cross-linked polymer membrane covalently attached to a solid support comprising the steps of:

a) covalently attaching to the solid support a compound comprising a first functional group selected from —N₃, —C≡CH, C≡C—R', —C≡N, —(C=O)—H, —SH, —CH=CH₂, —CH=CHR', —NH₂, —NR'—NHR', and —O—NHR', wherein R' is selected from substituted or unsubstituted alkyl, substituted or unsubstituted heteroalkyl, substituted or unsubstituted aryl, substituted or unsubstituted heteroaryl, —CN, —CO₂R", —(C=O)—N(R")₂, and —(C=O)—R", and R" is independently at each occurrence selected from H, substituted or unsubstituted alkyl, substituted or unsubstituted heteroalkyl, substituted or unsubstituted aryl, and substituted or unsubstituted heteroaryl;

b) fabricating a polymer membrane on the functionalized solid support with a polymer comprising a second functional group selected from —N₃, —C≡CH, C≡C—R', —C≡N, —(C=O)—H, —SH, —CH=CH₂, —CH=CHR', —NH₂, —NR'—NHR', and —O—NHR', wherein the second functional group is capable of irreversibly reacting with the first functional group to form a covalent connection, c) reacting the first functional group and the second functional group to form the cross-linked polymer membrane, thus obtaining the cross-linked polymer membrane covalently attached to the solid support.

Embodiment 51

The method of embodiment 50, wherein the reaction of step c) is initiated by heating the polymer-coated functionalized support.

Embodiment 52

The method of embodiment 50, wherein the reaction of step c) is initiated by submerging the polymer-coated functionalized support in a solution comprising a catalyst. In one embodiment, the catalyst is a copper catalyst.

Embodiment 53

A cross-linked polymer membrane prepared according to the method of any of embodiments 1-52.

Embodiment 54

The cross-linked polymer membrane of embodiment 53, wherein the membrane is insoluble in strong polar aprotic solvents.

Embodiment 55

The cross-linked polymer membrane of embodiment 53, wherein the membrane is insoluble in organic solvents comprising dichloromethane, chlorobenzene, chloroform, methylene chloride, cyclohexane, hexanes, heptanes, 1,2-dichloroethane, diethyl ether, methyl t-butyl ether, carbon tetrachloride, xylenes, toluene, ethyl acetate, butyl acetate, DMF, DMAc, NMP, or DMSO, water, and/or fluorocarbons comprising perfluorohexane, perfluoroheptane, perfluorooctane, perfluorononane, 2H,3H-decafluoropentane, perfluorodecaline, perfluoromethylcyclohexane, hexafluorobenzene, octafluorotoluene, perfluoro(1,3-dimethylcyclohexane), perfluorotributylamine, or hexafluoroisopropyl methyl ether.

Embodiment 56

The cross-linked polymer membrane of embodiment 53 having a molecular weight cut-off of about 150 to about 2000 Daltons.

Embodiment 57

The cross-linked polymer membrane of embodiment 53 having a pore size of about 0.5 nm to about 2 nm.

Embodiment 58

A vapor separation system comprising the cross-linked polymer membrane of embodiment 53.

Embodiment 59

The vapor separation system of embodiment 58, suitable for separation of two or more vapors selected from the group consisting of Ethane, Propane, and Butane.

Embodiment 60

A method of separating two or more vapors using a cross-linked polymer membrane of embodiment 53.

Embodiment 61

A liquid separation system comprising the cross-linked polymer membrane of embodiment 53.

Embodiment 62

The liquid separation system of embodiment 62, suitable for separation of crude oil.

Embodiment 63

The liquid separation system of embodiment 62, suitable for separation of whole crude oil and/or crude oil fractions.

Embodiment 64

The liquid separation system of embodiment 62, capable of separating a naphtha and/or a kerosene fraction of whole crude oil.

Embodiment 65

A method of separating two or more liquids using a cross-linked polymer membrane of embodiment 53.

Embodiment 66

A method of removing a homogenous catalyst from an organic solvent using a cross-linked polymer membrane of embodiment 53.

Embodiment 67

The method of embodiment 67, wherein the homogenous catalyst is selected from rhodium, nickel, and cobalt.

Embodiment 68

A method of removing residual water from an alcohol using a cross-linked polymer membrane of embodiment 53.

Embodiment 69

The method of embodiment 68, wherein the alcohol is selected from ethanol, propanol, and butanol.

Embodiment 70

A membrane reactor comprising a cross-linked polymer membrane of embodiment 53.

What is claimed is:

1. A method of preparing a cross-linked polymer membrane comprising the steps of:
   a) providing a first polymer comprising a first functional group Z selected from —$N_3$, —C≡CH, C=C—R', —C≡N, —(C=O)—H, —SH, —CH=$CH_2$, —CH=CHR', —$NH_2$, —NR'—NHR', and —O—NHR' and a second polymer comprising a second functional group Z selected from —$N_3$, —C≡CH, C=C—R', —C≡N, —(C=O)—H, —SH, —CH=$CH_2$, —CH=CHR', —$NH_2$, —NR'—NHR', and —O—NHR'
   wherein the first polymer and the second polymer each have a chemical structure:

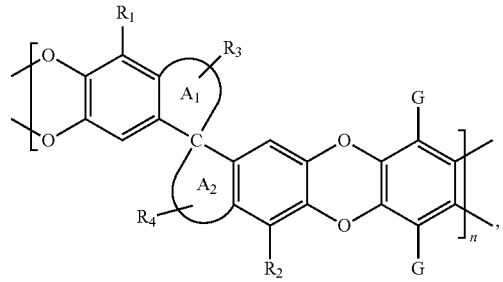

wherein: the carbon indicated by "C" denotes a spiro-carbon;
$A_1$ is selected from

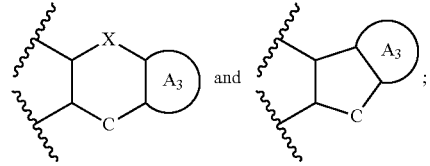

$A_2$ is

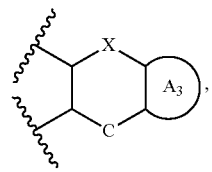

X is independently at each occurrence selected from —CR6, —O—, —S—, —N(R6)2, —C=O, —NR6, —C=N—N(R6)2, and C=N—OR6;

R1, R2, R3, and R4 are each independently selected from H and Y—Z;

R6 is independently at each occurrence selected from H, substituted or unsubstituted alkyl, substituted or unsubstituted heteroalkyl, substituted or unsubstituted aryl, and substituted or unsubstituted heteroaryl;

A3 is a selected from substituted or unsubstituted C5-C6 aryl, substituted or unsubstituted C5-C6 heteroaryl, substituted or unsubstituted C5-C6 cycloalkyl and substituted or unsubstituted C5-C6 cyclic heterocycloalkyl;

Y is independently absent or selected from substituted or unsubstituted alkyl, substituted or unsubstituted aryl, —NH—(C=O)—; =NO—C1-6 alkyl-; and —(C=O)-phenyl-;

G is selected from Y—Z, halogen, —CN, substituted or unsubstituted aryl, and substituted or unsubstituted heteroaryl;

n is an integer from 5 to 100,000;

wherein R' is independently at each occurrence selected from substituted or unsubstituted alkyl, substituted or unsubstituted heteroalkyl, substituted or unsubstituted aryl, substituted or unsubstituted heteroaryl, —CN, —CO$_2$R", —(C=O)—N(R")$_2$, and —(C=O)—R", and R" is independently at each occurrence selected from H, substituted or unsubstituted alkyl, substituted or unsubstituted heteroalkyl, substituted or unsubstituted aryl, and substituted or unsubstituted heteroaryl, and wherein the first functional group and the second functional group are capable of irreversibly reacting with each other to form a covalent connection;

b) fabricating the first polymer and the second polymer into a polymer membrane;

c) crosslinking the fabricated membrane of step b) by reacting the first functional group and the second functional group to form the covalent connection, thus obtaining the cross-linked polymer membrane.

2. The method of claim 1, wherein

Z is the functional group selected from —N$_3$, —C≡CH, C≡C—R', —C≡N, —(C=O)—H, —SH, and —CH=CH$_2$.

3. The method of claim 1, wherein the first polymer comprises the first functional group selected from —N$_3$ and —C≡CH, and the second polymer comprises the second functional group selected from —N$_3$ and —C≡CH, wherein when the first functional group is —N$_3$, the second functional group is —C≡CH, and when the first functional group is —C≡CH, the second functional group is —N$_3$.

4. The method of claim 1, wherein the polymer membrane has a form factor selected from hollow fiber membranes, spiral wound membranes, plate-and-frame membranes, coated monoliths, tubes, and discs.

5. The method of claim 4, wherein the polymer membrane form factor is a hollow fiber membrane.

6. The method of claim 1, wherein the polymer membrane has a morphology selected from an integrally-skinned asymmetric morphology or a thin film composite morphology.

7. The method of claim 1, wherein the first polymer and the second polymer are fabricated into the polymer membrane using one or more fabrication techniques selected from dry jet-wet quench solution spinning, slip casting, dip coating, blade coating, spin casting, chemical vapor deposition, interfacial polymerization, tape casting, and melt extrusion.

8. The method of claim 1, wherein the step b) of fabricating the first polymer and the second polymer into the polymer membrane further comprises exchanging solvent and drying the fabricated membrane.

9. The method of claim 1, wherein the step c) of crosslinking the fabricated membrane of step b) comprises subjecting the fabricated membrane to heat, UV-visible light, a dehydrating agent, and/or a catalyst to react the first functional group and the second functional group.

10. The method of claim 1, wherein the step c) of crosslinking the fabricated membrane of step b) comprises submersing the fabricated membrane in a nonsolvent solution comprising a catalyst for the reaction between the first functional group and the second functional group.

11. A method of preparing a cross-linked polymer membrane according to Scheme 1:

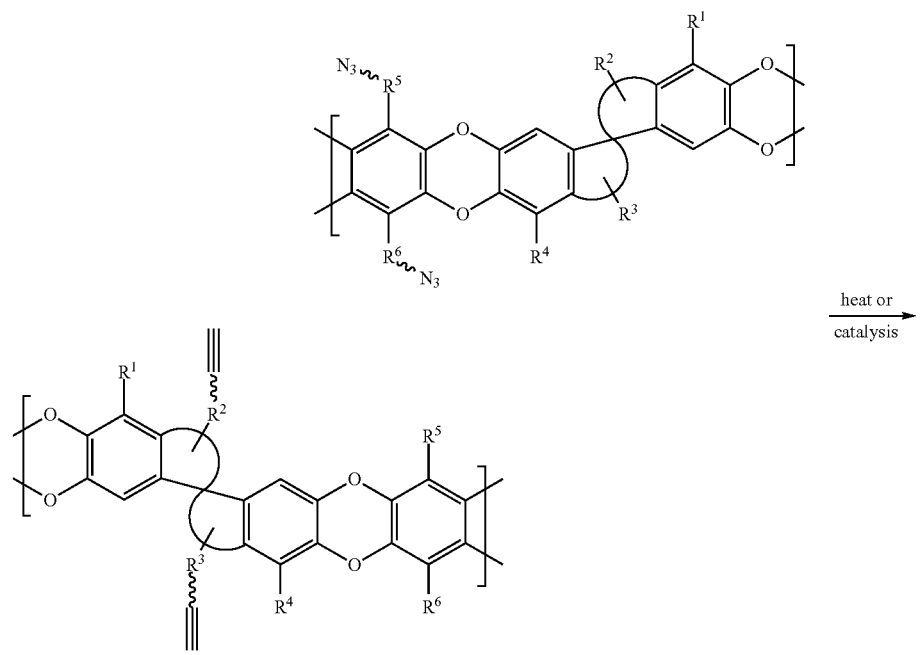

Scheme 1

-continued

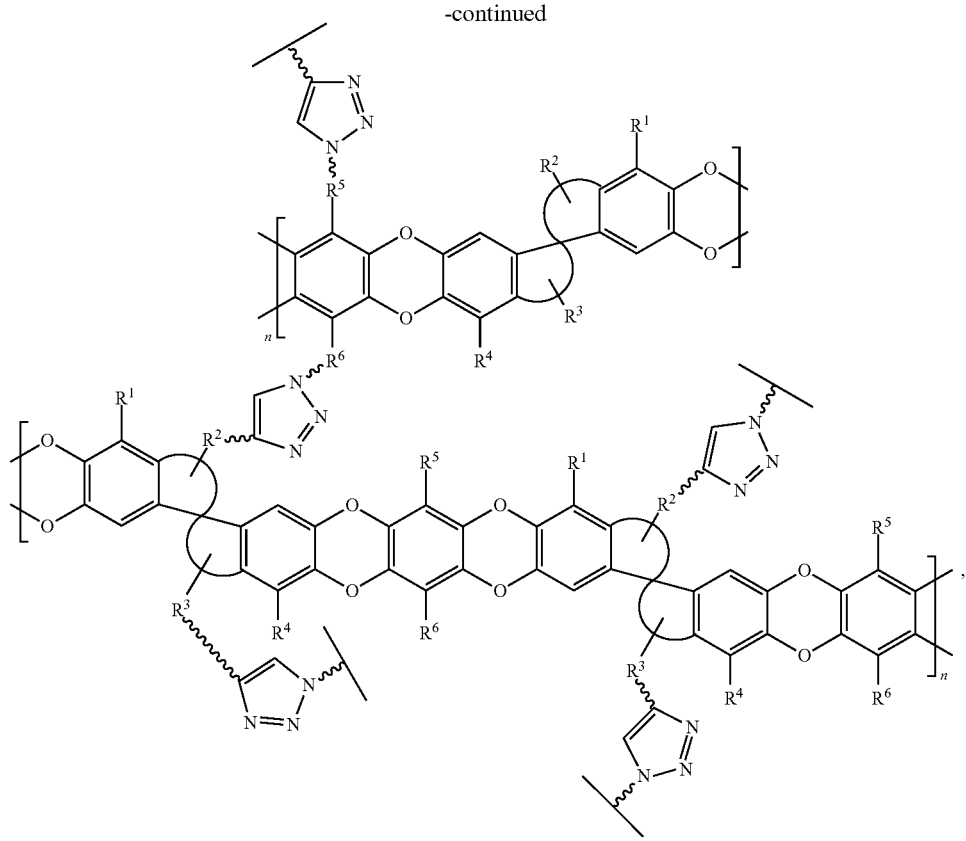

wherein $R_1$, $R_2$, $R_3$, $R_4$, $R_5$, and $R_6$ are each independently at each occurrence selected from H, substituted or unsubstituted alkyl, substituted or unsubstituted heteroalkyl, substituted or unsubstituted aryl, and substituted or unsubstituted heteroaryl,
the method comprising the steps of:
a) providing a first polymer comprising a first functional group —$N_3$ and a second polymer comprising a second functional group —C≡CH,
b) fabricating the first polymer and the second polymer into a desired membrane;
c) crosslinking the fabricated membrane of step b) by reacting the first functional group —$N_3$ and the second functional group —C≡CH to form a triazole connection,
thus obtaining the cross-linked polymer membrane.

12. The method of claim 11, wherein step c) of crosslinking the fabricated membrane of step b) comprises heating the fabricated membrane to between about room temperature and about 200° C. to react the first functional group and the second functional group.

13. The method of claim 11, wherein the step c) of crosslinking the fabricated membrane of step b) comprises submersing the fabricated membrane in a nonsolvent solution comprising a copper catalyst for the reaction between the first functional group —$N_3$ and the second functional group —C≡CH.

14. The method of claim 13, wherein the nonsolvent solution comprising a copper catalyst is a solution of copper (I) salt.

15. The method of claim 14, wherein the copper(I) salt is selected from copper(I) ascorbate, copper(I) iodide, copper (I) bromide, copper(I) chloride, copper(I) acetate, $L_nCu(I)$X, where L is selected from phosphine, amine, and pyridyl, n is an integer from 0 to 4, and X is selected from Cl, Br, I, OAc, and $BF_4$.

16. The method of claim 14, wherein the copper(I) salt is a combination of Cu(II) salt selected from $CuSO_4$, $Cu(OAc)_2$, $CuBr_2$, $CuCl_2$ and sodium ascorbate.

17. A method of preparing a cross-linked polymer membrane according to Scheme 2:

Scheme 2,

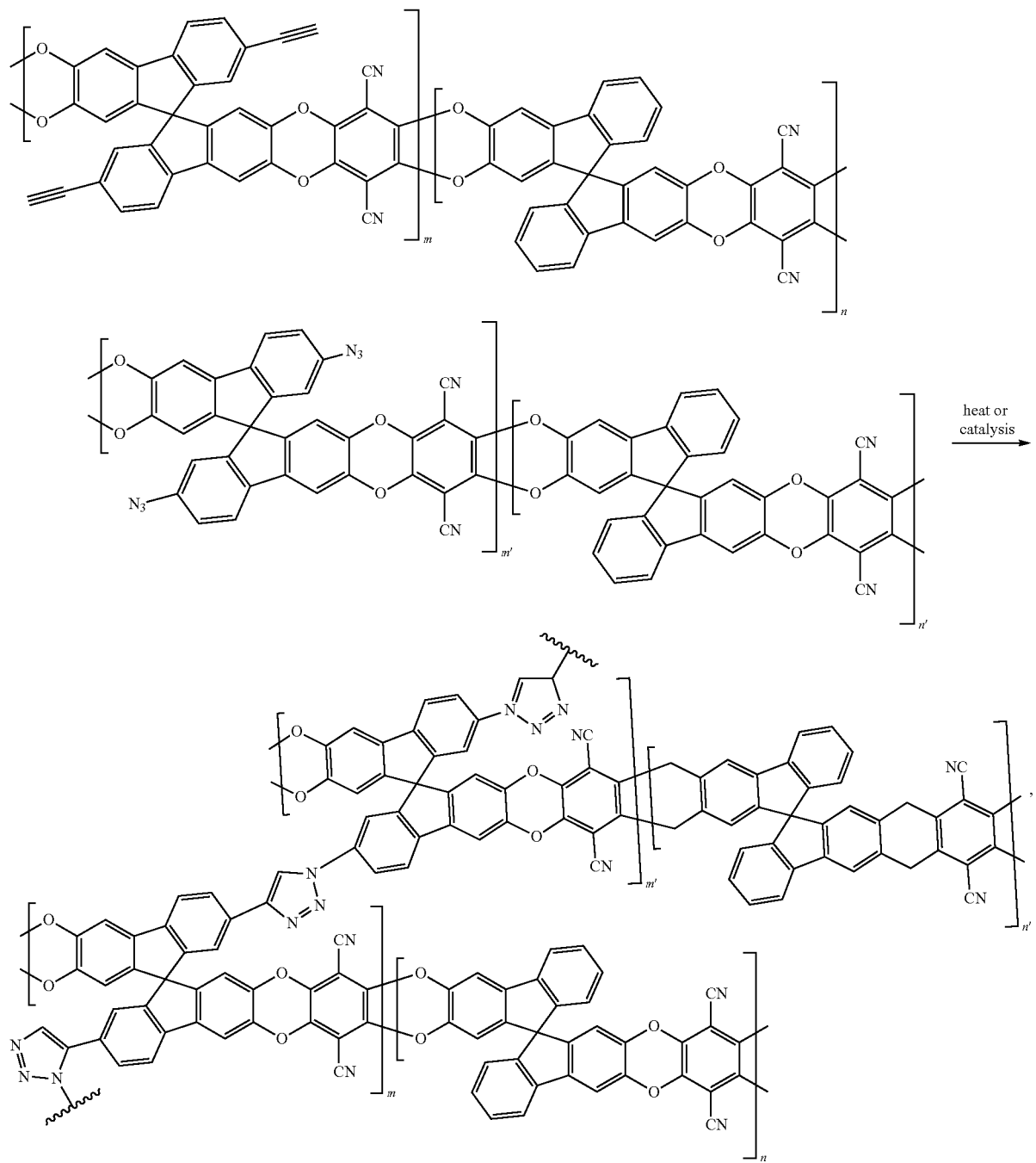

wherein n, n', m', and m' are each independently an integer from 5 to 100,000, the method comprising the steps of:
a) providing a first polymer comprising a first functional group —$N_3$ and a second polymer comprising a second functional group —C≡CH,
b) fabricating the first polymer and the second polymer into a desired membrane;
c) crosslinking the fabricated membrane of step b) by reacting the first functional group —$N_3$ and the second functional group —C≡CH to form a triazole connection, thus obtaining the cross-linked polymer membrane.

18. The method of claim 17, wherein the step b) of fabricating the first polymer and the second polymer into a desired membrane is performed in a solvent.

19. The method of claim 17, wherein the step c) of crosslinking the fabricated membrane of step b) comprises submersing the fabricated membrane in a nonsolvent solution comprising a copper catalyst for the reaction between the first functional group —$N_3$ and the second functional group —C≡CH.

20. The method of claim 19, wherein the nonsolvent solution comprising a copper catalyst is a solution of copper ascorbate.

* * * * *